US 6,713,071 B1

United States Patent
Ankenbauer et al.

(10) Patent No.: US 6,713,071 B1
(45) Date of Patent: Mar. 30, 2004

(54) **PROTEINS FROM *ACTINOBACILLUS PLEUROPNEUMONIAE***

(75) Inventors: Robert G. Ankenbauer, Pawcatuck, CT (US); Mary Jo Baarsch, Niantic, CT (US); Manuel Campos, Stonington, CT (US); Robin Keich, Waterford, CT (US); Everett Rosey, Preston, CT (US); Brian Suiter, Lincoln, NE (US); Lynn Warren-Stewart, Colchester, CT (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 0 days.

(21) Appl. No.: 09/418,980

(22) Filed: Oct. 14, 1999

Related U.S. Application Data
(60) Provisional application No. 60/105,285, filed on Oct. 22, 1998.

(51) Int. Cl.[7] ................................ A61K 39/02
(52) U.S. Cl. ................ 424/234.1; 424/190.1; 424/192.1; 530/350
(58) Field of Search .................. 424/197.11, 190.1, 424/192.1, 193.1, 194.1, 234.1; 530/350; 435/69.3, 252.3, 254.4, 320.1, 325, 69.1, 851, 7.1, 7.2

(56) References Cited

U.S. PATENT DOCUMENTS

| | | | | |
|---|---|---|---|---|
| 4,981,685 A | * | 1/1991 | Gerlach et al. | 424/92 |
| 5,225,194 A | * | 7/1993 | Suer | 424/92 |
| 5,332,572 A | * | 7/1994 | Ross et al. | 424/234.1 |
| 5,441,736 A | * | 8/1995 | Gerlach et al. | 424/190.1 |
| 5,543,304 A | * | 8/1996 | Mulks et al. | 435/69.3 |
| 5,616,328 A | * | 4/1997 | Roberts et al. | 424/257.1 |
| 5,648,081 A | * | 7/1997 | van den Bosch | 424/255.1 |
| 5,879,952 A | * | 3/1999 | Mulks et al. | 436/518 |
| 5,891,677 A | * | 4/1999 | Gerlach et al. | 435/69.3 |
| 5,911,966 A | * | 6/1999 | Mulks et al. | 424/197.11 |
| 6,019,984 A | * | 2/2000 | MacInnes et al. | 424/255.1 |
| 6,022,728 A | * | 2/2000 | Mulks et al. | 435/252.1 |

FOREIGN PATENT DOCUMENTS

| | | | |
|---|---|---|---|
| EP | 453 024 | * | 10/1991 |
| EP | 0 453 024 A1 | | 10/1991 |
| EP | 563288 | * | 6/1993 |

OTHER PUBLICATIONS

Fedorka–Cray et al, Infection and Immunity, vol. 58(2), Feb. 1990, pp. 358–365.*

Fedorka–Cray et al, Veterinary microbiology, vol. 37(1–2), pp. 85–100, Oct. 1993.*

T. Sirakova,et al., Role of Fimbriae Expressed by Nontypeable Haemophilus influenzae in Pathogenesis of and Protection against Otitis Media and Relatedness of the Fimbrin Subunit to Outer Membrane Protein A, Infection And Immunity, May 1994, p. 2002–2020, American Society for Microbiology.

Julia Klesney–Tait, et al. The Major Outer Membrane Protein of Haemophilusducreyi Consists of Two OmpA Homologs, , Journal of Bacteriology, Mar., 1997, p 1764–1773, American Society for Microbiology.

M. B. Jalajakumari, et al., Nucleotide sequence of the gene, ompW, encoding a 22kDa immunogenic outer membrane protein of Vibriocholerae, Nucleic Acids Research, vol. 18, No. 8, Apr. 25, 1990, p. 2180.

* cited by examiner

*Primary Examiner*—Lynette R. F. Smith
*Assistant Examiner*—Ginny Allen Portner
(74) *Attorney, Agent, or Firm*—Scully, Scott, Murphy & Presser

(57) ABSTRACT

The present invention is directed to five novel, low molecular weight proteins from *Actinobacillus pleuropneumoniae* (*APP*), which are capable of inducing, or contributing to the induction of, a protective immune response in swine against *APP*. The present invention is further directed to polynucleotide molecules having nucleotide sequences that encode the proteins, as well as vaccines comprising the proteins or polynucleotide molecules, and methods of making and using the same.

5 Claims, 6 Drawing Sheets

Figure 1A:
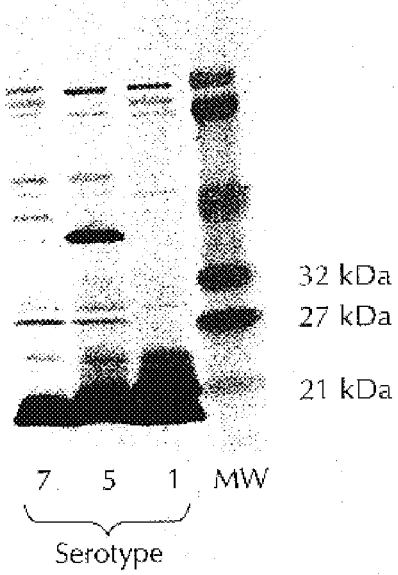

```
App_OmpA1    MKKSLVALTVLSAAAVAQAAPQQNTFYAGAKAGWASFHDGIEQLDS---AKNTDRGTKYG
App_OmpA2    MKKSLVALAVLSAAAVAQAAPQQNTFYAGAKVGQSSFPHHGVNQLKSGHDDRYNDKTRKYG
             ******* ******************* *  *** *  ** *    . *.   ***

App_OmpA1    INRNSVTYGVFGGYQILNQDKLGLAAELGYDYFGRVRGSEKPNGKADKKTFRHAAHGATI
App_OmpA2    INRNSVTYGVFGGYQILNQNNFGLATELGYDYYGRVRGND---G---EFRAMKHSAHGLNF
             ******************.***  ****.*** * ****.       .  .*.*** .

App_OmpA1    ALKPSYEVLPDLDVYGKVGIALVNNTYKTF---NAAQEKVKTRRFQSSLILGAGVEYAIL
App_OmpA2    ALKPSYEVLPDLDVYGKVGVAVVRNDYKSYGAENTNEPTEKFHKLKASTILGAGVEYAIL
             *******************.*.*  * **..   *.  .   *  .  .* **********

App_OmpA1    PELAARVEYQWLNNAG---KASYSTLNRMGATDYRSDISSVSAGLSYRFGQGAV-PVAAP
App_OmpA2    PELAARVEYQYLNKAGNLNKALVRSGTQDVDFQYAPDIHSVTAGLSYRFGQGAVAPVVEP
             ********** ** **   **      .       * ** **.**********  * *

App_OmpA1    AVETKNFAFSSDVLFAFGKSNLKPAAATALDAMQTEINNAGLSNAAIQVNGYTDRIGKEA
App_OmpA2    EVVTKNFAFSSDVLFDFGKSSLKPAAATALDAANTEIANLGLATPAIQVNGYTDRIGKEA
              * ************ **** ************ .*** *  ** . ************

App_OmpA1    SNLKLSQRRAETVANYIVSKGAPAANVTAVGYGEANPVTGATCDKVKGRKALIACLAPDR
App_OmpA2    SNLKLSQRRAETVANYLVSKGQNPANVTAVGYGEANPVTGATCDKVKGRKALIACLAPDR
             **************** .****    **********************************

App_OmpA1    RVEVQVQGTKEVTM
App_OmpA2    RVEVQVQGAKNVAM
             ******** *.*.*
```

FIG. 5

```
App_OmpA1  MKKSLVALTVLSAAAVAQAAPQQNTFYAGAKAGAWASFHDGIEQLDS---AKNTDRGTKYG
App_OmpA2  MKKSLVALAVLSAAAVAQAAPQQNTFYAGAKAGAKVGQSSFHHGVNQLKSGHDDRYNDKTRKYG
           ********.*********************** ***.  *   . .***

App_OmpA1  INRNSVTYGVFGGYQILNQDKLGLAAELGYDYFGRVRGSEKPNGKADKKTFRHAAHGATI
App_OmpA2  INRNSVTYGVFGGYQILNQNNFGLATELGYDYYGRVRGND---G---EFRAMKHSAHGLNF
           ******************   .****  ****** ****.       *   * . ***

App_OmpA1  ALKPSYEVLPDLDVYGKVGIALVNNTYKTF---NAAQEKVKTRRFQSSLILGAGVEYAIL
App_OmpA2  ALKPSYEVLPDLDVYGKVGVAVVRNDYKSYGAENTNEPTEKFHKLKASTILGAGVEYAIL
           *******************.*:.* .**.:   . :* .*:* ::.:** *********

App_OmpA1  PELAARVEYQWLNNAG---KASYSTLNRMGATDYRSDISSVSAGLSYRFGQAV-PVAAP
App_OmpA2  PELAARVEYQYLNKAGNLNKAGNLNKALVRSGTQDVDFQYAPDIHSVTAGLSYRFGQAVAPVVEP
           **********:**.**    *:* **.   *:* . :. .: .  ********** ** **

App_OmpA1  AVETKNFAFSSDVLFAFGKSNLKPAAATALDAMQTEINNAGLSNAAIQVNGYTDRIGKEA
App_OmpA2  EVVTKNFAFSSDVLFDFGKSSLKPAAATALDAANTEIANLGLATPAIQVNGYTDRIGKEA
           .*.************.****.*********** .*** * **:. .*************

App_OmpA1  SNLKLSQRRAETVANYIVSKGAPAANVTAVGYGEANPVTGATCDKVKGRKALIACLAPDR
App_OmpA2  SNLKLSQRRAETVANYLVSKGQNPANVTAVGYGEANPVTGATCDKVKGRKALIACLAPDR
           ****************:****   *****************************************

App_OmpA1  RVEVQVQGTKEVTM
App_OmpA2  RVEVQVQGAKNVAM
           ********:*:*:*
```

FIG. 6

```
VC_OmpW   MKQTICLAVLA-ALLAAPVFAHQEGDFIVRAGIASVVPNDSSDKVLNTQSELAVNANTHL
App_OmpW  MKKAVLAAVLGGALLAGSAMAHQAGDVIFRAGAIGVIANSSSDYQTGADVNLDVNNNIQL
          *  .   * *   ****  ***** ****  *  *  ****    *  *   *  *

VC_OmpW   GLTLGYMFTDNISFEVLARTPFSHKISTSGGELGSLGDIGETKHLPPTFMVQYYFGEANS
App_OmpW  GLTGTYMLSDNLGLELLAATPFSHKITGKLG-ATDLGEVAKVKHLPPSLYLQYYFFDSNA
          *** .**::****  *:   ******* . .*  * **    ****::::****  :*:

VC_OmpW   TNRPYVGAGLNYTFFDESFNSTGTNNALSDLKLDDSWGLAANVGFDYMLNDSWFLNAYV
App_OmpW  TVRPYVGAGLNYTRFFSAESLKPQLVQNLRVKKHSVAP--IANLGVDVKLTDNLSFNAAA
          * *********** :*. :*. .  . **.:  . . ** *    *  * ** ****

VC_OmpW   WYANIETTATYKA-GADAKSTDVEINPWVFIIAGGYKF
App_OmpW  WYTRIKTTADYDVPGLGHVSTPITLDPVVLFSGISYKF
          **: *:*** *.. *    **  .  ** :.* .***
```

VC_OmpW
App_OmpW

VC_OmpW
App_OmpW

VC_OmpW
App_OmpW

VC_OmpW
App_OmpW

PROTEINS FROM ACTINOBACILLUS PLEUROPNEUMONIAE

This application claims priority from provisional application Ser. No. 60/105,285, which was filed on Oct. 22, 1998, now abandoned and which is incorporated by reference in its entirety herein.

1. FIELD OF THE INVENTION

The present invention is in the field of animal health, and is directed to vaccines that protect swine against *Actinobacillus pleuropneumoniae*. More particularly, the present invention is directed to novel antigenic proteins shared by multiple serotypes of *A. pleuropneumoniae*, DNA molecules encoding the proteins, vaccines against *APP* comprising the proteins, and diagnostic reagents.

2. BACKGROUND OF THE INVENTION

*A. pleuropneumoniae* (hereinafter referred to as "*APP*") is a Gram negative coccobacillus recognized as one of the most important swine pneumonic pathogens (Shope, R. E., 1964, J. Exp. Med. 119:357–368; Sebunya, T. N. K. and Saunders, J. R., 1983, J. Am. Vet. Med. Assoc. 182:1331–1337). Twelve different serotypes have been recognized which vary in geographic distribution (Sebunya, T. N. K. and Saunders, J. R., 1983, above; Nielsen, R., 1985, Proc. Am. Assoc. Swine Pract. 18–22; Nielsen, R., 1986, Acta. Vet. Scand. 27:453–455). Immune responses to vaccination against *APP* have been mainly serotype-specific, suggesting that vaccine-induced immunity is directed to serotype-specific capsular antigens (MacInnes, J. I.). and Rosendal, S., 1988, Can. Vet. J. 29:572–574; Fedorka-Cray, P. J., et al., 1994, Comp. Cont. Educ. Pract. Vet. 16:117–125; Nielsen, R., 1979, Nord. Vet. Med. 31:407–413; Rosendal, S., et al., 1986, Vet. Microbiol. 12:229–240).

In contrast, natural immunity to any one serotype seems to confer significant protection from disease caused by other serotypes, suggesting that natural exposure induces cross-reactive immunity to shared antigens (Sebunya, T. N. K. and Saunders, J. R., 1983, above; Macinnes, J. I. and Rosendal, S., 1988, above; Fedorka-Cray, P. J., et al., 1994, above; Nielsen, R., 1979, above; and Rosendal, S., et al., 1986, above).

Virulence factors that might contribute to cross-protection have been proposed as possible vaccine candidates, including exotoxins (Apx) (Nakai, T., et al., 1983, Am. J. Vet. Res. 30 44:344–347; Frey, J., et al., 1993, J. Gen. Microbiol. 139:1723–1728; Fedorka-Cray, P. J., et al., 1993, Vet. Microbiol. 37:85–100); capsular antigens (Rosendal, S., et al., 1986, above); outer-membrane proteins (OMP) (Denee, H. and Potter, A., 1989, Infect. Immune 57:798–804; Niven, D. F., et al., 1989, Mol. Microbiol. 3:1083–1089; Gonzalez, G., et al., 1990, Mol. Microbiol. 4:1173–1179; Gerlach, G. F., et al., 1992, Infect. Immun. 60:3253–3261); and lipopolysaccharides (LPS) (Fenwick, B. W. and Osborn, B., 1986, Infect. Immun. 54:575–582). However, the patterns of cross-reactivity/cross-protection induced by such components do not cover all twelve *APP* serotypes. In addition, immunization with isolated individual components or combinations of individual components from *APP* have so far failed to confer protection from challenge with some heterologous serotypes (unpublished observations). Thus, it can be postulated that the cross-protective responses induced by natural infection are limited to specific serotype clusters.

Alternatively, it is possible that some of the antigens responsible for the cross-protection observed after natural infection have not yet been identified. Most studies regarding *APP* antigens have focused on the characterization of immunodominant antigens detected in convalescent serum using antibodies. Such an approach does not allow the identification of possible differences between the antibody specificities represented during primary versus secondary responses, nor the identification of dominant specificities at the infection site that are likely to be responsible for protection upon secondary encounter with the pathogen.

It is generally accepted that lymphocytes are educated during primary infections so that when there is secondary exposure to a pathogen the host is better able to prevent disease (MacKay, C. R., 1993, Adv. Immunol. 53:217–240). Memory cells responsible for this activity (antigen-experienced T and B lymphocytes) persist for long periods of time, and are capable of reactivation following an appropriate subsequent encounter with the antigen. In contrast to naive cells, they generally show a faster response time, specialized tissue localization, and more effective antigen recognition and effector functions (MacKay, C. R., 1993, above; Linton, P. and Klinman, N. R., 1992, Sem. Immun. 4:3–9; Meeusen, E. N. T., et al., 1991, Eur. J. Immunol. 21:2269–2272).

During the generation of a secondary response, the frequency of precursor cells capable of responding to the particular antigen is higher than that present during the primary response. Trafficking patterns of memory cell subsets following secondary responses are also different from those of naive cells. Naive cells migrate relatively homogeneously to secondary lymphoid tissues, but they home poorly to non-lymphoid tissues. By contrast, memory cells display heterogeneous trafficking and, in some instances, migration has been shown to be restricted to certain secondary lymphoid tissues and non-lymphoid sites (MacKay, C. R., 1993, above; Gray, D., 1993, Ann. Rev. Immunol. 11:49–77; Picker, L. S., et al., 1993, J. Immunol. 150:1122–1136). Studies in both rodents and sheep have indicated that lymphocytes from the gut preferentially migrate back to the gut, whereas cells draining from the skin or from lymph nodes preferentially migrate back to the skin or lymph nodes (Gray, D., 1993, above; Picker, L. S., et al., 1993, above). Thus, upon secondary encounter with a pathogen, specific effector cells for cell-mediated immunity and antibody secretion can home to infection sites and local lymph nodes more effectively (Meeusen, E. N. T., et al., 1991, above). As a result, infiltrating lymphocytes will rapidly proliferate and their specificities will predominate during early stages of re-infection.

Recovery of local B cells from tissues and draining lymph nodes early after re-infection has allowed some researchers to obtain antibodies with a narrower specificity range (Meeusen, E. N. T. and Brandon, M., 1994, J. Immunol. Meth. 172:71–76). Such antibodies have been successfully used to identify potential protective antigens to several pathogens (Meeusen, E. N. T. and Brandon, M., 1994, above; Meeusen, E. N. T. and Brandon, M., 1994, Eur. J. Immunol. 24:469–474; Bowles, V. M., et al., 1995, Immunol. 84:669–674). The invention disclosed herein below is based on a modification of this approach, in which antibody-secreting cell (ASC) probes were recovered that were associated with local memory responses elicited after homologous and heterologous *APP* challenge. Antibodies obtained from bronchial lymph node (BLN) cultures after heterologous challenge recognized four previously unrecognized proteins present in all twelve *APP* serotypes. Partial amino acid sequences for each protein were obtained and used to generate PCR primers that allowed the identification of five novel *APP* proteins and polynucleotide molecules that encode them.

3. SUMMARY OF THE INVENTION

The present invention provides five novel, low molecular weight proteins isolated from *APP*, which are designated herein, respectively, as "Omp20," "OmpW," "Omp27," "OmpA1," and "OmpA2". These "*APP* proteins" and the polynucleotide molecules that encode them are useful either as antigenic components in a vaccine to protect swine against *APP*, or as diagnostic reagents to identify swine that are, or have been, infected with *APP*, or that have been vaccinated with a vaccine of the present invention.

The amino acid sequence of Omp20 is encoded by the Omp20-encoding ORF of plasmid pER416 which is present in host cells of strain Pz416 (ATCC 98926), and its deduced amino acid sequence is presented as SEQ ID NO:2, which comprises a signal sequence from amino acid residues 1 to 19. The amino acid sequence of OmpW is encoded by the OmpW-encoding ORF of plasmid pER418 which is present in host cells of strain Pz418 (ATCC 98928), and its deduced amino acid sequence is presented as SEQ ID NO:4, which comprises a signal sequence from amino acid residues 1 to 21. The amino acid sequence of Omp27 is encoded by the Omp27-encoding ORF of plasmid pER417 which is present in host cells of strain Pz417 (ATCC 98927), and its deduced amino acid sequence is presented as SEQ ID NO:6, which comprises a signal sequence from amino acid residues 1 to 27. The amino acid sequence of OmpA1 is encoded by the OmpA1-encoding ORF of plasmid pER419 which is present in host cells of strain Pz419 (ATCC 98929), and its deduced amino acid sequence is presented as SEQ ID NO:8, which comprises a signal sequence from amino acid residues 1 to 19. The amino acid sequence of OmpA2 is encoded by the OmpA2-encoding ORF of plasmid pER420 which is present in host cells of strain Pz420 (ATCC 98930), and its deduced amino acid sequence is presented as SEQ ID NO:10, which comprises a signal sequence from amino acid residues 1 to 19. Each of these *APP* proteins, in substantially purified form, is provided by the present invention.

The present invention further provides substantially purified polypeptides that are homologous to any of the aforementioned *APP* proteins of the present invention. The present invention further provides peptide fragments of any of the *APP* proteins or homologous polypeptides of the present invention. The present invention further provides fusion proteins comprising an *APP* protein, homologous polypeptide, or peptide fragment of the present invention joined to a carrier or fusion partner. The present invention further provides analogs and derivatives of an *APP* protein, homologous polypeptide, peptide fragment, or fusion protein of the present invention.

The present invention further provides an isolated polynucleotide molecule comprising a nucleotide sequence encoding the *APP* protein, Omp20, with or without signal sequence. In a preferred embodiment, the isolated Omp20-encoding polynucleotide molecule of the present invention comprises the nucleotide sequence of SEQ ID NO:1 from about nt 329 to about nt 790. In a more preferred embodiment, the isolated Omp20-encoding polynucleotide molecule of the present invention comprises the nucleotide sequence of SEQ ID NO:1 from about nt 272 to about nt 790.

The present invention further provides an isolated polynucleotide molecule comprising a nucleotide sequence encoding the *APP* protein, OmpW, with or without signal sequence. In a preferred embodiment, the isolated OmpW-encoding polynucleotide molecule of the present invention comprises the nucleotide sequence of SEQ ID NO:3 from about nt 439 to about nt 1023. In a more preferred embodiment, the isolated OmpW-encoding polynucleotide molecule of the present invention comprises the nucleotide sequence of SEQ ID NO:3 from about nt 376 to about nt 1023.

The present invention further provides an isolated polynucleotide molecule comprising a nucleotide sequence encoding the *APP* protein, Omp27, with or without signal sequence. In a preferred embodiment, the isolated Omp27-encoding polynucleotide molecule of the present invention comprises the nucleotide sequence of SEQ ID NO:5 from about nt 238 to about nt 933. In a more preferred embodiment, the isolated Omp27-encoding polynucleotide molecule of the present invention comprises the nucleotide sequence of SEQ ID NO:5 from about nt 157 to about nt 933.

The present invention further provides an isolated polynucleotide molecule comprising a nucleotide sequence encoding the *APP* protein, OmpA1, with or without signal sequence. In a preferred embodiment, the isolated OmpA1-encoding polynucleotide molecule of the present invention comprises the nucleotide sequence of SEQ ID NO:7 from about nt 671 to about nt 1708. In a more preferred embodiment, the isolated OmpA1-encoding polynucleotide molecule of the present invention comprises the nucleotide sequence of SEQ ID NO:7 from about nt 614 to about nt 1708.

The present invention further provides an isolated polynucleotide molecule comprising a nucleotide sequence encoding the *APP* protein, OmpA2, with or without signal sequence. In a preferred embodiment, the isolated OmpA2-encoding polynucleotide molecule of the present invention comprises the nucleotide sequence of SEQ ID NO:9 from about nt 254 to about nt 1306. In a more preferred embodiment, the isolated OmpA2-encoding polynucleotide molecule of the present invention comprises the nucleotide sequence of SEQ ID NO:9 from about nt 197 to about nt 1306.

The present invention further provides an isolated polynucleotide molecule that is homologous to any of the aforementioned polynucleotide molecules of the present invention. The present invention further provides an isolated polynucleotide molecule comprising a nucleotide sequence that encodes a polypeptide that is homologous to any of the *APP* proteins of the present invention. The present invention further provides an isolated polynucleotide molecule consisting of a nucleotide sequence that is a substantial portion of any of the aforementioned polynucleotide molecules of the present invention. In a non-limiting embodiment, the substantial portion of a polynucleotide molecule of the present invention encodes a peptide fragment of an *APP* protein or homologous polypeptide of the present invention. The present invention further provides a polynucleotide molecule comprising a nucleotide sequence that encodes a fusion protein comprising an *APP* protein, homologous polypeptide, or peptide fragment of the present invention joined to a carrier or fusion partner.

The present invention further provides oligonucleotide molecules that are useful as primers for amplifying any of the polynucleotide molecules of the present invention, or as diagnostic reagents. Specific though non-limiting embodiments of such oligonucleotide molecules include oligonucleotide molecules having nucleotide sequences selected from the group consisting of any of SEQ ID NOS:15–47 and 49–93.

The present invention further provides compositions and methods for cloning and expressing any of the polynucleotide molecules of the present invention, including recombinant cloning vectors and recombinant expression vectors comprising a polynucleotide molecule of the present invention, host cells transformed with any of said vectors, and cell lines derived therefrom.

The present invention further provides a recombinantly-expressed APP protein, homologous polypeptide, peptide fragment, or fusion protein encoded by a polynucleotide molecule of the present invention.

The present invention further provides a vaccine for protecting swine against APP, comprising an immunologically effective amount of one or more antigens of the present invention selected from the group consisting of an APP protein, homologous polypeptide, peptide fragment, fusion protein, analog, derivative, or polynucleotide molecule of the present invention capable of inducing, or contributing to the induction of, a protective response against APP in swine; and a veterinarily acceptable carrier or diluent. The vaccine of the present invention can further comprise an adjuvant or other immunomodulatory component. In a non-limiting embodiment, the vaccine of the present invention can be a combination vaccine for protecting swine against APP and, optionally, one or more other diseases or pathological conditions that can afflict swine, which combination vaccine has a first component comprising an immunologically effective amount of one or more antigens of the present invention selected from the group consisting of an APP protein, homologous polypeptide, peptide fragment, fusion protein, analog, derivative, or polynucleotide molecule of the present invention capable of inducing, or contributing to the induction of, a protective response against APP in swine; a second component comprising an immunologically effective amount of a different antigen capable of inducing, or contributing to the induction of, a protective response against a disease or pathological condition that can afflict swine; and a veterinarily acceptable carrier or diluent.

The present invention further provides a method of preparing a vaccine that can protect swine against APP, comprising combining an immunologically effective amount of one or more antigens of the present invention selected from the group consisting of an APP protein, homologous polypeptide, peptide fragment, fusion protein, analog, derivative, or polynucleotide molecule of the present invention capable of inducing, or contributing to the induction of, a protective response against APP in swine, with a veterinarily acceptable carrier or diluent, in a form suitable for administration to swine.

The present invention further provides a method of vaccinating swine against APP, comprising administering a vaccine of the present invention to a pig.

The present invention further provides a vaccine kit for vaccinating swine against APP, comprising a container comprising an immunologically effective amount of one or more antigens of the present invention selected from the group consisting of an APP protein, homologous polypeptide, peptide fragment, fusion protein, analog, derivative, or polynucleotide molecule of the present invention capable of inducing, or contributing to the induction of, a protective response against APP in swine. The kit can further comprise a second container comprising a veterinarily acceptable carrier or diluent.

The present invention further provides antibodies that specifically bind to an APP protein of the present invention.

The present invention further provides diagnostic kits. In a non-limiting embodiment, the diagnostic kit comprises a first container comprising an APP protein, homologous polypeptide, peptide fragment, fusion protein, analog, or derivative of the present invention that will specifically bind to porcine antibodies directed against an APP protein; and a second container comprising a secondary antibody directed against the porcine anti-APP antibodies. The secondary antibody preferably comprises a detectable label. Such a diagnostic kit is useful to detect pigs that currently are, or have previously been, infected with APP, or that have seroconverted as a result of vaccination with a vaccine of the present invention. In a different non-limiting embodiment, the diagnostic kit comprises a first container comprising a primary antibody that binds to an APP protein of the present invention; and a second container comprising a secondary antibody that binds to a different epitope on the APP protein, or that binds to the primary antibody. The secondary antibody preferably comprises a detectable label. In a different non-limiting embodiment, the diagnostic kit comprises a container comprising a polynucleotide molecule or oligonucleotide molecule of the present invention that is useful to specifically amplify an APP-specific polynucleotide molecule of the present invention. These latter two diagnostic kits are useful to detect pigs that are currently infected with APP.

4. BRIEF DESCRIPTION OF THE DRAWINGS

FIGS. 1A&B. Western blot analysis of antibodies present in 1(a) serum, and 1(b) bronchial lymph node (BLN) tissue explant supernatants from pig No. 803 challenged with APP serotype-5 and heterologously rechallenged with APP serotype-7. All BLN tissue explant supernatants collected after 24 or 48 hr of incubation contained antibodies that specifically recognized APP proteins. The antibodies from the BLN tissue explant supernatants highlighted several low molecular weight proteins present in APP serotypes-1, 5, and 7.

Figure 2:
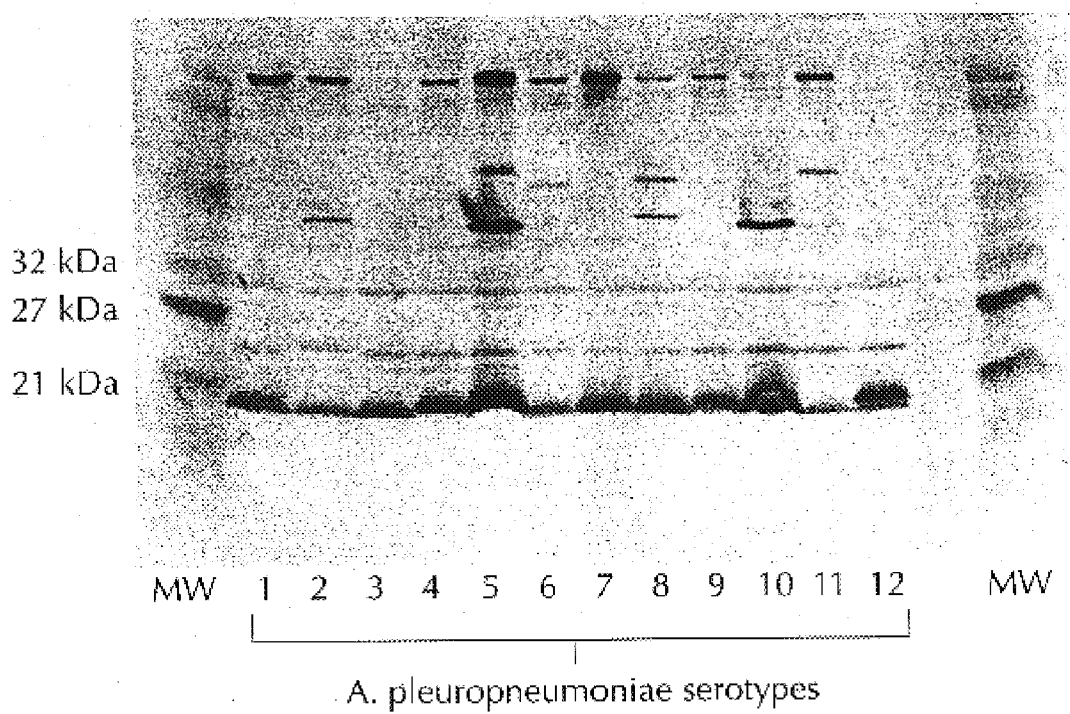

FIG. 2. Western blot analysis of cross-reactivity of antibodies present in BLN tissue explant supernatants from pig No. 803 against whole bacterial cell antigens from each of the twelve different APP serotypes, demonstrating that at least three of the low molecular weight proteins recognized by antibodies induced by heterologous rechallenge were present in all twelve APP serotypes. Antibodies present in this particular BLN supernatant also recognized other protein bands.

Figure 3:
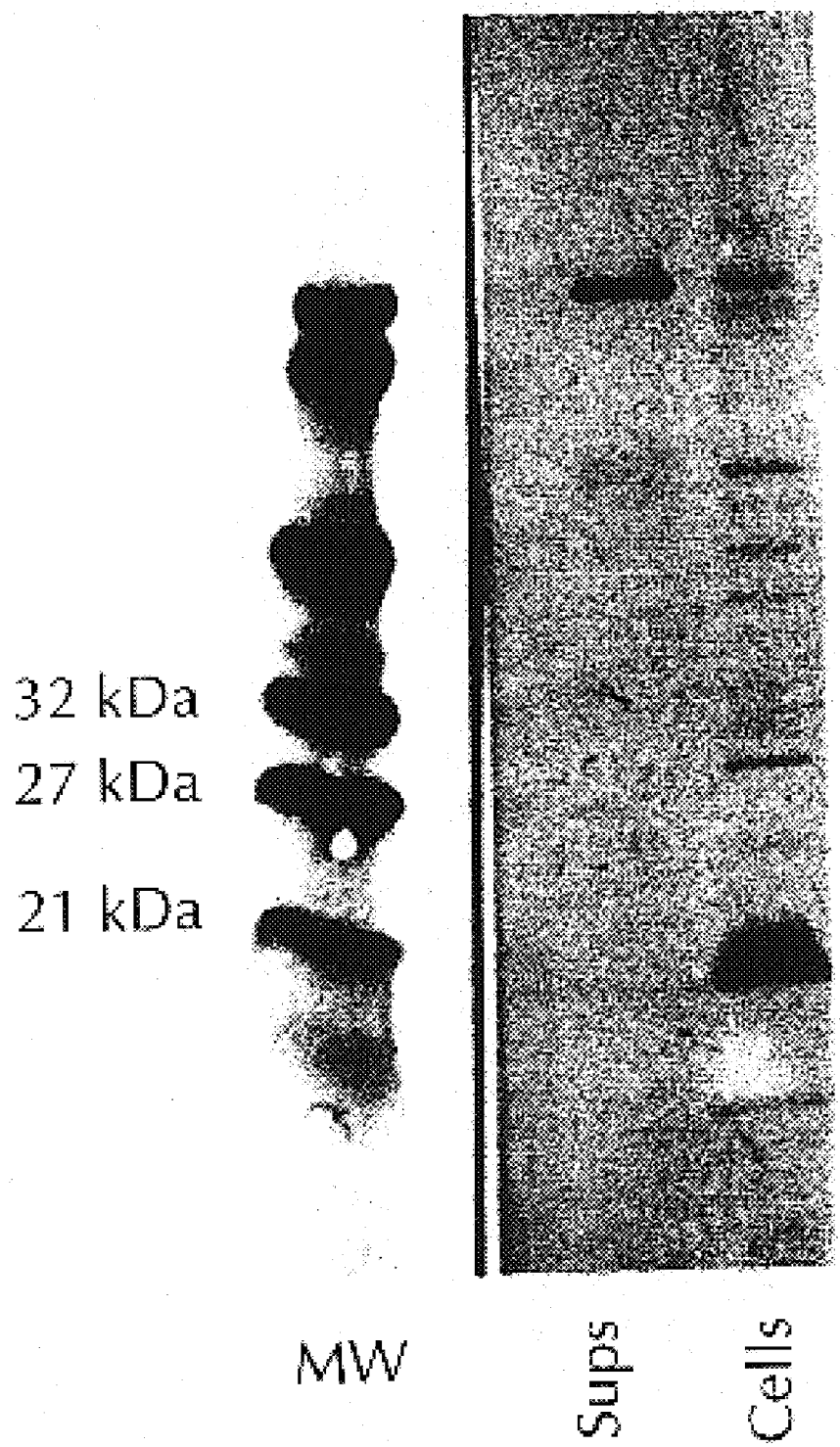

FIG. 3. Western blot analysis demonstrating that reactivity of antibodies in BLN tissue explant supernatants from pig No. 803 against the low molecular weight proteins is restricted to proteins present in the cell pellets (cells) rather than bacterial cell supernatants and 4(b) serum from pig No. 803, against proteins purified from APP serotype-7 by continuous flow electrophoresis. Four protein bands with molecular weights of about 19–20, about 23, about 27, and about 29 kDa, respectively, were identified using this procedure.

FIG. 5. Alignment of deduced amino acid sequences of APP OmpA1 (SEQ ID NO:8) and APP OmpA2 (SEQ ID NO:10) proteins. The two proteins share 73.1% amino acid identity.

FIG. 6. Alignment of OmpW protein from *Vibrio cholerae* and OmpW (SEQ ID NO:4) protein from APP. The two proteins share 44.9% amino acid identity.

5. DETAILED DESCRIPTION OF THE INVENTION

5.1. Novel Proteins Shared by Multiple APP Serotypes

The present invention is based on the discovery of five novel, low molecular weight proteins from APP (referred hereinafter as "APP proteins"). These APP proteins are designated herein, respectively, as "Omp20," "OmpW," "Omp27," "OmpA1," and "OmpA2."

The amino acid sequence of Omp20 is encoded by the Omp20-encoding ORF of plasmid pER416 which is present in host cells of strain Pz416 (ATCC 98926). The deduced amino acid sequence of Omp20 is presented as SEQ ID NO:2. The first 19 amino acids of the protein shown in SEQ ID NO:2 represent a signal sequence, and the present invention encompasses both an Omp20 protein having only amino acid residues 20 to 172 of SEQ ID NO:2 (i.e., lacking the signal sequence), and an Omp20 protein having the sequence of SEQ ID NO:2 (i.e., including the signal sequence). The present invention thus provides a substantially purified protein comprising the amino acid sequence of amino acid residue 20 to amino acid residue 172 of SEQ ID NO:2. The present invention further provides a substantially purified protein comprising the amino acid sequence of SEQ ID NO:2.

The amino acid sequence of OmpW is encoded by the OmpW-encoding ORF of plasmid pER418 which is present in host cells of strain Pz418 (ATCC 98928). The deduced amino acid sequence of OmpW is presented as SEQ ID NO:4. The first 21 amino acids of the protein shown in SEQ ID NO:4 represent a signal sequence, and the present invention encompasses both an OmpW protein having only amino acid residues 22 to 215 of SEQ ID NO:4 (i.e., lacking the signal sequence), and an OmpW protein having the sequence of SEQ ID NO:4 (i.e., including the signal sequence). The present invention thus provides a substantially purified protein comprising the amino acid sequence of amino acid residue 22 to amino acid residue 215 of SEQ ID NO:4. The present invention further provides a substantially purified protein comprising the amino acid sequence of SEQ ID NO:4.

The amino acid sequence of Omp27 is encoded by the Omp27-encoding ORF of plasmid pER417 which is present in host cells of strain Pz417 (ATCC 98927). The deduced amino acid sequence of Omp27 is presented as SEQ ID NO:6. The first 27 amino acids of the protein shown in SEQ ID NO:6 represent a signal sequence, and the present invention encompasses both an Omp27 protein having only amino acid residues 28 to 258 of SEQ ID NO:6 (i.e., lacking the signal sequence), and an Omp27 protein having the sequence of SEQ ID NO:6 (i.e., including the signal sequence). The present invention thus provides a substantially purified protein comprising the amino acid sequence of amino acid residue 28 to amino acid residue 258 of SEQ ID NO:6. The present invention further provides a substantially purified protein comprising the amino acid sequence of SEQ ID NO:6.

The amino acid sequence of OmpA1 is encoded by the OmpA1-encoding ORF of plasmid pER419 which is present in host cells of strain Pz419 (ATCC 98929). The deduced amino acid sequence of OmpA1 is presented as SEQ ID NO:8. The first 19 amino acids of the protein shown in SEQ ID NO:8 represent a signal sequence, and the present invention encompasses both an OmpA1 protein having only amino acid residues 20 to 364 of SEQ ID NO:8 (i.e., lacking the signal sequence), and an OmpA1 protein having the sequence of SEQ ID NO:8 (i.e., including the signal sequence). The present invention thus provides a substantially purified protein comprising the amino acid sequence of amino acid residue 20 to amino acid residue 364 of SEQ ID NO:8. The present invention further provides a substantially purified protein comprising the amino acid sequence of SEQ ID NO:8.

The amino acid sequence of OmpA2 is encoded by the OmpA2-encoding ORF of plasmid pER420 which is present in host cells of strain Pz420 (ATCC 98930). The deduced amino acid sequence of OmpA2 is presented as SEQ ID NO:10. The first 19 amino acids of the protein shown in SEQ ID NO:10 represent a signal sequence, and the present invention encompasses both an OmpA2 protein having only amino acid residues 20 to 369 of SEQ ID NO:10 (i.e., lacking the signal sequence), and an OmpA2 protein having the sequence of SEQ ID NO:10 (i.e., including the signal sequence). The present invention thus provides a substantially purified protein comprising the amino acid sequence of amino acid residue 20 to amino acid residue 369 of SEQ ID NO:10. The present invention further provides a substantially purified protein comprising the amino acid sequence of SEQ ID NO:10.

The APP proteins of the present invention, i.e., Omp20, OmpW, Omp27, OmpA1, and OmpA2, have molecular weights of about 19–20, about 23, about 27, about 29 and about 29 kDa, respectively, as based on their electrophoretic mobility; and about 20, about 23, about 27, about 35 and about 35 kDa, respectively, as based on their deduced amino acid sequences without signal sequences.

The present invention further provides polypeptides that are homologous to an APP protein of the present invention. As used herein to refer to polypeptides, the term "homologous" refers to a polypeptide otherwise having an amino acid sequence selected from the group of amino acid sequences consisting of SEQ ID NOS: 2, 4, 6, 8, and 10, or those same amino acid sequences but without their native signal sequences, in which one or more amino acid residues have been conservatively substituted with a different amino acid residue, wherein the homologous polypeptide has an amino acid sequence that has about 70%, more preferably about 80%, and most preferably about 90% sequence identity, as determined by any standard amino acid sequence analysis algorithm (such as one of the BlastP algorithms of GENBANK), to a polypeptide having an amino acid sequence selected from the group of amino acid sequences consisting of SEQ ID NOS: 2, 4, 6, 8, and 10, and wherein the resulting homologous polypeptide is useful in practicing the present invention. Conservative amino acid substitutions are well-known in the art. Rules for making such substitutions include those described by Dayhof, M. D., 1978, Nat. Biomed. Res. Found., Washington, D.C., Vol. 5, Sup. 3, among others. More specifically, conservative amino acid substitutions are those that generally take place within a family of amino acids that are related in acidity or polarity. Genetically encoded amino acids are generally divided into four groups: (1) acidic=aspartate, glutamate; (2) basic= lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. One or more replacements within any particular group, e.g., of a leucine with an isoleucine or valine, or of an aspartate with a glutamate, or of a threonine with a serine, or of any other amino acid residue with a structurally related amino acid residue, e.g., an amino acid residue with similar acidity, polarity, or with similarity in some combination thereof, will generally have an insignificant effect on the function or immunogenicity of the polypeptide.

As used herein, a polypeptide is "useful in practicing the present invention" where the polypeptide: (a) is immunogenic, i.e., can be used in a vaccine composition, either alone to induce a protective response in swine against *APP*, or in combination with other antigens of the present invention to contribute to the induction of a protective response in swine against *APP*; or (b) can be used to induce the production of *APP*-specific antibodies when administered to a member of a mammalian species, which antibodies are useful as diagnostic reagents; or (c) can be used as a diagnostic reagent to detect the presence of anti-*APP* antibodies in a blood or serum sample from a pig resulting either from infection with *APP* or vaccination with a vaccine of the present invention.

The present invention further provides peptide fragments of an *APP* protein or homologous polypeptide of the present invention. As used herein, a "peptide fragment" means a polypeptide consisting of less than the complete amino acid sequence of the corresponding full-length *APP* protein, either with or without signal sequence, or homologous polypeptide thereof, but comprising a sub-sequence of at least about 10, more preferably at least about 20, and most preferably at least about 30 amino acid residues of the amino acid sequence thereof, and that is useful in practicing the present invention, as usefulness is defined above for polypeptides. A peptide fragment of the present invention can comprise more than one sub-sequence of a full-length *APP* protein or homologous polypeptide of the present invention. For example, two or more different sub-sequences from the full-length *APP* protein or homologous polypeptide can be brought together and made contiguous to each other in the peptide fragment where they were non-contiguous in the *APP* protein or homologous polypeptide. In a preferred embodiment, a peptide fragment of the present invention comprises one or more sub-sequences representing one or more epitopes of the *APP* protein or homologous polypeptide, or multiple copies of an epitope, against which antibodies can be raised.

In a non-limiting embodiment, the present invention provides a peptide fragment of an *APP* protein of the present invention, which peptide fragment comprises the native signal sequence of the *APP* protein. In a preferred embodiment, the peptide fragment consists of an amino acid sequence selected from the group consisting of amino acid residue 1 to amino acid residue 19 of SEQ ID NO:2 (Omp20), amino acid residue 1 to amino acid residue 21 of SEQ ID NO:4 (OmpW), amino acid residue 1 to amino acid residue 27 of SEQ ID NO:6 (Omp27), amino acid residue 1 to amino acid residue 19 of SEQ ID NO:8 (OmpA1), and amino acid residue 1 to amino acid residue 19 of SEQ ID NO:10 (OmpA1). Such signal sequences, and the polynucleotide molecules that encode them, are useful for a variety of purposes, including to direct the cellular trafficking of recombinant proteins expressed in *APP* or other bacterial host cells, or as diagnostic probes for detecting an *APP*-specific polynucleotide molecule in a fluid or tissue sample from an infected animal.

The present invention further provides full-length *APP* proteins or homologous polypeptides in which sub-sequences thereof are arranged in a different relative order to each other compared to that found in the native molecule so as to increase, alter, or otherwise improve the antigenicity of the polypeptide.

As used herein, the terms "antigen," "antigenic," and the like, refer to a molecule containing one or more epitopes that stimulate a host's immune system to make a humoral and/or cellular antigen-specific response. The term is also used interchangeably with "immunogen." As used herein, the term "epitope" or "epitopic region" refers to a site on an antigen or hapten to which a specific antibody molecule binds. The term is also used interchangeably with "antigenic determinant."

The present invention further provides fusion proteins comprising an *APP* protein partner with or without its native signal sequence, a homologous polypeptide thereof, or a peptide fragment of the present invention, joined to a carrier or fusion partner, which fusion proteins are useful in practicing the present invention, as usefulness is defined above for polypeptides. See Section 5.4.1 below for examples of fusion partners. Fusion proteins are useful for a variety of reasons, including to increase the stability of recombinantly-expressed *APP* proteins, as antigenic components in an *APP* vaccine, to raise antisera against the particular *APP* protein partner, to study the biochemical properties of the *APP* protein partner, to engineer *APP* proteins with different or enhanced antigenic properties, to serve as diagnostic reagents, or to aid in the identification or purification of the expressed *APP* protein partner as described, e.g., in Section 5.4.1 below.

Fusion proteins of the present invention can be further engineered using standard techniques to contain specific protease cleavage sites so that the particular *APP* protein partner can be released from the carrier or fusion partner by treatment with a specific protease. For example, a fusion protein of the present invention can comprise a thrombin or factor Xa cleavage site, among others.

The present invention further provides analogs and derivatives of an *APP* protein, homologous polypeptide, peptide fragment or fusion protein of the present invention, where such analogs and derivatives are useful in practicing the present invention, as usefulness is defined above for polypeptides. Manipulations that result in the production of analogs can be carried out either at the gene level or at the protein level, or both, to improve or otherwise alter the biological or immunological characteristics of the particular polypeptide from which the analog is prepared. For example, at the gene level, a cloned DNA molecule encoding an *APP* protein of the present invention can be modified by one or more known strategies to encode an analog of that protein. Such modifications include, but are not limited to, endonuclease digestion, and mutations that create or destroy translation, initiation or termination sequences, or that create variations in the coding region, or a combination thereof. Such techniques are described, among other places, in Maniatis et al., 1989, *Molecular Cloning, A Laboratory Manual*, Cold Spring Harbor Laboratory Press, Cold Spring Harbor, N.Y.; Ausubel et al., 1989, *Current Protocols In Molecular Biology*, Greene Publishing Associates & Wiley Interscience, NY; Sambrook et al., 1989, *Molecular Cloning: A Laboratory Manual*, 2d ed., Cold Spring Harbor Laboratory Press, Cold Spring Harbor, N.Y.; Innis et al. (eds), 1995, *PCR Strategies*, Academic Press, Inc., San Diego; and Erlich (ed), 1992, *PCR Technology*, Oxford University Press, New York, all of which are incorporated herein by reference.

Alternatively or additionally, an analog of the present invention can be prepared by modification of an *APP* protein or other polypeptide of the present invention at the protein level. One or more chemical modifications of the protein can be carried out using known techniques, including but not limited to one or more of the following: substitution of one or more L-amino acids of the protein with corresponding D-amino acids, amino acid analogs, or amino acid mimics, so as to produce, e.g., carbazates or tertiary centers; or specific chemical modification, such as proteolytic cleavage with, e.g., trypsin, chymotrypsin, papain or V8 protease, or treatment with $NaBH_4$ or cyanogen bromide, or acetylation, formylation, oxidation or reduction, etc.

An *APP* protein or other polypeptide of the present invention can be derivatized by conjugation thereto of one or more chemical groups, including but not limited to acetyl groups, sulfur bridging groups, glycosyl groups, lipids, and phosphates, and/or a second *APP* protein or other polypeptide of the present invention, or another protein, such as, e.g., serum albumin, keyhole limpet hemocyanin, or commercially activated BSA, or a polyamino acid (e.g., polylysine), or a polysaccharide, (e.g., sepharose, agarose, or modified or unmodified celluloses), among others. Such conjugation is preferably by covalent linkage at amino acid side chains and/or at the N-terminus or C-terminus of the *APP* protein. Methods for carrying out such conjugation reactions are well-known in the field of protein chemistry.

Derivatives useful in practicing the claimed invention also include those in which a water-soluble polymer, such as, e.g., polyethylene glycol, is conjugated to an *APP* protein or other polypeptide of the present invention, or to an analog thereof, thereby providing additional desirable properties while retaining, at least in part, or improving the immunogenicity of the *APP* protein. These additional desirable properties include, e.g., increased solubility in aqueous solutions, increased stability in storage, increased resistance to proteolytic degradation, and increased in vivo half-life. Water-soluble polymers suitable for conjugation to an *APP* protein or other polypeptide of the present invention include but are not limited to polyethylene glycol homopolymers, polypropylene glycol homopolymers, copolymers of ethylene glycol with propylene glycol, wherein said homopolymers and copolymers are unsubstituted or substituted at one end with an alkyl group, polyoxyethylated polyols, polyvinyl alcohol, polysaccharides, polyvinyl ethyl ethers, and α,β-poly[2-hydroxyethyl]-DL-aspartamide. Polyethylene glycol is particularly preferred. Methods for making water-soluble polymer conjugates of polypeptides are known in the art and are described in, among other places, U.S. Pat. No. 3,788,948; U.S. Pat. No. 3,960,830; U.S. Pat. No. 4,002,531; U.S. Pat. No. 4,055,635; U.S. Pat. No. 4,179,337; U.S. Pat. No. 4,261,973; U.S. Pat. No. 4,412,989; U.S. Pat. No. 4,414,147; U.S. Pat. No. 4,415,665; U.S. Pat. No. 4,609,546; U.S. Pat. No. 4,732,863; U.S. Pat. No. 4,745,180; European Patent (EP) 152,847; EP 98,110; and Japanese Patent (JP) 5,792,435, which patents are incorporated herein by reference.

All subsequent references to "*APP* proteins" and the like are intended to include the *APP* proteins, homologous polypeptides, peptide fragments, fusion proteins, analogs, and derivatives of the present invention, as these terms are defined above, unless otherwise indicated.

5.2. Polynucleotide Molecules Encoding Novel *APP* Proteins

The present invention further provides isolated polynucleotide molecules comprising a nucleotide sequence encoding an *APP* protein. As used herein, the terms "polynucleotide molecule," "polynucleotide sequence," "coding sequence," "open-reading frame (ORF)," and the like, are intended to refer to both DNA and RNA molecules, which can either be single-stranded or double-stranded; that can include one or more prokaryotic sequences, cDNA sequences, genomic DNA sequences (including exons and introns), or chemically synthesized DNA and RNA sequences; and that can include both sense and anti-sense strands. As used herein, the term "ORF" refers to the minimal nucleotide sequence required to encode a particular *APP* protein of the present invention without any intervening termination codons. The boundaries of the polynucleotide coding sequence are generally determined by the presence of a start codon at the 5' (amino) terminus and a translation stop codon at the 3' (carboxy) terminus.

Production and manipulation of the polynucleotide molecules and oligonucleotide molecules disclosed herein below are within the skill in the art and can be carried out according to recombinant techniques described, among other places, in Maniatis et al., 1989, above; Ausubel et al., 1989, above; Sambrook et al., 1989, above; Innis et al., 1995, above; and Erlich, 1992, above.

5.2.1. Polynucleotide Molecules Encoding Omp20

References herein below to nucleotide sequences from SEQ ID NO:1, and to selected and substantial portions thereof, are intended to also refer to the corresponding Omp20-related nucleotide sequences of plasmid pER416 which is present in host cells of strain Pz416 (ATCC 98926), unless otherwise indicated. In addition, references herein below to the amino acid sequences shown in SEQ ID NO:2, and to peptide fragments thereof, are intended to also refer to the corresponding amino acid sequences encoded by the Omp20-related nucleotide sequence of plasmid pER416, unless otherwise indicated.

The present invention provides an isolated polynucleotide molecule comprising a nucleotide sequence encoding the *APP* protein, Omp20, with or without signal sequence. In a preferred embodiment, the isolated Omp20-encoding polynucleotide molecule of the present invention comprises the nucleotide sequence of SEQ ID NO:1 from nt 329 to nt 790. In a more preferred embodiment, the isolated Omp20-encoding polynucleotide molecule of the present invention comprises the nucleotide sequence of SEQ ID NO:1 from nt 272 to nt 790. In a non-limiting embodiment, the isolated Omp20-encoding polynucleotide molecule of the present invention comprises the nucleotide sequence of SEQ ID NO:1.

The present invention further provides an isolated polynucleotide molecule that is homologous to an *APP* Omp20-encoding polynucleotide molecule of the present invention. The term "homologous" when used to refer to an Omp20-encoding polynucleotide molecule means a polynucleotide molecule having a nucleotide sequence: (a) that encodes the same amino acid sequence as the nucleotide sequence of SEQ ID NO:1 from nt 329 to nt 790, but that includes one or more silent changes to the nucleotide sequence according to the degeneracy of the genetic code; or (b) that hybridizes to the complement of a polynucleotide molecule having a nucleotide sequence that encodes amino acid residues 20 to 172 of SEQ ID NO:2 under moderately stringent conditions, ie., hybridization to filter-bound DNA in 0.5 M NaHPO$_4$, 7% sodium dodecyl sulfate (SDS), 1 mM EDTA at 65° C., and washing in 0.2×SSC/0.1% SDS at 42° C. (see Ausubel et al. (eds.), 1989, *Current Protocols in Molecular Biology*, Vol. I, Green Publishing Associates, Inc., and John Wiley & Sons, Inc., New York, at p. 2.10.3), and that is useful in practicing the present invention. In a preferred embodiment, the homologous polynucleotide molecule hybridizes to the complement of a polynucleotide molecule having a nucleotide sequence that encodes amino acid residues 20 to 172 of SEQ ID NO:2 under highly stringent conditions, i.e., hybridization to filter-bound DNA in 0.5 M NaHPO$_4$, 7% SDS, 1 mM EDTA at 65° C., and washing in 0.1×SSC/0.1% SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of the nucleotide sequence of SEQ ID NO:1 from nt 329 to nt 790, and is useful in practicing the present invention.

As used herein, a polynucleotide molecule is "useful in practicing the present invention" where: (a) the polynucleotide molecule encodes a polypeptide which can be used in a vaccine composition either to induce by itself, or to contribute in combination with one or more other antigens to the induction of, a protective response in swine against *APP*; or (b) the polynucleotide molecule can be used directly in a DNA vaccine composition to induce by itself, or to contribute in combination with one or more other polynucleotide molecules or one or more other antigens to the induction of, a protective response in swine against *APP*; or (c) the polynucleotide molecule encodes a polypeptide that can be used to induce the production of *APP*-specific antibodies when administered to a member of a mammalian species, which antibodies are useful as diagnostic reagents; or (d) the polynucleotide molecule encodes a polypeptide that can be used as a diagnostic reagent to detect the presence of *APP*-specific antibodies in a blood or serum sample from a pig; or (e) the polynucleotide molecule can be used as a diagnostic reagent to detect the presence of an *APP*-specific polynucleotide molecule in a fluid or tissue sample from an *APP*-infected pig.

The present invention further provides an isolated polynucleotide molecule comprising a nucleotide sequence that encodes a polypeptide that is homologous to the Omp20 protein of the present invention, as "homologous polypeptides" are defined above in Section 5.1.

The present invention further provides a polynucleotide molecule consisting of a nucleotide sequence that is a substantial portion of any of the aforementioned Omp20-related polynucleotide molecules of the present invention. As used herein, a "substantial portion" of an Omp20-related polynucleotide molecules means a polynucleotide molecule consisting of less than the complete nucleotide sequence of the particular full-length Omp20-related polynucleotide molecule, but comprising at least about 10%, and more preferably at least about 20%, of the nucleotide sequence of the particular full-length Omp20-related polynucleotide molecule, and that is useful in practicing the present invention, as "usefulness" is defined above for polynucleotide molecules. In a non-limiting embodiment, the substantial portion of the Omp20-related polynucleotide molecule encodes a peptide fragment of any of the aforementioned Omp20-related proteins or polypeptides of the present invention, as the term "peptide fragment" is defined above.

The present invention further provides a polynucleotide molecule comprising a nucleotide sequence, which encodes the native Omp20 signal sequence from amino acid residue 1 to amino acid residue 19 of SEQ ID NO:2. In a preferred though non-limiting embodiment, the Omp20 signal sequence-encoding polynucleotide molecule comprises from nt 272 to nt 328 of SEQ ID NO:1.

The present invention further provides a polynucleotide molecule comprising a nucleotide sequence that encodes a fusion protein comprising the Omp20 protein, homologous polypeptide, or peptide fragment, fused to a carrier or fusion partner.

5.2.2. Polynucleotide Molecules Encoding OmpW

References herein below to nucleotide sequences from SEQ ID NO:3, and to selected and substantial portions thereof, are intended to also refer to the corresponding OmpW-related nucleotide sequences of plasmid pER418 which is present in host cells of strain Pz418 (ATCC 98928), unless otherwise indicated. In addition, references herein below to the amino acid sequences shown in SEQ ID NO:4, and to peptide fragments thereof, are intended to also refer to the corresponding amino acid sequences encoded by the OmpW-related nucleotide sequence of plasmid pER418, unless otherwise indicated.

The present invention provides an isolated polynucleotide molecule comprising a nucleotide sequence encoding the *APP* protein, OmpW, with or without signal sequence. In a preferred embodiment, the isolated OmpW-encoding polynucleotide molecule of the present invention comprises the nucleotide sequence of SEQ ID NO:3 from nt 439 to nt 1023. In a more preferred embodiment, the isolated OmpW-encoding polynucleotide molecule of the present invention comprises the nucleotide sequence of SEQ ID NO:3 from nt 376 to nt 1023. In a non-limiting embodiment, the isolated OmpW-encoding polynucleotide molecule of the present invention comprises the nucleotide sequence of SEQ ID NO:3.

The present invention further provides an isolated polynucleotide molecule that is homologous to an *APP* OmpW-encoding polynucleotide molecule of the present invention. The term "homologous" when used to refer to an OmpW-encoding polynucleotide molecule means a polynucleotide molecule having a nucleotide sequence: (a) that encodes the same amino acid sequence as the nucleotide sequence of SEQ ID NO:3 from nt 439 to nt 1023, but that includes one or more silent changes to the nucleotide sequence according to the degeneracy of the genetic code; or (b) that hybridizes to the complement of a polynucleotide molecule having a nucleotide sequence that encodes amino acid residues 22 to 215 of SEQ ID NO:4 under moderately stringent conditions, i.e., hybridization to filter-bound DNA in 0.5 M $NaHPO_4$, 7% SDS, 1 mM EDTA at 65° C., and washing in 0.2×SSC/ 0.1% SDS at 42° C. (Ausubel et al., 1989, above), and that is useful in practicing the present invention, as "usefulness" is defined above for polynucleotide molecules. In a preferred embodiment, the homologous polynucleotide molecule hybridizes to the complement of a polynucleotide molecule having a nucleotide sequence that encodes amino acid residues 22 to 215 of SEQ ID NO:4 under highly stringent conditions, i.e., hybridization to filter-bound DNA in 0.5 M $NaHPO_4$, 7% SDS, 1 mM EDTA at 65° C., and washing in 0.1×SSC/0.1% SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of the nucleotide sequence of SEQ ID NO:3 from nt 439 to nt 1023, and is useful in practicing the present invention.

The present invention further provides an isolated polynucleotide molecule comprising a nucleotide sequence that encodes a polypeptide that is homologous to the OmpW protein of the present invention, as "homologous polypeptide" is defined above.

The present invention further provides a polynucleotide molecule consisting of a nucleotide sequence that is a substantial portion of any of the aforementioned OmpW-related polynucleotide molecules of the present invention. As used herein, a "substantial portion" of an OmpW-related polynucleotide molecules means a polynucleotide molecule consisting of less than the complete nucleotide sequence of the particular full-length OmpW-related polynucleotide molecule, but comprising at least about 10%, and more preferably at least about 20%, of the nucleotide sequence of the particular full-length OmpW-related polynucleotide molecule, and that is useful in practicing the present invention, as "usefulness" is defined above for polynucleotide molecules. In a non-limiting embodiment, the substantial portion of the OmpW-related polynucleotide molecule encodes a peptide fragment of any of the aforementioned OmpW-related proteins or polypeptides of the present invention, as the term "peptide fragment" is defined above.

The present invention further provides a polynucleotide molecule comprising a nucleotide sequence, which encodes the native OmpW signal sequence from amino acid residue 1 to amino acid residue 21 of SEQ ID NO:4. In a preferred though non-limiting embodiment, the OmpW signal sequence-encoding polynucleotide molecule comprises from nt 376 to nt 438 of SEQ ID NO:3.

The present invention further provides a polynucleotide molecule comprising a nucleotide sequence that encodes a fusion protein comprising the OmpW protein, homologous polypeptide, or peptide fragment, fused to a carrier or fusion partner.

5.2.3. Polynucleotide Molecules Encoding Omp27

References herein below to nucleotide sequences from SEQ ID NO:5, and to selected and substantial portions thereof, are intended to also refer to the corresponding Omp27-related nucleotide sequences of plasmid pER417 which is present in host cells of strain Pz417 (ATCC 98927), unless otherwise indicated. In addition, references herein below to the amino acid sequences shown in SEQ ID NO:6, and to peptide fragments thereof, are intended to also refer to the corresponding amino acid sequences encoded by the Omp27-related nucleotide sequence of plasmid pER417, unless otherwise indicated.

The present invention provides an isolated polynucleotide molecule comprising a nucleotide sequence encoding the *APP* protein, Omp27, with or without signal sequence. In a preferred embodiment, the isolated Omp27-encoding polynucleotide molecule of the present invention comprises the nucleotide sequence of SEQ ID NO:5 from nt 238 to nt 933. In a more preferred embodiment, the isolated Omp27-encoding polynucleotide molecule of the present invention comprises the nucleotide sequence of SEQ ID NO:5 from nt 157 to nt 933. In a non-limiting embodiment, the isolated Omp27-encoding polynucleotide molecule of the present invention comprises the nucleotide sequence of SEQ ID NO:5.

The present invention further provides an isolated polynucleotide molecule that is homologous to an *APP* Omp27-encoding polynucleotide molecule of the present invention. The term "homologous" when used to refer to an Omp27-encoding polynucleotide molecule means a polynucleotide molecule having a nucleotide sequence: (a) that encodes the same amino acid sequence as the nucleotide sequence of SEQ ID NO:5 from nt 238 to nt 933, but that includes one or more silent changes to the nucleotide sequence according to the degeneracy of the genetic code; or (b) that hybridizes to the complement of a polynucleotide molecule having a nucleotide sequence that encodes amino acid residues 28 to 258 of SEQ ID NO:6 under moderately stringent conditions, i.e., hybridization to filter-bound DNA in 0.5 M NaHPO$_4$, 7% SDS, 1 mM EDTA at 65° C., and washing in 0.2×SSC/0.1% SDS at 42° C. (Ausubel et al., 1989, above), and that is useful in practicing the present invention, as "usefulness" is defined above for polynucleotide molecules. In a preferred embodiment, the homologous polynucleotide molecule hybridizes to the complement of a polynucleotide molecule having a nucleotide sequence that encodes amino acid residues 28 to 258 of SEQ ID NO:6 under highly stringent conditions, i.e., hybridization to filter-bound DNA in 0.5 M NaHPO$_4$, 7% SDS, 1 mM EDTA at 65° C., and washing in 0.1×SSC/0.1% SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of the nucleotide sequence of SEQ ID NO:5 from nt 238 to nt 933, and is useful in practicing the present invention.

The present invention further provides an isolated polynucleotide molecule comprising a nucleotide sequence that encodes a polypeptide that is homologous to the Omp27 protein of the present invention, as "homologous polypeptide" is defined above.

The present invention further provides a polynucleotide molecule consisting of a nucleotide sequence that is a substantial portion of any of the aforementioned Omp27-related polynucleotide molecules of the present invention. As used herein, a "substantial portion" of an Omp27-related polynucleotide molecules means a polynucleotide molecule consisting of less than the complete nucleotide sequence of the particular full-length Omp27-related polynucleotide molecule, but comprising at least about 10%, and more preferably at least about 20%, of the nucleotide sequence of the particular full-length Omp27-related polynucleotide molecule, and that is useful in practicing the present invention, as "usefulness" is defined above for polynucleotide molecules. In a non-limiting embodiment, the substantial portion of the Omp27-related polynucleotide molecule encodes a peptide fragment of any of the aforementioned Omp27-related proteins or polypeptides of the present invention, as the term "peptide fragment" is defined above.

The present invention further provides a polynucleotide molecule comprising a nucleotide sequence, which encodes the native Omp27 signal sequence from amino acid residue 1 to amino acid residue 27 of SEQ ID NO:6. In a preferred though non-limiting embodiment, the Omp27 signal sequence-encoding polynucleotide molecule comprises from nt 157 to nt 237 of SEQ ID NO:5.

The present invention further provides a polynucleotide molecule comprising a nucleotide sequence that encodes a fusion protein comprising the Omp27 protein, homologous polypeptide, or peptide fragment, fused to a carrier or fusion partner.

5.2.4. Polynucleotide Molecules Encoding OmpA1

References herein below to nucleotide sequences from SEQ ID NO:7, and to selected and substantial portions thereof, are intended to also refer to the corresponding OmpA1-related nucleotide sequences of plasmid pER419 which is present in host cells of strain Pz419 (ATCC 98929), unless otherwise indicated. In addition, references herein below to the amino acid sequences shown in SEQ ID NO:8, and to peptide fragments thereof, are intended to also refer to the corresponding amino acid sequences encoded by the OmpA1-related nucleotide sequence of plasmid pER419, unless otherwise indicated.

The present invention provides an isolated polynucleotide molecule comprising a nucleotide sequence encoding the *APP* protein, OmpA1, with or without signal sequence. In a preferred embodiment, the isolated OmpA1-encoding polynucleotide molecule of the present invention comprises the nucleotide sequence of SEQ ID NO:7 from nt 671 to nt 1708. In a more preferred embodiment, the isolated OmpA1-encoding polynucleotide molecule of the present invention comprises the nucleotide sequence of SEQ ID NO:7 from nt 614 to nt 1708. In a non-limiting embodiment, the isolated OmpA1-encoding polynucleotide molecule of the present invention comprises the nucleotide sequence of SEQ ID NO:7.

The present invention further provides an isolated polynucleotide molecule that is homologous to an *APP* OmpA1-encoding polynucleotide molecule of the present invention. The term "homologous" when used to refer to an OmpA1-encoding polynucleotide molecule means a polynucleotide molecule having a nucleotide sequence: (a) that encodes the same amino acid sequence as the nucleotide sequence of SEQ ID NO:7 from nt 671 to nt 1708, but that includes one or more silent changes to the nucleotide sequence according to the degeneracy of the genetic code; or (b) that hybridizes to the complement of a polynucleotide molecule having a nucleotide sequence that encodes amino acid residues 20 to 364 of SEQ ID NO:8 under moderately stringent conditions, i.e., hybridization to filter-bound DNA in 0.5 M NaHPO$_4$, 7% SDS, 1 mM EDTA at 65° C., and washing in 0.2×SSC/ 0.1% SDS at 42° C. (Ausubel et al., 1989, above), and that is useful in practicing the present invention, as "usefulness" is defined above for polynucleotide molecules. In a preferred embodiment, the homologous polynucleotide molecule hybridizes to the complement of a polynucleotide molecule having a nucleotide sequence that encodes amino acid residues 20 to 364 of SEQ ID NO:8 under highly stringent conditions, i.e., hybridization to filter-bound DNA in 0.5 M NaHPO$_4$, 7% SDS, 1 mM EDTA at 65° C., and washing in 0.1×SSC/0.1% SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of the nucleotide sequence of SEQ ID NO:7 from nt 671 to nt 1708, and is useful in practicing the present invention.

The present invention further provides an isolated polynucleotide molecule comprising a nucleotide sequence that encodes a polypeptide that is homologous to the OmpA1 protein of the present invention, as "homologous polypeptide" is defined above.

The present invention further provides a polynucleotide molecule consisting of a nucleotide sequence that is a substantial portion of any of the aforementioned OmpA1-related polynucleotide molecules of the present invention. As used herein, a "substantial portion" of an OmpA1-related polynucleotide molecules means a polynucleotide molecule consisting of less than the complete nucleotide sequence of the particular full-length OmpA1-related polynucleotide molecule, but comprising at least about 10%, and more preferably at least about 20%, of the nucleotide sequence of the particular full-length OmpA1-related polynucleotide molecule, and that is useful in practicing the present invention, as "usefulness" is defined above for polynucleotide molecules. In a non-limiting embodiment, the substantial portion of the OmpA1-related polynucleotide molecule encodes a peptide fragment of any of the aforementioned OmpA1-related polypeptides of the present invention, as the term "peptide fragment" is defined above.

The present invention further provides a polynucleotide molecule comprising a nucleotide sequence, which encodes the native OmpA1 signal sequence from amino acid residue 1 to amino acid residue 19 of SEQ ID NO:8. In a preferred though non-limiting embodiment, the OmpA1 signal sequence-encoding polynucleotide molecule comprises from nt 614 to nt 670 of SEQ ID NO:7.

The present invention further provides a polynucleotide molecule comprising a nucleotide sequence that encodes a fusion protein comprising the OmpA1 protein, homologous polypeptide, or peptide fragment, fused to a carrier or fusion partner.

5.2.5. Polynucleotide Molecules Encoding OmpA2

References herein below to nucleotide sequences from SEQ ID NO:9, and to selected and substantial portions thereof, are intended to also refer to the corresponding OmpA2-related nucleotide sequences of plasmid pER420 which is present in host cells of strain Pz420 (ATCC 98930), unless otherwise indicated. In addition, references herein below to the amino acid sequences shown in SEQ ID NO:10, and to peptide fragments thereof, are intended to also refer to the corresponding amino acid sequences encoded by the OmpA2-related nucleotide sequence of plasmid pER420, unless otherwise indicated.

The present invention provides an isolated polynucleotide molecule comprising a nucleotide sequence encoding the APP protein, OmpA2, with or without signal sequence. In a preferred embodiment, the isolated OmpA2-encoding polynucleotide molecule of the present invention comprises the nucleotide sequence of SEQ ID NO:9 from nt 254 to nt 1306. In a more preferred embodiment, the isolated OmpA2-encoding polynucleotide molecule of the present invention comprises the nucleotide sequence of SEQ ID NO:9 from nt 197 to nt 1306. In a non-limiting embodiment, the isolated OmpA2-encoding polynucleotide molecule of the present invention comprises the nucleotide sequence of SEQ ID NO:9.

The present invention further provides an isolated polynucleotide molecule that is homologous to an APP OmpA2-encoding polynucleotide molecule of the present invention. The term "homologous" when used to refer to an OmpA2-encoding polynucleotide molecule means a polynucleotide molecule having a nucleotide sequence: (a) that encodes the same amino acid sequence as the nucleotide sequence of SEQ ID NO:9 from nt 254 to nt 1306, but that includes one or more silent changes to the nucleotide sequence according to the degeneracy of the genetic code; or (b) that hybridizes to the complement of a polynucleotide molecule having a nucleotide sequence that encodes amino acid residues 20 to 369 of SEQ ID NO:10 under moderately stringent conditions, i.e., hybridization to filter-bound DNA in 0.5 M NaHPO$_4$, 7% SDS, 1 mM EDTA at 65° C., and washing in 0.2×SSC/0.1% SDS at 42° C. (Ausubel et al., 1989, above), and that is useful in practicing the present invention, as "usefulness" is defined above for polynucleotide molecules. In a preferred embodiment, the homologous polynucleotide molecule hybridizes to the complement of a polynucleotide molecule having a nucleotide sequence that encodes amino acid residues 20 to 369 of SEQ ID NO:10 under highly stringent conditions, i.e., hybridization to filter-bound DNA in 0.5 M NaHPO$_4$, 7% SDS, 1 mM EDTA at 65° C., and washing in 0.1×SSC/0.1% SDS at 68° C. (Ausubel et al., 1989, above), and is useful in practicing the present invention. In a more preferred embodiment, the homologous polynucleotide molecule hybridizes under highly stringent conditions to the complement of a polynucleotide molecule consisting of the nucleotide sequence of SEQ ID NO:9 from nt 254 to nt 1306, and is useful in practicing the present invention.

The present invention further provides an isolated polynucleotide molecule comprising a nucleotide sequence that encodes a polypeptide that is homologous to the OmpA2 protein of the present invention, as "homologous polypeptide" is defined above.

The present invention further provides a polynucleotide molecule consisting of a nucleotide sequence that is a substantial portion of any of the aforementioned OmpA2-related polynucleotide molecules of the present invention. As used herein, a "substantial portion" of an OmpA2-related polynucleotide molecules means a polynucleotide molecule consisting of less than the complete nucleotide sequence of the particular full-length OmpA2-related polynucleotide molecule, but comprising at least about 10%, and more preferably at least about 20%, of the nucleotide sequence of the particular full-length OmpA2-related polynucleotide molecule, and that is useful in practicing the present invention, as "usefulness" is defined above for polynucleotide molecules. In a non-limiting embodiment, the substantial portion of the OmpA2-related polynucleotide molecule encodes a peptide fragment of any of the aforementioned OmpA2-related polypeptides of the present invention, as the term "peptide fragment" is defined above.

The present invention further provides a polynucleotide molecule comprising a nucleotide sequence, which encodes the native OmpA2 signal sequence from amino acid residue 1 to amino acid residue 19 of SEQ ID NO:10. In a preferred though non-limiting embodiment, the OmpA2 signal sequence-encoding polynucleotide molecule comprises from nt 197 to nt 253 of SEQ ID NO:9.

The present invention further provides a polynucleotide molecule comprising a nucleotide sequence that encodes a fusion protein comprising the OmpA2 protein, homologous polypeptide, or peptide fragment, fused to a carrier or fusion partner.

5.3. Oligonucleotide Molecules

The present invention further provides oligonucleotide molecules that hybridize to any of the aforementioned polynucleotide molecules of the present invention, or that hybridize to a polynucleotide molecule having a nucleotide sequence that is the complement of any of the aforementioned polynucleotide molecules of the present invention. Such oligonucleotide molecules are preferably at least about 10 to 15 nucleotides in length, but can extend up to the length of any sub-sequence of SEQ ID NOS:1, 3, 5, 7 or 9, or homologous polynucleotide molecule thereof, and can hybridize to one or more of the aforementioned polynucleotide molecules under highly stringent conditions. For shorter oligonucleotide molecules, an example of highly stringent conditions includes washing in 6×SSC/0.5% sodium pyrophosphate at about 37° C. for ~14-base oligos, at about 48° C. for ~17-base oligos, at about 55° C. for ~20-base and at about 60° C. for ~23-base oligos. For longer oligonucleotide molecules (i.e., greater than about 100 nts), examples of highly stringent conditions are provided in Section 5.2 above. Other appropriate hybridization conditions can be determined and adjusted as known in the art, depending upon the particular oligonucleotide and polynucleotide molecules utilized.

In a preferred embodiment, an oligonucleotide molecule of the present invention hybridizes under highly stringent conditions to a polynucleotide molecule consisting of a nucleotide sequence selected from SEQ ID NOS:1, 3, 5, 7, or 9, or to a polynucleotide molecule consisting of a nucleotide sequence that is the complement of a nucleotide sequence selected from SEQ ID NOS:1, 3, 5, 7, or 9.

In a non-limiting embodiment, an oligonucleotide molecule of the present invention comprises a nucleotide sequence selected from the group consisting of SEQ ID NOS:15–47 and 49–93 and the complements of said sequences. In a non-limiting embodiment, the oligonucleotide molecule consists of a nucleotide sequence selected from the group consisting of SEQ ID NOS:15–47 and 49–93 and the complements of said sequences.

The oligonucleotide molecules of the present invention are useful for a variety of purposes, including as primers in amplification of an *APP* protein-encoding polynucleotide molecule for use, e.g., in differential disease diagnosis, or to encode or act as antisense molecules useful in gene regulation. Amplification can be used to detect the presence of a polynucleotide molecule encoding an *APP* protein in a tissue or fluid sample, e.g., in mucous or bronchial fluid, from an infected animal. The production of a specific amplification product can help support a diagnosis of *APP* bacterial infection, while lack of an amplified product can indicate a lack of such infection. The oligonucleotide molecules disclosed herein can also be used to isolate homologous genes from other species or strains of Actinobacillus, or from other bacteria.

Amplification can be carried out using suitably designed oligonucleotide molecules in conjunction with standard techniques, such as the polymerase chain reaction (PCR), although other amplification techniques known in the art, e.g., the ligase chain reaction, can be used. For example, for PCR, a mixture comprising suitably designed primers, a template comprising the nucleotide sequence to be amplified, and appropriate PCR enzymes and buffers as known in the art, is prepared and processed according to standard protocols to amplify a specific *APP*-related polynucleotide sequence of the template. Methods for conducting PCR are described, among other places, in Innis et al. (eds), 1995, above; and Erlich (ed), 1992, above.

5.4. Recombinant Expression Systems 5.4.1. Cloning and Expression Vectors

The present invention further provides compositions for cloning and expressing any of the polynucleotide molecules of the present invention, including recombinant cloning vectors and recombinant expression vectors comprising a polynucleotide molecule of the present invention, host cells transformed with any of said vectors, and cell lines derived therefrom. Recombinant vectors of the present invention, particularly expression vectors, are preferably constructed so that the coding sequence of the polynucleotide molecule (referred to hereinafter as the "*APP* coding sequence") is in operative association with one or more regulatory elements necessary for transcription and translation of the *APP* coding sequence to produce a polypeptide.

As used herein, the term "regulatory element" includes but is not limited to nucleotide sequences that encode inducible and non-inducible promoters, enhancers, operators and other elements known in the art that serve to drive and/or regulate expression of polynucleotide coding sequences. Also, as used herein, the *APP* coding sequence is in "operative association" with one or more regulatory elements where the regulatory elements effectively regulate and allow for the transcription of the coding sequence or the translation of its mRNA, or both.

Methods are well-known in the art for constructing recombinant vectors containing particular coding sequences in operative association with appropriate regulatory elements, including in vitro recombinant techniques, synthetic techniques, and in vivo genetic recombination. See, e.g., the techniques described in Maniatis et al., 1989, above; Ausubel et al., 1989, above; Sambrook et al., 1989, above; Innis et al., 1995, above; and Erlich, 1992, above.

A variety of expression vectors are known in the art that can be utilized to express any of the *APP* coding sequences of the present invention, including recombinant bacteriophage DNA, plasmid DNA, and cosmid DNA expression vectors containing an *APP* coding sequence. Typical prokaryotic expression vector plasmids that can be engineered to contain an *APP* coding sequence of the present invention include pUC8, pUC9, pBR322 and pBR329 (Biorad Laboratories, Richmond, Calif.), pPL and pKK223 (Pharmacia, Piscataway, N.J.), pQE50 (Qiagen, Chatsworth, Calif.), and pGEX series plasmids (Pharmacia), among many others. Typical eukaryotic expression vectors that can be engineered to contain an *APP* coding sequence of the present invention include an ecdysone-inducible mammalian expression system (Invitrogen, Carlsbad, Calif.), cytomegalovirus promoter-enhancer-based systems (Promega, Madison, Wis.; Stratagene, La Jolla, Calif.;

Invitrogen), baculovirus-based expression systems (Promega), and plant-based expression systems, among others.

The regulatory elements of these and other vectors can vary in their strength and specificities. Depending on the host/vector system utilized, any of a number of suitable transcription and translation elements can be used. For instance, when cloning in mammalian cell systems, promoters isolated from the genome of mammalian cells, e.g., mouse metallothionein promoter, or from viruses that grow in these cells, e.g., vaccinia virus 7.5K promoter or Moloney murine sarcoma virus long terminal repeat, can be used. Promoters obtained by recombinant DNA or synthetic techniques can also be used to provide for transcription of the inserted coding sequence. In addition, expression from certain promoters can be elevated in the presence of particular inducers, e.g., zinc and cadmium ions for metallothionein promoters. Non-limiting examples of transcriptional regulatory regions or promoters include for bacteria, the β-gal promoter, the T7 promoter, the TAC promoter, λ left and right promoters, trp and lac promoters, trp-lac fusion promoters, etc.; for yeast, glycolytic enzyme promoters, such as ADH-I and II promoters, GPK promoter, PGI promoter, TRP promoter, etc.; and for mammalian cells, SV40 early and late promoters, adenovirus major late promoters, among others.

Specific initiation signals are also required for sufficient translation of inserted coding sequences. These signals typically include an ATG initiation codon and adjacent sequences. In cases where the *APP* coding sequence of the present invention including its own initiation codon and adjacent sequences are inserted into the appropriate expression vector, no additional translation control signals are needed. However, in cases where only a portion of an *APP* coding sequence is inserted, exogenous translational control signals, including the ATG initiation codon, can be required. These exogenous translational control signals and initiation codons can be obtained from a variety of sources, both natural and synthetic. Furthermore, the initiation codon must be in phase with the reading frame of the coding regions to ensure in-frame translation of the entire insert.

Expression vectors can also be constructed that will express a fusion protein comprising any of the *APP*-related polypeptides of the present invention fused to a carrier or fusion partner. Such fusion proteins can be used for a variety of purposes, such as to increase the stability of a recombinantly-expressed *APP* protein, to raise antisera against an *APP* protein, to study the biochemical properties of an *APP* protein, to engineer an *APP* protein exhibiting altered immunological properties, or to aid in the identification or purification of a recombinantly-expressed *APP* protein. Possible fusion protein expression vectors include but are not limited to vectors incorporating sequences that encode a protective peptide, such as that described below in Section 8.2, as well as β-galactosidase and trpE fusions, maltose-binding protein fusions, glutathione-S-transferase (GST) fusions and polyhistidine fusions (carrier regions). Methods are well-known in the art that can be used to construct expression vectors encoding these and other fusion proteins.

Fusion proteins can be useful to aid in purification of the expressed protein. In non-limiting embodiments, e.g., an *APP* protein-maltose-binding fusion protein can be purified using amylose resin; an *APP* protein-GST fusion protein can be purified using glutathione-agarose beads; and an *APP* protein-polyhistidine fusion protein can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to an *APP* protein of the present invention. In a non-limiting embodiment, a nucleotide sequence coding for the FLAG™ epitope tag (International Biotechnologies Inc.), which is a hydrophilic marker peptide, can be inserted by standard techniques into the expression vector at a point corresponding to the amino or carboxyl terminus of the *APP* protein. The expressed polypeptide-FLAG™ epitope fusion product can then be detected and affinity-purified using commercially available anti-FLAG™ antibodies.

The expression vector of the present invention can also be engineered to contain polylinker sequences that encode specific protease cleavage sites so that the expressed *APP* protein can be released from the carrier region or fusion partner by treatment with a specific protease. For example, the fusion protein vector can include a nucleotide sequence encoding a thrombin or factor Xa cleavage site, among others.

A signal sequence upstream from and in reading frame with the *APP* coding sequence can be engineered into the expression vector by known methods to direct the trafficking and secretion of the expressed *APP* polypeptide. Non-limiting examples of signal sequences include those which are native to the *APP* proteins of the present invention as disclosed herein, as well as signal sequences from α-factor, immunoglobulins, outer membrane proteins, penicillinase, and T-cell receptors, among others.

To aid in the selection of host cells transformed or transfected with a recombinant vector of the present invention, the vector can be engineered to further comprise a coding sequence for a reporter gene product or other selectable marker. Such a coding sequence is preferably in operative association with the regulatory elements, as described above. Reporter genes that are useful in practicing the invention are well-known in the art and include those encoding chloramphenicol acetyltransferase (CAT), green fluorescent protein, firefly luciferase, and human growth hormone, among others. Nucleotide sequences encoding selectable markers are well-known in the art, and include those that encode gene products conferring resistance to antibiotics or anti-metabolites, or that supply an auxotrophic requirement. Examples of such sequences include those that encode thymidine kinase activity, or resistance to methotrexate, ampicillin, kanamycin, chloramphenicol, zeocin, tetracycline, and carbenicillin, among many others.

In specific though non-limiting embodiments, the present invention provides the following plasmid cloning vectors, constructed as described below in Section 11, which are present in host cells that have been deposited with the American Type Culture Collection (ATCC): plasmid pER416, which is present in host cells of strain Pz416 (ATCC 98926), and which plasmid comprises the ORF of omp20; plasmid pER418, which is present in host cells of strain Pz418 (ATCC 98928), and which plasmid comprises the ORF of ompW, plasmid pER417, which is present in host cells of strain Pz417 (ATCC 98927), and which plasmid comprises the ORF of omp27; plasmid pER419, which is present in host cells of strain Pz419 (ATCC 98929), and which plasmid comprises the ORF of ompA1; and plasmid pER420, which is present in host cells of strain Pz420 (ATCC 98930), and which plasmid comprises the ORF of ompA2.

5.4.2. Transformation of Host Cells

The present invention further provides host cells transformed with a polynucleotide molecule or recombinant vector of the invention, and cell lines derived therefrom. Host cells useful in practicing the present invention can either be prokaryotic or eukaryotic. Such transformed host cells include but are not limited to microorganisms, such as bacterial cells transformed with recombinant bacteriophage DNA, plasmid DNA or cosmid DNA expression vectors; or yeast cells transformed with recombinant expression vectors; or animal cells, such as insect cells infected with recombinant virus expression vectors, e.g., baculovirus, or mammalian cells infected with recombinant virus expression vectors, e.g., adenovirus or vaccinia virus, among others.

Bacterial cells are generally preferred as host cells. A strain of E. coli can typically be used, such as, e.g., strain DH5α, available from Gibco BRL, Life Technologies (Gaithersburg, Md.), or E. coli strain LW14, as described below. Eukaryotic host cells, including yeast cells, and mammalian cells, such as from a mouse, hamster, pig, cow, monkey, or human cell line, can also be used effectively. Examples of eukaryotic host cells that can be used to express the recombinant protein of the invention include Chinese hamster ovary (CHO) cells (e.g., ATCC Accession No. CCL61) and NIH Swiss mouse embryo cells NIH/3T3 (e.g., ATCC Accession No. CRL 1658).

A recombinant vector of the invention is preferably transformed or transfected into one or more host cells of a substantially homogeneous culture of cells. The vector is generally introduced into host cells in accordance with known techniques such as, e.g., by calcium phosphate precipitation, calcium chloride treatment, microinjection, electroporation, transfection by contact with a recombined virus, liposome-mediated transfection, DEAE-dextran transfection, transduction, conjugation, or microprojectile bombardment. Selection of transformants can be conducted by standard procedures, such as by selecting for cells expressing a selectable marker, e.g., antibiotic resistance, associated with the recombinant vector.

Once the vector is introduced into the host cell, the integration and maintenance of the APP coding sequence either in the host cell genome or episomally can be confirmed by standard techniques, e.g., by Southern hybridization analysis, restriction enzyme analysis, PCR analysis, including reverse transcriptase PCR (rt-PCR), or by immunological assay to detect the expected protein product. Host cells containing and/or expressing the APP coding sequence can be identified by any of at least four general approaches, which are well-known in the art, including: (i) DNA-DNA, DNA-RNA, or RNA-antisense RNA hybridization; (ii) detecting the presence of "marker" gene functions; (iii) assessing the level of transcription as measured by the expression of APP-specific mRNA transcripts in the host cell; and (iv) detecting the presence of mature APP protein product as measured, e.g., by immunoassay.

5.4.3. Expression of Recombinant Polypeptides

Once the APP coding sequence has been stably introduced into an appropriate host cell, the transformed host cell is clonally propagated, and the resulting cells are grown under conditions conducive to the maximum production of the APP protein. Such conditions typically include growing such cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the recombinantly-expressed APP protein is retained inside the host cells, the cells are harvested and lysed, and the APP protein is substantially purified or isolated from the lysate under extraction conditions known in the art to minimize protein degradation such as, e.g., at 4° C., or in the presence of protease inhibitors, or both. Where the recombinantly-expressed APP protein is secreted from the host cells, the exhausted nutrient medium can simply be collected and the APP polypeptide substantially purified or isolated therefrom.

The recombinantly-expressed APP protein can be partially or substantially purified or isolated from cell lysates or culture medium, as appropriate, using standard methods, including but not limited to any combination of the following methods: ammonium sulfate precipitation, size fractionation, ion exchange chromatography, HPLC, density centrifugation, and affinity chromatography. Increasing purity of the APP polypeptide of the present invention can be determined as based, e.g., on size, or reactivity with an antibody specific to the APP polypeptide, or by the presence of a fusion tag. For use in practicing the present invention, e.g., in a vaccine composition, the APP protein can be used in an unpurified state as secreted into the culture fluid, or as present in host cells or in a cell lysate, or in substantially purified or isolated form. As used herein, an APP protein is "substantially purified" where the protein constitutes more than about 20 wt % of the protein in a particular preparation. Also, as used herein, an APP protein is "isolated" where the protein constitutes at least about 80 wt % of the protein in a particular preparation.

The present invention thus provides a method for preparing an APP protein, homologous polypeptide, peptide fragment or fusion protein of the present invention, comprising culturing a host cell transformed with a recombinant expression vector, said recombinant expression vector comprising a polynucleotide molecule comprising a nucleotide sequence encoding: (a) an APP protein comprising the amino acid sequence of SEQ ID NO:2, 4, 6, 8, or 10, either with or without its native signal sequence; or (b) a polypeptide that is homologous to the APP protein of (a); or (c) a peptide fragment of the APP protein of (a) or homologous polypeptide of (b); or (d) a fusion protein comprising the APP protein of (a), homologous polypeptide of (b), or peptide fragment of (c), fused to a fusion partner; which polynucleotide molecule is in operative association with one or more regulatory elements that control expression of the polynucleotide molecule in the host cell, under conditions conducive to the production of the APP protein, homologous polypeptide, peptide fragment or fusion protein, and recovering the APP protein, homologous polypeptide, peptide fragment or fusion protein from the cell culture.

Once an APP protein of the present invention has been obtained in sufficient purity, it can be characterized by standard methods, including by SDS-PAGE, size exclusion chromatography, amino acid sequence analysis, serological reactivity, etc. The amino acid sequence of the APP protein can be determined using standard peptide sequencing techniques. The APP protein can be further characterized using hydrophilicity analysis (see, e.g., Hopp and Woods, 1981, Proc. Natl. Acad. Sci. USA 78:3824), or analogous software algorithms, to identify hydrophobic and hydrophilic regions. Structural analysis can be carried out to identify regions of the APP protein that assume specific secondary structures. Biophysical methods such as X-ray crystallography (Engstrom, 1974, Biochem. Exp. Biol. 11: 7–13), computer modelling (Fletterick and Zoller (eds), 1986, in: *Current Communications in Molecular Biology*, Cold Spring Harbor Laboratory, Cold Spring Harbor, N.Y.), nuclear magnetic resonance (NMR), and mass spectrometry can also be used to characterize the protein. Information obtained from these studies can be used, e.g., to design more effective vaccine compositions, or to select vaccines comprising only specific portions of the *APP* protein.

An *APP* protein that is useful in practicing the present invention is a polypeptide that: (a) is immunogenic, i.e., capable of inducing by itself, or capable of contributing in combination with other *APP* proteins or other *APP*-related antigens to the induction of, a protective response against *APP* when administered to swine; or (b) is capable of inducing the production of anti-*APP* antibodies when administered to a member of a mammalian species; or (c) can be used as a diagnostic reagent to detect the presence of anti-*APP* antibodies in a blood or serum sample from a pig resulting from infection with *APP* or from vaccination with a vaccine of the present invention. Such a protein, once prepared, can be identified using routine screening procedures known in the art. For example, the ability to induce, or contribute to the induction of, a protective immune response against *APP* can be identified by administering the *APP* protein, either alone or in combination with other *APP* proteins or other *APP*-related antigens, respectively, to a pig, and testing for the resulting induction of *APP*-neutralizing antibodies, or for the resulting ability of the vaccinated animal to resist subsequent challenge with *APP* compared to an unvaccinated control. The ability to induce the production of *APP*-specific antibodies can be identified by administering the *APP* protein to a model animal, such as a mouse, pig, sheep, goat, horse, cow, etc., and testing the animal's serum for the presence of *APP*-specific antibodies using standard techniques. The ability to use the *APP* protein as a diagnostic reagent can be determined by exposing the *APP* protein to a blood or serum sample of an animal previously or currently infected with *APP*, or previously vaccinated with a vaccine of the present invention, and detecting the binding to the *APP* protein of *APP*-specific antibodies from the sample using standard techniques, such as with an ELISA assay.

5.5. *APP* Vaccines

The present invention further provides a vaccine for protecting swine against *APP*, comprising an immunologically effective amount of one or more of the following: (a) an *APP* protein comprising an amino acid sequence selected from the group consisting of SEQ ID NOS:2, 4, 6, 8 or 10, either with or without its native signal sequence; (b) a polypeptide that is homologous to the *APP* protein of (a); (c) a peptide fragment consisting of a sub-sequence of the *APP* protein of (a) or the homologous polypeptide of (b); (d) a fusion protein comprising the *APP* protein of (a), homologous polypeptide of (b), or peptide fragment of (c), fused to a fusion partner; (e) an analog or derivative of the *APP* protein of (a), homologous polypeptide of (b), peptide fragment of (c), or fusion protein of (d); or (f) a polynucleotide molecule comprising a nucleotide sequence encoding the *APP* protein of (a), homologous polypeptide of (b), peptide fragment of (c), fusion protein of (d), or analog or derivative of (e); which *APP* protein, homologous polypeptide, peptide fragment, fusion protein, analog, derivative or polynucleotide molecule, can induce by itself, or in combination with one or more other such antigens contribute to the induction of, a protective response against *APP* in swine; and a veterinarily acceptable carrier. As used herein, the term "immunologically effective amount" refers to that amount of antigen that is capable of inducing, or contributing to the induction of, a protective immune response in swine against one or more serotypes of *APP* after either a single administration or after administration of divided doses.

The phrase "capable of inducing a protective immune response" is used broadly herein to include the induction of, or increase in, any immune-based response in the pig in response to vaccination, including either an antibody or cell-mediated immune response, or both, that serves to protect the vaccinated animal against *APP*. The terms "protective immune response", "protect", and the like, as used herein, are not limited to absolute prevention of *APP*-associated swine pneumonia or absolute prevention of infection of pigs by *APP*, but are intended to also refer to any reduction in the degree or rate of infection by the pathogen, or any reduction in the severity of the disease or in any symptom or condition resulting from infection with the pathogen, including, e.g., any detectable decrease in lung pathology, as compared to that occurring in an unvaccinated, infected control animal.

Vaccine compositions of the present invention can be formulated following accepted convention using standard buffers, carriers, stabilizers, diluents, preservatives, and solubilizers, and can also be formulated to facilitate sustained release. Diluents can include water, saline, dextrose, ethanol, glycerol, and the like. Additives for isotonicity can include sodium chloride, dextrose, mannitol, sorbitol, and lactose, among others. Stabilizers include albumin, among others.

Adjuvants can optionally be employed in the vaccine. Non-limiting examples of adjuvants include the RIBI adjuvant system (Ribi Inc.), alum, aluminum hydroxide gel, oil-in-water emulsions, water-in-oil emulsions such as, e.g., Freund's complete and incomplete adjuvants, Block co polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), or other saponin fractions, SEAM-1, monophosphoryl lipid A, Avridine lipid-amine adjuvant, heat-labile enterotoxin from *E. coli* (recombinant or otherwise), cholera toxin, or muramyl dipeptide, among many others. The vaccine can further comprise one or more other immunomodulatory agents such as, e.g., interleukins, interferons, or other cytokines.

Suitable veterinarily acceptable vaccine vehicles, carriers, and additives are known, or will be apparent to those skilled in the art; see, e.g., Remington's *Pharmaceutical Science*, 18th Ed., 1990, Mack Publishing, which is incorporated herein by reference. The vaccine can be stored in solution, or alternatively in lyophilized form to be reconstituted with a sterile diluent solution prior to administration.

The present invention further provides vaccine formulations for the sustained release of the antigen. Examples of such sustained release formulations include the antigen in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences*, Vol. 45, M. Dekker, NY, which is also incorporated herein by reference. Alternatively, or additionally, the antigen can be microencapsulated to improve administration and efficacy. Methods for microencapsulating antigens are well-known in the art, and include techniques described, among other places, in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes and liposome derivatives (e.g., cochleates, vesicles) can also be used to provide for the sustained release of the antigen. Details regarding how to make and use liposomal formulations can be found, among other places, in U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

In a non-limiting embodiment, the vaccine of the present invention can be a combination vaccine for protecting swine against *APP* and, optionally, one or more other diseases or pathological conditions that can afflict swine, which combination vaccine comprises a first component comprising an immunologically effective amount of an antigen of the present invention selected from the group consisting of an *APP* protein, homologous polypeptide, peptide fragment, fusion protein, analog, derivative, or polynucleotide molecule of the present invention which is capable of inducing, or contributing to the induction of, a protective response against *APP* in swine; a second component comprising an immunologically effective amount of an antigen that is different from the antigen in the first component, and which is capable of inducing, or contributing to the induction of, a protective response against a disease or pathological condition that can afflict swine; and a veterinarily acceptable carrier or diluent.

The second component of the combination vaccine is selected based on its ability to induce, or to contribute to the induction of, a protective response against either *APP* or another pathogen, disease, or pathological condition which afflicts swine, as known in the art. Any immunogenic composition now known or to be determined in the future to be useful in a vaccine composition for swine can be used in the second component of the combination vaccine. Such immunogenic compositions include but are not limited to those that provide protection against *Actinobacillus suis, Pasteurella multocida, Salmonella cholerasuis, Streptococcus suis, Erysipelothrix rhusiopathiae,* Leptospira sp., *Staphylococcus hyicus, Haemophilus parasuis, Bordetella bronchiseptica, Mycoplasma hyopneumoniae, Lawsonia intracellularis, Escherichia coli,* porcine reproductive and respiratory syndrome virus, swine influenza virus, transmissible gastroenteritis virus, porcine parvovirus, encephalomyocarditis virus, coronavirus, pseudorabies virus, and circovirus. In a non-limiting embodiment, the combination vaccine comprises a combination of components including one or more *APP* proteins of the present invention, and one or more other *APP* bacterial components such as APXI, ApxII, and Om1A.

The antigen comprising the second component can optionally be covalently linked to the antigen of the first component to produce a chimeric molecule. In a non-limiting embodiment, the antigen of the second component comprises a hapten, the immunogenicity of which is detectably increased by conjugation to the antigen of the first component. Chimeric molecules comprising covalently-linked antigens of the first and second components of the combination vaccine can be synthesized using one or more techniques known in the art. For example, a chimeric molecule can be produced synthetically using a commercially available peptide synthesizer utilizing standard chemical synthetic processes (see, e.g., Merrifield, 1985, Science 232:341–347). Alternatively, the separate antigens can be separately synthesized and then linked together by the use of chemical linking groups, as known in the art. Alternatively, a chimeric molecule can be produced using recombinant DNA technology whereby, e.g., separate polynucleotide molecules having sequences encoding the different antigens of the chimeric molecule are spliced together in-frame and expressed in a suitable transformed host cell for subsequent isolation of the chimeric fusion polypeptide. Where the vaccine of the invention comprises a polynucleotide molecule rather than a polypeptide, the spliced polynucleotide molecule can itself be used in the vaccine composition. Ample guidance for carrying out such recombinant techniques is provided, among other places, in Maniatis et al., 1989, above; Ausubel et al., 1989, above; Sambrook et al., 1989, above; Innis et al., 1995, above; and Erlich, 1992, above.

The present invention further provides a method of preparing a vaccine for protecting swine against *APP*, comprising combining an immunologically effective amount of one or more antigens of the present invention selected from the group consisting of an *APP* protein, homologous polypeptide, peptide fragment, fusion protein, analog, derivative, or polynucleotide molecule of the present invention which is capable of inducing, or contributing to the induction of, a protective response against *APP* in swine, with a veterinarily acceptable carrier or diluent, in a form suitable for administration to swine.

The present invention further provides a method of vaccinating swine against *APP*, comprising administering a vaccine of the present invention to a pig. The amount of antigen administered depends upon such factors as the age, weight, health and general physical characteristics of the animal being vaccinated, as well as the particular vaccine composition to be administered. Determination of the optimum dosage for each parameter can be made using routine methods in view, e.g., of empirical studies. The amount of *APP* protein administered will preferably range from about 0.1 $\mu$g to about 10 mg of polypeptide, more preferably from about 10 $\mu$g to about 1 mg, and most preferably from about 25 $\mu$g to about 0.1 mg. For a DNA vaccine, the amount of a polynucleotide molecule will preferably range from about 0.05 $\mu$g to about 500 mg, more preferably from about 0.5 $\mu$g to about 50 mg. In addition, the typical dose volume of the vaccine will range from about 0.5 ml to about 5 ml per dose per animal.

Animals can be vaccinated at any appropriate time, including within 1 week after birth, or at weaning age, or just prior to or at the time of breeding, or at the time that *APP* infection first begins to appear in one or more members of an animal population. Supplemental administrations, or boosters, may be required to achieve full protection. Methods for determining whether adequate immune protection has been achieved in an animal are well-known in the art, and include, e.g., determining seroconversion.

The vaccine can be administered by any appropriate route such as, e.g., by oral, intranasal, intramuscular, intra-lymph node, intradermal, intraperitoneal, subcutaneous, rectal or vaginal administration, or by a combination of routes. The skilled artisan will readily be able to formulate the vaccine composition according to the route chosen.

The present invention further provides a vaccine kit for vaccinating swine against infection or disease caused by *APP*, comprising a first container comprising an immunologically effective amount of one or more antigens of the present invention selected from the group consisting of an *APP* protein, homologous polypeptide, peptide fragment, fusion protein, analog, derivative, or polynucleotide molecule of the present invention which is capable of inducing, or contributing to the induction of, a protective response against *APP* in swine. The kit can optionally further comprise a second container comprising a veterinarily acceptable carrier or diluent. The vaccine composition can be stored in the first container either in solution or in lyophilized form to be reconstituted using the carrier or diluent of the second container.

5.6. Anti-*APP* Antibodies

The present invention further provides isolated antibodies that bind to an *APP* protein of the present invention. Such antibodies are useful for a variety of purposes including, e.g., as affinity reagents to purify the *APP* protein, or to detect the presence of the *APP* protein in a cell, tissue or fluid sample collected from an *APP*-infected animal, e.g., by use of an ELISA or Western blot assay, or as a therapeutic agent to prevent, control or treat *APP* infection.

Antibodies against an *APP* protein of the present invention can be raised according to known methods by administering an appropriate antigen of the present invention to a host animal selected from pigs, cows, horses, rabbits, goats, sheep, and mice, among others. Various adjuvants, such as those described above, can be used to enhance antibody production. Antibodies of the present invention can either be polyclonal or monoclonal. Polyclonal antibodies can be prepared and isolated from the serum of immunized animals and tested for anti-*APP* protein specificity using standard techniques. Alternatively, monoclonal antibodies against an *APP* protein can be prepared and isolated using any technique that provides for the production of antibody molecules by continuous cell lines in culture. These include but are not limited to the hybridoma technique originally described by Kohler and Milstein (Nature, 1975, 256: 495497); the human B-cell hybridoma technique (Kosbor et al., 1983, Immunology Today 4:72; Cote et al., 1983, Proc. Natl. Acad. Sci. USA 80: 2026–2030); and the EBV-hybridoma technique (Cole et al., 1985, *Monoclonal Antibodies and Cancer Therapy*, Alan R. Liss, Inc., pp. 77–96). Alternatively, techniques described for the production of single chain antibodies (see, e.g., U.S. Pat. No. 4,946,778) can be adapted to produce *APP* protein-specific single chain antibodies.

Also encompassed within the scope of the present invention are antibody fragments that contain specific binding sites for an *APP* protein of the present invention. Such fragments include but are not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed (see, e.g., Huse et al., 1989, Science 246: 1275–1281) to allow rapid identification of fragments having the desired specificity to an *APP* protein of the present invention.

Techniques for the production and isolation of monoclonal antibodies and antibody fragments are well-known in the art, and are additionally described, among other places, in Harlow and Lane, 1988, *Antibodies: A Laboratory Manual*, Cold Spring Harbor Laboratory, and in J. W. Goding, 1986, *Monoclonal Antibodies: Principles and Practice*, Academic Press, London. All of the above-cited publications are incorporated herein by reference.

5.7. Diagnostic Kits

The present invention further provides diagnostic kits. In a non-limiting embodiment, the diagnostic kit of the present invention comprises a first container comprising an *APP* protein, homologous polypeptide, peptide fragment, fusion protein, analog, or derivative of the present invention that can specifically bind to antibodies directed against the *APP* protein; and a second container comprising a secondary antibody directed against porcine antibodies. The secondary antibody preferably comprises a detectable label. Such a diagnostic kit is useful to detect pigs that currently are, or have previously been, infected with *APP*, or that have seroconverted as a result of vaccination with a vaccine of the present invention.

In an alternative embodiment, the present invention provides a diagnostic kit comprising a first container comprising a primary antibody that binds to an *APP* protein; and a second container comprising a secondary antibody that binds to a different epitope on the *APP* protein, or that is directed against the primary antibody. The secondary antibody preferably comprises a detectable label. In an alternative embodiment, the diagnostic kit comprises a container comprising a polynucleotide molecule or oligonucleotide molecule of the present invention that can specifically hybridize to, or amplify, an *APP*-specific polynucleotide molecule. These latter two diagnostic kits are useful to detect pigs that are currently infected with *APP*.

5.8. Anti-sense Oligonucleotides and Ribozymes

The present invention further provides oligonucleotide molecules that include anti-sense oligonucleotides, phosphorothioates and ribozymes that function to bind to, degrade and/or inhibit the translation of an *APP* protein-encoding mRNA.

Anti-sense oligonucleotides, including anti-sense RNA molecules and anti-sense DNA molecules, act to directly block the translation of mRNA by binding to targeted mRNA and thereby preventing protein translation. For example, antisense oligonucleotides of at least about 15 bases and complementary to unique regions of the mRNA transcript sequence encoding an *APP* protein can be synthesized, e.g., by conventional phosphodiester techniques.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of *APP* protein mRNA sequences are also within the scope of the invention.

Specific ribozyme cleavage sites within any potential RNA target are initially identified by scanning the target molecule for ribozyme cleavage sites which include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both the anti-sense oligonucleotides and ribozymes of the invention can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors which incorporate suitable RNA polymerase promoters such as the T7 or SP6 polymerase promoters.

Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

The following examples are illustrative only, and are not intended to limit the scope of the present invention.

6. EXAMPLE: IDENTIFICATION OF NOVEL APP PROTEINS

Results of the following experiment demonstrate the specificities of local antibody responses induced when pigs that were previously challenged with APP serotype-5 were heterologously rechallenged with APP serotype-7. The antibody specificities were used to identify previously unrecognized APP proteins, three of which (Omp20, OmpW, Omp27) were shown by Western blot analysis to be present in all twelve APP serotypes. The two additional novel proteins (OmpA1, OmpA2) were identified following protein fraction isolation and concentration (see Section 6.1.6, below).

6.1. Materials and Methods

6.1.1. Bacterial Challenge

The APP serotype-5 culture (strain K-17) used to prepare porcine challenge material was obtained from Dr. R. A. Schultz, Avoca, Iowa, USA. The APP serotype-7 culture (strain WF-83) used to prepare porcine challenge material was obtained from Dr. E. Jones, Swedeland, Pa., USA.

Clinically healthy 7–8 week old cross-bred pigs were obtained from a herd in Nebraska with no previous history of APP infection, and were housed in isolation facilities at Pfizer Animal Health, Lincoln, Nebr., according to IACUC guidelines. Animals were examined by a veterinarian to determine their health status prior to initiation of the study. Following a 2-week acclimatization period, pigs were anesthetized using a combination of 100 mg/ml of Telazol, 50 mg/ml of Xylazine, and 50 mg/ml of Ketamine administered at a rate of approximately 1 ml/50 lb of body weight, and intranasally inoculated with $2.6 \times 10^6$ cfu of APP serotype-5. Seventy-eight days after primary challenge, six of the surviving pigs, which had demonstrated clinical APP disease but had recovered, were again anesthetized as described above. The first and second of these 6 pigs were intranasally rechallenged with $1 \times 10^7$ cfu of APP serotype-5 (homologous rechallenge); the third and fourth of these pigs were intranasally rechallenged with $1 \times 10^8$ cfu of APP serotype-7 (heterologous rechallenge); and the fifth and sixth pigs were intranasally inoculated with bacterial growth medium only (control). All challenge inoculums were administered in 1 ml volumes (0.5 ml/nostril).

All pigs were sacrificed 48 hrs post-rechallenge, their serum and organs were collected, and tissue pieces from the organs were cultured in vitro for 24 or 48 hr, as described in Sections 6.1.2 and 6.1.3 below. Antibody-containing supernatants from the tissue explant cultures were used to compare the memory antibody profile elicited by heterologous rechallenge to that elicited by homologous rechallenge or single challenge (control). The specificity of antibodies produced by the tissue explants in vitro was determined by Western blot analysis against a panel of whole bacterial cell preparations representing all 12 APP serotypes. This analysis established the presence of an antibody profile following heterologous rechallenge that was distinct from the antibody profile following homologous rechallenge or single challenge (control).

APP serotype-1 (strain 4074), serotype-2 (strain 4226), serotype-3 (strain 1421), serotype-4 (strain M62), serotype-5 (strain K-17), serotype-6 (strain Femo FE 171D), serotype-7 (strain WF-83), serotype-8 (strain 405), serotype-9 (strain CVJ-13261), serotype-10 (strain 13039), serotype-11 (strain 56153), and serotype-12 (strain 8329) reference cultures used to prepare material for Western blots were obtained from Dr. B. Fenwick, Kansas State University, Manhattan, Kans., USA.

6.1.2. Tissue Collection

Serum samples were obtained from pigs prior to rechallenge, and again prior to necropsy (48 hr post-rechallenge). Pigs were euthanized 48 hr post-rechallenge with an overdose of intravenous pentobarbital. Lungs were removed and examined for characteristic gross lesions attributable to APP infection, and a complete gross examination was done of all major organs. Tissue samples of lung, lymph nodes (mesenteric, popliteal, and bronchial), Peyers patches, and tonsils were collected, washed with 70% ethanol, and rinsed 3× in RPMI transport media (RPMI medium (Gibco/BRL, Grand Island, N.Y.) supplemented with 10 mM HEPES, 5% FBS, 50 U/ml of penicillin and 50 μg/ml of streptomycin). After washing, tissues were placed in 50 ml centrifuge tubes containing 10 ml of transport media and placed on ice until processed in the laboratory (within 3 hr of collection). Additional tissues samples were frozen in liquid nitrogen for future mRNA isolation and immunohistochemistry, or fixed in formalin for histopathology. A sample of lung tissue was also submitted to the University of Nebraska-Lincoln diagnostic laboratory for bacterial identification.

6.1.3. Tissue Explant Cultures

Tissues were placed in individual Petri dishes containing approximately 5 ml of transport media. Small tissue pieces of approximately 2×2 mm were cut off from the original sample with a scalpel blade and/or scissors and placed in individual wells of 12- or 24-well plates (Costar, Cambridge, Mass.) containing 2 ml of wash media ($Ca^{2+}$ and $Mg^{2+}$ free Hank's balanced salt solution (HBSS) supplemented with 10 mM HEPES and 50 μg/ml of gentamicin). The tissue pieces were rinsed in the wash media and transferred to another well containing wash media. This washing/rinsing operation was repeated four times, and the tissue pieces were then transferred to wells containing RPMI media supplemented with 10% FBS, 10 mM HEPES, 2 mM glutamine, 50 μg/ml gentamicin, 62 μg/ml amphotericin B, 40 μg/ml sodium desoxycholate, 50 U/ml penicillin and 50 μg/ml of streptomycin. Plates were incubated at 38.5° C. for 24 or 48 hr in a humidified chamber having 5% $CO_2$. After incubation, supernatant fluids were removed and frozen at −70° C.

6.1.4. Western Blot Analysis

The specificity of recovered antibodies in the tissue explant supernatants was examined by Western blot analysis as follows. Representative isolates of each of the 12 APP serotypes were each grown separately to generate whole bacterial cell antigen to test the supernatants. Each strain was cultured (1% seed) in minimal medium-3 (MM3) (1.8% Bacterin HP medium, 1.7% lactic acid, 0.3% glycerol, 0.05M HEPES, 0.011 M L-glutamic acid (monosodium salt), $5 \times 10^{-5}$ M nicotinamide, and 0.2% casamino acids) supplemented with 10 μg/ml of β-nicotinamide adenine dinucleotide (β-NAD), for 5–6 hr at 37° C. and 180 rpm until OD$_{560}$ of ~0.5–0.6. The cells were pelleted by centrifugation at 12,000×g for 10 min, the medium was reserved for analysis, and the pellet was resuspended in 5 ml Dulbecco's phosphate buffered saline (DPBS). Prior to the protein assay, the resuspended pellet was frozen at −20° C. and then thawed in order to lyse any intact bacterial cells. The protein concentration of each preparation was determined using a BCA Protein Assay Reagent Kit (Pierce, Rockford, Ill.). *APP* antigen preparations (5 µg/lane) were loaded onto a 4–20% Tris-glycine gel (Novex, San Diego, Calif.), and proteins were separated by electrophoresis at rm temp with a constant current of 20 mA.

Separated proteins were transferred to ProBlot™ membranes (Applied Biosystems, Foster City, Calif.) using a semi-dry graphite electroblotter (Milliblot, Millipore, Seattle, Wash.). Transfer was performed at rm temp for 30 min at a constant current of 200 mA. After transfer was complete, membranes were blocked by incubating overnight at rm temp with Buffer A (50 mM Tris HCl, 150 mM NaCl, pH 7.4 and 5% (w/v) nonfat dried milk). The blocking buffer was then decanted and replaced with either serum (1:100 dilution) or tissue explant culture supernatants (1:3 dilution) in Buffer A, and the membranes were incubated for 1 hr at rm temp, followed by a 10 min wash in Buffer B (Buffer A containing 0.2% (v/v) Triton X-100) and two 10 min washes in Buffer A. After washing was complete, the membranes were incubated for 1 hr at rm temp with phosphatase-conjugated goat anti-swine antibodies (Kirkegaard & Perry Laboratories, Gaithersburg, Md.) diluted 1:1000 in Buffer A. The membranes were then washed in Buffer A for 10 min, and incubated for 15 min with 5-bromo4-chloro-3-indolyl-phosphate/nitroblue tetrazolium (BCIP/NBT) substrate system (Kirkegaard & Perry Laboratories).

6.1.5. Preparation of *APP* Serotype-7 Membranes

An aliquot of *APP* serotype-7 was seeded (1%) into MM3 supplemented with 10 µg/ml β-NAD and cultured overnight at 37° C. (180 rpm). A portion of the overnight culture was inoculated into fresh medium (bacterial inoculum was 3% of total volume) and incubated for 5–6 hr or to a culture density of 274 Klett units. The cells were pelleted by centrifugation at 4,500 rpm for 40 min at 10° C., the supernatant was removed, and the pellet was resuspended in 5 ml of 50 mM Tris-HCl, pH 8.0, with sufficient PMSF (phenyl methylsulfonyl fluoride) to result in a final concentration of 1 mM PMSF. Bacterial cells were lysed using a French Press under 16,000 lb/in$^2$ in a 40K PSI pressure cell (Sim Aminco., Rochester, N.Y.). The broken cells were centrifuged at 1,000×g for 15 min to remove large bacterial debris. Crude total membranes were collected by centrifugation at 45,000 rpm for 60 min at 18° C. The supernatant was discarded, the pellet was resuspended in 50 mM Tris-HCl, pH 8.0, and protein was determined using the Bradford Standard Protein Assay.

To 15 mg of crude membrane in a 3 ml volume was added 30 µl of 100 mM PMSF and 750 µl of 2.5% sarkosyl, and the entire volume was mixed thoroughly. After a 30 min incubation on ice, the membranes were pelleted by centrifugation at 200,000×g for 15 min at 10° C. The supernatant was removed from the pelleted membrane fraction and the pellet was resuspended in 3 ml of 50 mM Tris-HCl/100 mM NaCl, pH 8.0. This membrane preparation, which represented the *APP* serotype-7 membrane antigen, was then stored at −20° C.

6.1.6. Membrane Protein Fractionation and Purification

Purification of *APP* proteins for N-terminal sequencing was achieved through continuous-elution SDS-PAGE using a BioRad Model 491 Prep Cell (BioRad, Richmond, Calif.). A 10 ml volume (4.5 mg total protein) of *APP* serotype-7 membrane protein fraction was mixed with an equal volume of non-reducing sample buffer (125 mM Tris-HCl, pH 6.8, 4% SDS, 20% glycerol, and 0.1% bromphenol blue). The protein-buffer mixture was boiled for 5 min and applied to a 3% stacking/15% separation SDS-polyacrylamide gel. Samples were electrophoresed at 20 mA constant current (initial voltage 175–250 V, final voltage 200–300 V) for 72 hr. Approximately 800×5 ml fractions were collected at a flow rate of 1 ml/min throughout the run, and analyzed for protein content by spectrophotometry at A$_{280}$. Every 10th fraction was analyzed by SDS-PAGE and silver staining (Bio-Rad, Richmond, Calif.). Fractions which putatively contained the same protein, as determined by molecular weight, were pooled and stored at 4° C. Pooled samples were desalted and concentrated in preparation for N-terminal sequencing. Desalting was performed by applying aliquots of pooled sample to a Presto™ desalting column (Pierce, Rockford, Ill.) with a 10 ml bed volume. Three ml aliquots of each protein pool were applied to separate columns and eluted in ddH$_2$O in 10×2 ml fractions. This was repeated 10 times for each protein pool until 30 ml had been desalted. As determined by Western blot analysis, the majority of the desalted protein was found in fraction No. 2. Therefore, the second fraction from each of the 10 elutions were pooled for each individual protein. The resulting 20 ml samples were lyophilized and resuspended in 0.5 ml ddH$_2$O for N-terminal sequencing. N-terminal sequences were obtained at the Pfizer Central Research Molecular Sciences Sequence Facility.

6.2. Results

6.2.1. Clinical Signs and Pathological Findings After Rechallenge

Pigs did not show any signs of clinical disease after either homologous (serotype-5) or heterologous (serotype-7) rechallenge. Pathological examination confirmed that the animals had not developed lung lesions that would be consistent with acute *APP* infection following rechallenge. However, bronchial lymph nodes of the animals rechallenged with serotype-7 were hemorrhagic and enlarged compared to those from animals homologously rechallenged with serotype-5 or from control animals.

6.2.2. Specificity of Antibodies Elicited by Rechallenge

Figure 1B:
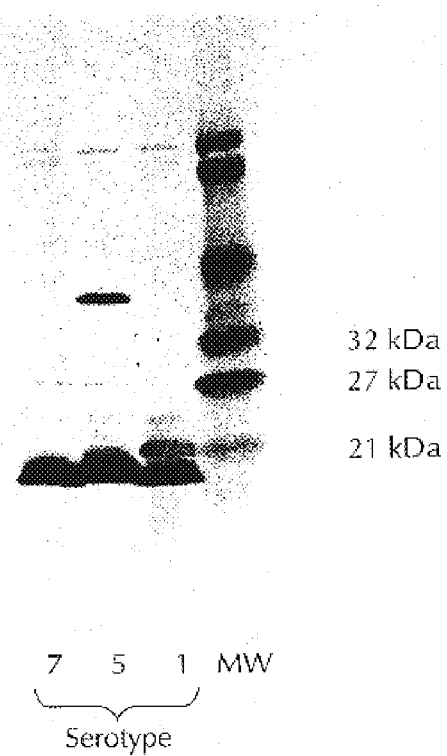

The specificity of antibodies present in serum and tissue explant supernatants was assessed by Western blot analysis as described above. All tissue-derived supernatants collected after 24 or 48 hr incubation contained antibodies that specifically recognized *APP* proteins. In general, the reactivity against serotype-5 antigens was greater than the reactivity against antigens of serotype-7 or serotype-1. However, the reactivity of most tissue-derived supernatants was less intense and narrower in spectrum than the reactivity of serum (FIG. 1a). In general, the reactivity of tissue explant supernatants had no particular pattern. Nevertheless, the pattern of Western blot reactivity of tissue explant supernatants from one specific animal (No. 803, heterologously rechallenged with serotype-7) was strong, and highlighted several low molecular weight proteins present in *APP* serotypes-1, -5, and -7 (FIG. 1b). This supernatant was used as the antibody source to further characterize the degree of cross-reactivity of the secondary (memory) antibody response elicited by heterologous rechallenge with *APP* serotype-7 in pigs that had been challenged initially with *APP* serotype-5.

The degree of cross-reactivity of the antibodies in the BLN tissue explant supernatants from pig No. 803 was assessed by Western blot analysis using whole bacterial cell antigens prepared from each of the twelve different *APP* serotypes. This analysis showed that three of the low molecular weight proteins recognized by the antibodies were present in all twelve serotypes (FIG. 2). Antibodies present in this BLN tissue explant supernatant also recognized other protein bands. A high molecular weight band present in serotypes-1, 2, 4, 5, 6, 7, 8, and 9, which may correspond to the exotoxin, Apx II (see Nakai, 1983, above), and another protein band present in serotypes 2, 5, 8 and 10, represented the second most cross-reactive patterns. Western blot analysis of *APP* cell pellets and supernatants revealed that reactivity of antibodies in the BLN tissue explant supernatants to the low molecular weight proteins was restricted to proteins present in the cell pellets (FIG. 3), indicating that the proteins are associated with the bacterial cell and are not secreted.

6.2.3. Proteins Recognized by Cross-reactive Antibodies

Figure 4A:
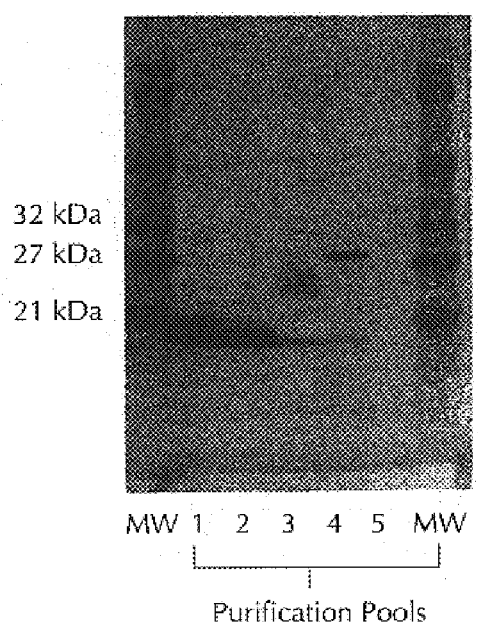
Figure 4B:
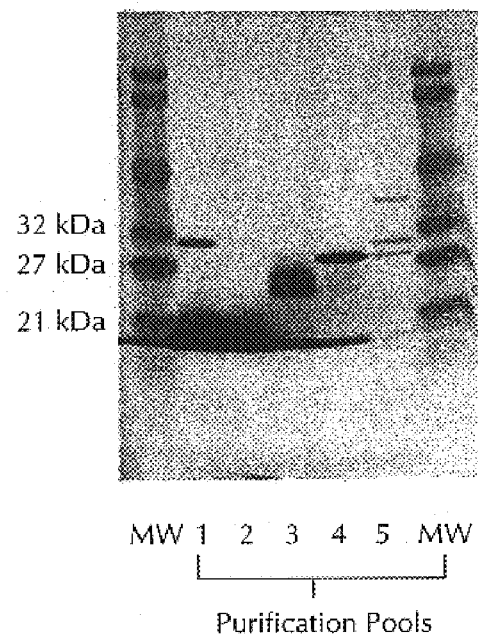

The low molecular weight proteins were purified as described above, yielding partially purified preparations containing the protein of interest as identified by Western blot analysis using: (a) BLN tissue explant supernatant fluids from pig No. 803; or (b) serum from pig No. 803 (FIG. 4). Upon fractionation of membrane proteins, four protein bands with molecular weights of about 19–20, about 23, about 27, and about 29 kDa, respectively, were identified using this procedure.

N-terminal sequence analysis of the proteins in the four bands yielded a primary sequence and tentative residues (in parentheses) as shown in TABLE 1, below, and designated therein as "Pep-1" (SEQ ID NO:11), "Pep-2" (SEQ ID NO:12), "Pep-3" (SEQ ID NO:13), and "Pep-4" (SEQ ID NO:14). Occasional secondary signals were observed and were probably due to the presence of minor contaminants (data not shown). The partial N-terminal sequences shown in TABLE 1 were used to design probes and primers to obtain the primary DNA sequences encoding the cross-reactive *APP* proteins. Sequence homology comparisons suggested that the four proteins recognized by the dominant local antibody response elicited after heterologous rechallenge have not previously been described for *APP*.

TABLE 1

N-Terminal Amino acid Sequences of Low Molecular Weight APP Proteins

| Peptide (SEQ ID NO) | Approx. Mol. Wt (kDa) | Protein Name | Sequence[1] (NH$_2$ to COOH) |
|---|---|---|---|
| Pep-1 (11) | 19–20 | Omp20 | Ala-Pro-Val-Gly-Asn-Thr-Phe-Thr-Gly-Val-(Lys)-Val-(Tyr)-Val-Asp-Leu-Thr-Xaa-Val-Ala |
| Pep-2 (12) | 23 | OmpW | His-Gln-Ala-Gly-Asp-Val-Ile-Phe-Arg-Ala-Gly-Ala-Ile-Gly-Val-Ile-Ala-Asn-Ser-Ser-Ser-Asp-Tyr-(Gln)-Thr-(Gln)-Ala-Asp-Val-(Asn/Val)-Leu-Asp-Val-Asn-Asn |
| Pep-3 (13) | 27 | Omp27 | Ala-Glu-Ile-Gly-Leu-Gly-(Gly)-Ala-Arg-Glu-(Ser)-(Ser)-Ile-Tyr-Tyr-(Ser)-Lys-His-Lys-Val-Ala-Thr-Asn-Pro-Phe-Leu-Ala-Leu-Asp-Leu |
| Pep-4 (14) | 29 | OmpA | Ala-(Asp/Glu)-Pro-Glu-Asn-Thr-Phe-Tyr-Pro-Gly-Ala-Lys-Val-Xaa-Xaa-(Ser)-Xaa-(Phe)-(His) |

[1]Xaa indicates that the amino acid residue at the particular position could not be determined.

7. EXAMPLE: MOLECULAR CLONING OF DNA ENCODING THE *APP* PROTEINS 7.1. Isolation of Chromosomal DNA and Construction of Genomic Libraries Genomic DNA from each of the twelve *APP* serotypes was separately isolated by either the hexadecyltrimethyl ammonium bromide (CTAB)-proteinase K method (Ausubel et al., 1988, Curr. Protocols Mol. Biol. Wiley Interscience, NY), or the DNA Isolator Genomic DNA Isolation Reagent (Genosys Biotechnologies, Inc., The Woodlands, Tex.). The *APP* DNA was dissolved in TE buffer (10 mM Tris-HCl, pH 8.0, 1 mM EDTA) at <1 µg/ml and quantitated by UV spectrophotometry.

To facilitate cloning of the *APP* gene sequences encoding Omp20, OmpW, Omp27, and OmpA, several genomic libraries were constructed. These libraries were specifically modified by ligation of a known sequence (Vectorette II™, Genosys Biotechnologies, Inc., The Woodlands, Tex.) to the 5' and 3' ends of restricted DNA fragments essentially as recommended by the supplier. Thus, Vectorette libraries were constructed by separately digesting two pg chromosomal DNA FROM *APP* 7-1 (serotype 7, passage 1) with restriction endonuclease BamHI, Bg/II, HindIII, EcoRI, DraI or HpaI at 37° C. overnight. The reaction was then spiked with additional fresh restriction enzyme and adjusted to 2 mM ATP, 2 mM DTT final concentration. Vectorette tailing was carried out by addition of T4 DNA Ligase (400 U) plus 3 pMol of the appropriate compatible Vectorette linker (BamHI Vectorette: BamHI, Bg/II; HindIII Vectorette: HindIII; EcoRI Vectorette: EcoRI; Blunt Vectorette: DraI, HpaI). The mixture was incubated for three cycles at 20° C., 60 min; 37° C., 30 min to complete the tailing reaction, and then adjusted to 200 µl with dH$_2$O and stored at −20° C.

7.2. Molecular Cloning of omp20

Screening of the Vectorette libraries was carried out to obtain DNA fragments encoding Omp20 and flanking regions. Degenerate oligonucleotide ER49 (SEQ ID NO: 39) was designed based on the N-terminal amino acid sequence of this protein (TABLE 1, Pep-1 (SEQ ID NO:11), aa 1–9).

For PCR amplification of a fragment of the omp20 gene, oligonucleotide ER49 (SEQ ID NO: 39) was used in combination with a Vectorette specific primer, ER70 (SEQ ID NO: 48) in 50 µl reactions containing 1×PCR Buffer II (Perkin Elmer), 1.5 mM MgCl$_2$, 200 µM each deoxy-NTP, 100 pMol each primer, and 2.5 U AmpliTaq Gold (Perkin Elmer) thermostable polymerase. Multiple single reactions were performed with 5 µl of the Vectorette libraries as DNA template. Amplification was carried out as follows: denaturation (95° C., 9 min); 35 cycles of denaturation (95° C., 30 sec), annealing (550C, 1 min), and polymerization (72° C., 3 min); followed by a final extension (72° C., 7 min).

The amplified products were visualized by separation on a 1.2% agarose gel (Sigma). A 433-bp product resulted from amplification of the EcoRI Vectorette library. The fragment was cloned into pGEM®-T Easy PCR cloning vector (Promega, Madison, Wis.) and sequenced. Analysis of the sequence confirmed the identity of the fragment as partially encoding Omp20 based on the N-terminal amino acid sequence (Pep-1).

Based on the newly identified sequence of this partial gene, specific primers ER67 (SEQ ID NO: 46) and ER68 (SEQ ID NO: 47) were designed to obtain additional 5' and 3'flanking sequences by a second round of screening the Vectorette libraries by PCR amplification as described above. Screening of EcoRI, HindIII, DraI, and HpaI Vectorette libraries by PCR, employing ER68 (SEQ ID NO: 47) plus ER70 (SEQ ID NO: 48), resulted in successful amplification of an approximately 600-bp fragment from the DraI Vectorette library. This fragment was sequenced to determine the 3' end of the omp20 gene. Since no unique products were observed during screening of these libraries using ER67 (SEQ ID NO: 46) plus ER70 (SEQ ID NO: 48), additional specific primers ER71 (SEQ ID NO: 49), ER72 (SEQ ID NO: 50), ER76 (SEQ ID NO:52), and ER77 (SEQ ID NO:53) were designed to obtain DNA fragments located 5' of the ER49 binding site. Such "genome walking" by amplification from numerous Vectorette DNA libraries was reiterated until the outer boundaries of the ORF, i.e., translational start and stop codons as well as flanking nucleotide sequences, were characterized. Generally, PCR products were sequenced directly or cloned into pGEM®-T Easy PCR cloning vector prior to sequence analysis.

7.3. Molecular Cloning of omp27

Screening of the Vectorette libraries for omp27 was carried out essentially as described above for omp20, except that degenerate oligonucleotide ER50 (SEQ ID NO:40), which was designed based on the N-terminal amino acid sequence of the purified Omp27 protein (TABLE 1, Pep-3 (SEQ ID NO:13), aa 13–24), was used. Following PCR amplification of Vectorette libraries as described above, a 152-bp fragment was confirmed to encode a portion of Omp27 based on the N-terminal amino acid sequence of Pep-3 (SEQ ID NO:13). A second round of genome walking using BamHI, Bg/II, HindIII, EcoRI, HpaI, and DraI Vectorette libraries and specific primers ER88 (SEQ ID NO:64), and ER89 (SEQ ID NO:65) resulted in PCR amplification of an approximately 2 kb fragment from the DraI library, and an approximately 1.5 kb fragment from the HindIII library. These DNA fragments were cloned into pGEM®-T Easy PCR cloning vector, which allowed for derivation of the nucleotide sequence 5' and 3' of the omp27 gene, respectively.

7.4. Molecular Cloning of ompA1 and ompA2

The N-terminal amino acid sequence obtained from the purified 29 kDa protein (TABLE 1, Pep-4 (SEQ ID NO:14)) was used to design degenerate N-terminal primers RA22 (SEQ ID NO: 73) and RA34 (SEQ ID NO:77) for use in direct PCR amplification of the gene encoding the 29 kDa protein from APP chromosomal DNA. The sequence of Pep4 was analyzed using a BlastP computer program comparison (National Center for Biotechnology Information) against the GenBank protein database (Altschul et al., 1990, J. Mol. Biol. 215:403–10), and was found to exhibit homology with OmpA proteins of several different eubacteria, such as *Pasteurella multocida, P. haemolytica, Haemophilus ducreyi, H. somnus, H. influenzae, Actinobacillus actinomycetemcomitans, E. coli*, Shigella, and Salmonela. N-terminal sequences of the OmpA-related proteins from the Pasteurellaceae were aligned to produce the consensus sequence Ala-Pro-Gln-Ala/Glu-Asn-Thr-Phe-Tyr-Ala/Val-Gly-Ala-Lys-Ala (SEQ ID NO:94). These alignments were analyzed and used to design several additional N-terminal degenerate primers. Oligonucleotide primers RA53 (SEQ ID NO:81), RA54 (SEQ ID NO:82), RA55 (SEQ ID NO:83), RA56 (SEQ ID NO:84), and RA57 (SEQ ID NO:85) overlap each other, and were designed to bind to the region encoding aa 4–11, aa 5–12, aa 3–10, aa 1–8, and aa 1–7, respectively, of this consensus peptide.

Other degenerate oligonucleotide primers were designed following alignment of the C-terminal regions of the OmpA-related proteins. This alignment indicated a highly conserved region near the C-terminus which included the amino acid sequence Cys-Leu-Ala-Pro-Asp-Arg-Arg-Val-Glu-Ile (SEQ ID NO:95). Both RA49 (SEQ ID NO:78) and RA50 (SEQ ID NO:79) reverse primers were designed to bind to the negative DNA strand in this region of OmpA. These reverse primers were applied in a two-dimensional matrix in which RA49 (SEQ ID NO:78) and RA50 (SEQ ID NO:79) were each combined pairwise with RA22 (SEQ ID NO:73), RA34 (SEQ ID NO:77), RA53 (SEQ ID NO:81), RA54 (SEQ ID NO:82), RA55 (SEQ ID NO:83), RA56 (SEQ ID NO:84), and RA57 (SEQ ID NO:85) in HotStart 50™ tubes (Molecular Bioproducts Inc., San Diego, Calif.) with combined KlenTaq1 and Pfu polymerases. The following references describe "hot start" methods: D'Aquila et al., 1991, Nucl. Acids Res. 19:3749; and Horton et al., 1994, Biotechniques 16:42–43. The cycling program for PCR was a variant of "touchdown PCR" protocols and was carried out as follows: denaturation (94° C., 5 min); 30 cycles of denaturation (94° C., 30 sec), annealing (59° C., 30 sec initial cycle, then –0.1° C. per additional cycle), and polymerization (72° C., 1 min); followed by a final extension (72° C., 15 min). The following references describe "touchdown PCR" protocols: Roux, 1994, BioTechniques, 16:812–814; and Hecker and Roux, 1996, BioTechniques 20:478–485.

Among the PCR products generated, an approximately 950-bp band was produced from reactions with either RA49 (SEQ ID NO:78) or RA50 (SEQ ID NO:79), when each was combined pairwise with the forward primers RA34 (SEQ ID NO:77), RA53 (SEQ ID NO:81), RA56 (SEQ ID NO:84), or RA57 (SEQ ID NO:85). These DNA fragments were cloned into pGEM®-T Easy PCR cloning vector and sequenced. Analysis of these sequenced fragments indicated the existence of two different variant sequences. Products derived from RA49 (SEQ ID NO:78)/RA57 (SEQ ID NO:85), and RA50 (SEQ ID NO:79)/RA56 (SEQ ID NO:84), represented variant A1, and the partially encoded protein was designated as "OmpA1." Products derived from RA50 (SEQ ID NO:79)/RA34 (SEQ ID NO:77), and RA50 (SEQ ID NO:79)/RA53 (SEQ ID NO:81) represented variant A2, and the partially encoded protein was designated as "OmpA2."

The two similar yet distinct ompA partial DNA sequences were expanded to include the entire ORFs and flanking 5' and 3' sequences through genome walking by application of the previously described Vectorette libraries. Alignment of the partial ompA1 and ompA2 DNA sequences allowed the design of specific oligonucleotide primers capable of differentiating these closely related gene sequences. Outward facing, differentiating primers specific for the 5' or 3' regions of ompA1, ie., ER55 (SEQ ID NO:41), ER58 (SEQ ID NO:42), and for ompA2, i.e., ER59 (SEQ ID NO:43), ER62 (SEQ ID NO:44), respectively, were used to probe Vectorette libraries as described above. Unique fragments of approximately 1100, 400, 450, and 280-bp were obtained from an EcoRI Vectorette library when probed with ER70 (SEQ ID NO:48) plus either ER55 (SEQ ID NO:41), ER58 (SEQ ID NO:42), ER59 (SEQ ID NO:43), or ER62 (SEQ ID NO:44), respectively. Sequence analysis of the resulting fragments allowed determination of the endpoints and flanking regions of both ompA1 and ompA2 ORFs.

7.5. Molecular Cloning of ompW

The N-terminal amino acid sequence obtained from the purified 23 kDa protein (TABLE 1, Pep-2 (SEQ ID NO:12)) was used to design RA20 (SEQ ID NO:72), a degenerate oligonucleotide primer corresponding to amino acids 1–8 of Pep-2.

Purified APP DNA was used as a template in a variant of "gene walking PCR" methods. The single PCR primer RA20 (SEQ ID NO:72) was used in 'hot start' reactions with combined KlenTaq1 (Ab Peptides, Inc, St. Louis, Mo.) and Pfu (Stratagene, Inc., La Jolla, Calif.) polymerases. The cycling program for PCR was a variant of "touchdown PCR" protocols and was carried out as follows: denaturation (94° C., 5 min); 40 cycles of denaturation (94° C., 1 min), annealing (63° C., 2 min initial cycle, then −0.2° C. and −2 sec per additional cycle), and polymerization (72° C., 1.5 min); followed by a final extension (72° C., 10 min).

Among the numerous PCR products generated, an approximately 220-bp product was obtained and cloned into pGEM®-T Easy PCR cloning vector. Sequence analysis of this plasmid insert confirmed that the cloned PCR product encoded amino acids corresponding to a portion of the 23 kDa protein based on the N-terminal amino acid sequence of Pep-2 (SEQ ID NO:12).

Based on this newly identified sequence, a specific primer, RA23 (SEQ ID NO:74), was generated for the amplification of downstream sequences. Genomic mini-libraries of *APP* serotype-7 DNA were constructed by limited digestions with Taq$^\alpha$I or HinP1I, which both create 5'-CG overhangs. This DNA was ligated into a BspDI-cut pUC21 or pUC128 vector and transformed into *E. coli* DH5α to yield the genomic libraries.

Mini-preps of these plasmid-borne genomic libraries were used as templates in "gene walking PCR" using "hot start" methods. The specific primer RA23 (SEQ ID NO:74), along with vector-specific M13 Forward and M13 Reverse sequencing primers, was used with combined KlenTaq and Pfu polymerases. The cycling program for PCR was carried out as follows: denaturation (94° C., 5 min); 32 cycles of denaturation (94° C., 30 sec), annealing (63° C., 30 initial cycle, then −0.2° C. per cycle), and polymerization (72° C., 30 sec); followed by a final extension (72° C., 7 min).

Among the numerous PCR products generated, a 0.8 kb product and a 1.4 kb product were cloned into pGEM®-T Easy PCR cloning vector and sequenced. Analysis and alignments of the resulting sequences along with that obtained above yielded the sequence of the mature protein. In order to obtain the sequence of the 5' flanking region of the ompw gene, specific primers RA24 (SEQ ID NO:75) and RA26 (SEQ ID NO:76) were used to probe numerous Vectorette libraries, as described above. Amplification was carried out as follows: denaturation (95° C., 9 min); 40 cycles of denaturation (95° C., 30 sec), annealing (60° C., 1 min), a polymerization (72° C., 3 min); followed by a final extension (72° C., 7 min). Specific 600 and 700-bp products resulted from probing the HpaI and DraI Vectorette libraries, respectively. The 700-bp product was directly sequenced to obtain the nucleotide sequence encompassing the 5'-flanking region, and encoded the N-terminus of the 23 kDa protein. Due to partial similarity between the predicted *APP* 23 kDa protein and the predicted *Vibrio cholerae* OmpW protein, the *APP* gene fragment was designated as "ompW."

7.6. Molecular Analysis of Genes Encoding *APP* Proteins 7.6.1. Specific PCR Amplification of DNA Results from the cloning and preliminary sequencing of the novel *APP* proteins, as described above, were used to design oligonucleotide primers for the specific amplification of the intact omp20, omp27, ompA1, ompA2 and ompW genes directly from *APP* serotype-7 chromosomal DNA. This approach was preferred based on the desire to eliminate the introduction of sequencing artifacts due to possible mutations arising during the cloning of gene fragments in *E. coli*. Accordingly, oligonucleotides which flank the above intact *APP* genes were used to specifically amplify those regions from chromosomal DNA. The 5' and 3' primer pairs utilized for each gene amplification were as follows: for omp20, the primers were ER80 (SEQ ID NO:56) and ER81 (SEQ ID NO:57); for omp27, the primers were ER95 (SEQ ID NO:69) and ER96 (SEQ ID NO:70); for ompA1, the primers were ER84 (SEQ ID NO:60) and ER86 (SEQ ID NO:62); for ompA2, the primers were ER87 (SEQ ID NO:63) and ER66 (SEQ ID NO:45); and for ompW, the primers were ER82 (SEQ ID NO:58) and ER83 (SEQ ID NO:59). PCR reactions were carried out in triplicate and contained 260 ng purified chromosomal DNA, 1×PC2 buffer (Ab Peptides, Inc.), 200 μM each dNTP, 100 pMol each primer, 7.5 U KlenTaq1 and 0.15 U cloned Pfu thermostable polymerases in a 100 μl final sample volume. Conditions for amplification consisted of denaturation (94° C., 5 min) followed by 30 cycles of denaturation (95° C., 30 sec), annealing (65° C., 30 sec), and polymerization (72° C., 2 min). A final extension (72° C., 7 min) completed the amplification of the target intact gene region. Following amplification, each of the triplicate samples were pooled and the specific product was purified by agarose gel electrophoresis and extraction with spin chromatography (QIAquick™, QIAGEN Inc., Santa Clarita, Calif.) prior to direct sequence analysis using DyeDeoxy termination reactions on an ABI automated DNA sequencer (Applied Biosystems, Foster City, Calif.).

Synthetic oligonucleotide primers were used to sequence both DNA strands of the amplified products from *APP* serotype-7. The primers employed for sequencing the *APP* protein genes are presented below in TABLE 2.

The nucleotide sequence of the ORF of omp20 is presented in SEQ ID NO:1 from nt 272 to 790. The nucleotide sequence of the ORF of ompW is presented in SEQ ID NO:3 from nt 376 to 1023. The nucleotide sequence of the ORF of omp27 is presented in SEQ ID NO:5 from nt 157 to 933. The nucleotide sequence of the ORF of ompA1 is presented in SEQ ID NO:7 from nt 614 to 1708. The nucleotide sequence of the ORF of ompA2 is presented in SEQ ID NO:9 from nt 197 to 1306.

TABLE 2

| APP Gene | Primer | (SEQ ID NO) |
|---|---|---|
| omp20 | ER79 | (55) |
| | ER80 | (56) |
| | ER81 | (57) |
| | AP19.1 | (15) |
| | AP19.2 | (16) |
| | AP19.3 | (17) |
| | AP19.4 | (18) |
| | AP19.5 | (19) |
| omp27 | ER88 | (64) |
| | ER89 | (65) |
| | ER91 | (66) |
| | ER94 | (68) |
| | ER95 | (69) |
| | ER96 | (70) |
| ompA1 | ER84 | (60) |
| | ER85 | (61) |
| | ER86 | (62) |
| | AP21.1 | (24) |
| | AP21.2 | (25) |
| | AP21.3 | (26) |
| | AP21.4 | (27) |
| | AP21.5 | (28) |
| | AP21.6 | (29) |
| | AP21.7 | (30) |
| | AP21.8 | (31) |
| | AP21.9 | (32) |
| ompA2 | ER66 | (45) |
| | ER87 | (63) |
| | AP22.1 | (33) |
| | AP22.2 | (34) |
| | AP22.3 | (35) |
| | AP22.4 | (36) |
| | AP22.5 | (37) |
| | AP22.6 | (38) |
| ompW | ER82 | (58) |

TABLE 2-continued

| APP Gene | Primer | (SEQ ID NO) |
| --- | --- | --- |
| | ER83 | (59) |
| | AP20.1 | (20) |
| | AP20.2 | (21) |
| | AP20.3 | (22) |
| | AP20.4 | (23) |

7.6.2. Similarity of *APP* Serotype-7 OmpA1 and OmpA2 Proteins

The amino acid sequences of the OmpA1 protein (SEQ ID NO:8) and the OmpA2 protein (SEQ ID NO:10) were deduced from SEQ ID NOS:7 and 9, respectively, and were aligned to compare their similarity. The deduced OmpA1 protein is 364 amino acids in length, which is 5 amino acids shorter than the deduced OmpA2 protein. The alignment of the *APP* proteins shown in FIG. 5 indicates that the two proteins share 73.1% (270/369) amino acid identity.

7.6.3. Comparison of *APP* Serotype-7 OmpW Protein to *Vibrio cholerae* OmpW

The amino acid sequence (SEQ ID NO:4) deduced from the nucleotide sequence (SEQ ID NO:3) of the ORF encoding the 23 kDa *APP* OmpW protein was determined to be most similar to the OmpW protein described for *Vibrio cholerae* (Jalajakumari, M. B., et al., 1990, Nucleic Acids Res. 18(8):2180). The amino acid sequences of these two proteins were aligned using the Clustal W (ver 1.4) multiple sequence alignment algorithm (Thompson, J. D., et al., 1994, Nucleic Acids Res., 22:46734680). This comparison indicated that the *APP* OmpW and *V. cholerae* OmpW proteins, which are 215 and 216 residues in length, respectively, share 44.9% (97/216) amino acid identity. The aligned proteins are shown in FIG. 6.

7.7. Southern Blot Hybridizations

The conservation of DNA sequences encoding the Omp20, OmpW, Omp27, OmpA1 and OmpA2 proteins among different *APP* serotypes was determined by performing Southern blot hybridization analysis using each of the 5 different coding sequences as probes against *APP* DNA from the different serotypes. Probes were generated with a PCR DIG™ Probe Synthesis Kit (Boehringer Mannheim, Inc., Indianapolis, Ind.) according to manufacturer's instructions. For example, the ompW probe was constructed in the following manner. A PCR product encompassing the ompW coding sequence was generated using ompW specific primers and *APP* serotype-7 DNA. *APP* serotype-7 genomic DNA (0.2 μg), 1 μM MW3 primer (SEQ ID NO:71), 1 μM primer RA52 (SEQ ID NO:80), 7.5 U KlenTaq1 polymerase (Ab Peptides, Inc.), 0.075 U Pfu polymerase (Stratagene), 1×KlenTaq1 buffer, and 0.2 mM dNTPs were combined in a 50 μl volume. PCR was carried out as follows: denaturation (94° C., 5 min); 35 cycles of denaturation (94° C., 30 sec), annealing (58° C., 30 sec), and polymerization (72° C., 1 min); and final extension (72° C. for 7 min). The ~650-bp ompW PCR product was purified following agarose gel electrophoresis using a JETsorb™ kit (GENOMED, Inc., Research Triangle Park, N.C.). The purified DNA was quantitated using a Low Mass DNA Ladder™ mass standard (GIBCO/BRL, Gaithersburg, Md.). A digoxigenin-labeled probe was generated by PCR amplification of 24 μg of the ompW PCR product, produced as described above, using a PCR DIG™ Probe Synthesis Kit according to manufacturer's instructions, and the PCR-generated probe was stored unpurified at −20° C.

EcoRI-digested *APP* genomic DNA (1.5 μg) obtained from each of *APP* serotypes 1, 2, 5, 7, 8 and 9 was separated by agarose gel electrophoresis. The DNA profiles were transferred to Hybond-N 0.45 μm nylon membrane (Amersham, Inc., Cleveland, Ohio) using alkaline transfer with a Turboblotter™ Kit (Schleicher & Schuell, Inc., Keene, N.H.), according to manufacturer's instructions. The DNA was covalently bound to the membrane by UV irradiation using a Stratalinker™ UV Cross-Linker (Stratagene) at the auto-crosslink setting (120 mJ/cm$^2$). The blots were allowed to dry and were stored at rm temp.

Nylon DNA blots were incubated in the presence of probe to allow hybridization for detection of probe sequences in multiple *APP* serotypes. Blots were pre-hybridized for 2.5 hr at 68° C. using an excess (0.2 ml/cm$^2$) of 1×Prehybridization Solution (GIBCO/BRL). Probe-hybridization solution was prepared by adding 5.4 μl of the unpurified digoxigenin-labeled probe to 500 μl of 1×Hybridization Solution (GIBCO/BRL) and boiling at 100° C. for 10 min. The probe was cooled to 0° C. for 1 min, and then added to sufficient 1×Hybridization Solution to give a total of 0.025 ml/cm$^2$ of blot. Blots were hybridized in this probe-hybridization solution mixture at 68° C. for 16 hours. Stringency washes were carried out on blots as follows: (i) 2 washes with an excess (0.2 ml/cm$^2$) of 2×SSC/0.1% SDS at 25° C. for 5 min; (ii) 2 washes with an excess (0.2 ml/cm$^2$) of 0.1×SSC/0.1% SDS at 68° C. for 15 min. Blots were then developed using a chemiluminescence method with a DIG™ High Prime DNA Labeling and Detection Starter Kit II and a DIG™ Wash and Block Buffer Set (Boehringer Mannheim, Inc., Indianapolis, Ind.), according to manufacturer's instructions. Developed blots were exposed to X-ray film for varying lengths of time to detect hybridizing bands.

Probes generated as above against omp20, ompW, omp27, ompA1 and ompA2 sequences hybridized with DNA in all the *APP* serotypes tested (serotypes 1, 2, 5, 7, 8 and 9). The sizes of the EcoRI bands detected were identical across all serotypes for ompA1 and ompA2, but were not conserved for omp20, ompW and omp27.

The size of the EcoRI fragments hybridized by the omp20 probe in each serotype was as follows: serotypes-1, 2, 7 and 9 gave a 5.8 kb fragment; serotype-5 gave a 6.1 kb fragment; serotype-8 gave a 5.0 kb fragment.

The size of the EcoRI fragments hybridized by the ompW probe in each serotype was as follows: serotype-1 gave a 1.15 kb fragment; serotype-2 gave a 1.1 kb fragment; serotype-5 gave a 1.0 kb fragment; serotype-7 gave a 0.9 kb fragment; serotype-8 gave a 1.05 kb fragment; and serotype-9 gave a 1.2 kb fragment.

The size of the EcoRI fragments hybridized by the omp27 probe in each serotype was as follows: serotypes-1, 2 and 9 gave an approximately 9.5 kb fragment; serotypes-5, 7 and 8 gave an approximately 10.5 kb fragment.

The size of the EcoRI fragments hybridized by the ompA1 probe was 2.3 kb in all serotypes. Weaker hybridizing fragments of 0.55 kb and 0.85 kb were also detected.

The size of the EcoRI fragments hybridized by the ompA2 probe was 0.85 kb in all serotypes. Weaker hybridizing fragments of 0.55 kb and 2.3 kb were also detected.

8. EXAMPLE: EXPRESSION OF RECOMBINANT *APP* PROTEINS 8.1. Host Strain

The *E. coli* host used for recombinant protein expression was *E. coli* LW14. The genotype of this strain is λ$^-$ IN(rrnD-rrnE)1 galE::Tn10 λc/857ΔH1 bio. This strain was provided by SmithKline Beecham Pharmaceuticals, King of Prussia, Pa., USA, and contains the temperature-sensitive λ repressor λc/857 which inhibits expression from λ promoters at 30° C. At 42° C., the repressor is inactivated and expression from λ promoters is enabled, yielding high-level transcription and protein synthesis. *E. coli* LW14 was propagated at 30° C.

8.2. Plasmid Expression Vectors

The expression vector used for recombinant protein synthesis was pEA181, alternatively designated pEA181KanRBS3. This vector is 6.766 kb in size, encodes kanamycin resistance (kan), and contains the strong λ promoter $p_L$. The vector contains an NdeI site just downstream of an optimized ribosome-binding site; the presence of this NdeI site allows for the precise placement of the Met start codon of a protein for optimal expression. The vector also encodes an NS1 leader fusion protein to enable enhanced expression of poorly expressed proteins. This vector was provided by SmithKline Beecham Pharmaceuticals (see also U.S. Pat. No. 4,925,799, and Rosenberg et al., 1983, Meth. Enzymol. 101:123–138).

The coding sequences of each of the five *APP* proteins were amplified by PCR using 5' specific primers designed to yield an NdeI site (CATATG) overlapping the Met start codon (ATG), and 3' specific primers designed for cloning into the 3' XbaI site in pEA181. The respective PCR products were initially cloned into the pGEM®-T Easy PCR cloning vector (Promega Corp), and transformed into commercially available competent *E. coli* DH5α (MAX Efficiency DH5α Competent Cells, GIBCO/BRL). The PCR products were excised from these plasmid clones as NdeI-XbaI or NdeI-SpeI fragments and cloned into NdeI-XbaI cut pEA181. Due to the presence of the strong λ promoter $p_L$, pEA181 derivatives could be transformed only into *E. coli* LW14 which repressed expression from the vector by the activity of the temperature-sensitive lambda repressor λc/857. Transformation and propagation of transformants bearing pEA181 and its derivatives were done at 30° C. *E. coli* LW14 was made competent by the method of Hanahan for the preparation of frozen competent cells (Hanahan, 1985, In: *DNA Cloning: A Practical Approach* (Glover, D., ed.) Vol 1, pp. 109–135, IRL Press, Oxford, England).

Due to difficulties with expression of mature OmpW in *E. coli* LW14, a leader peptide allowing enhanced protein synthesis was employed. This leader peptide, termed a "protective peptide" or "pp", protects recombinant proteins from proteolytic degradation, as based upon information from Sung et al., 1986, Proc. Natl. Acad. Sci. USA 83:561–565; Sung et al., 1987, Meth. Enzymol. 153:385–389; and U.S. Pat. No. 5,460,954, which references are incorporated herein by reference. The protective peptide, which consists of the amino acid sequence Met-Asn-Thr-Thr-Thr-Thr-Thr-Thr-Ser-Arg (SEQ ID NO:96), was fused to the N-terminus of each of the *APP* proteins by designing PCR primers to contain the protective peptide coding sequence upstream from the *APP* coding sequence. Amplification of the separate *APP* coding sequences with such primers generated sequences encoding the N-terminal protective peptide fused to the first amino acid in the mature (i.e., lacking the native signal sequence) *APP* protein. An NdeI site was positioned at the Met codon in the protective peptide so that it could be ligated into the NdeI site of pEA181. The primer pairs for the amplification of the protective peptide-*APP* protein coding sequences were as follows: for ompW, MW3 (SEQ ID NO:71) and RA52 (SEQ ID NO:80); for ompA1, RA78 (SEQ ID NO:88) and RA71 (SEQ ID NO:87); for ompA2, RA78 (SEQ ID NO:88) and RA69 (SEQ ID NO:86); for omp20, ER78 (SEQ ID NO:54) and ER73 (SEQ ID NO:51); and for omp27, ER92 (SEQ ID NO: 67) and ER94 (SEQ ID NO: 68).

8.3. Expression of Recombinant Proteins

The *E. coli* LW14 transformants bearing pEA181 derivatives encoding protective peptide fusions with the respective mature *APP* proteins OmpA1, OmpA2, Omp20, OmpW and Omp27, were propagated overnight at 30° C. in LB $Km^{50}$ (Luria Broth with 50 μg/ml kanamycin sulfate). The cultures were diluted 1:100 into 2×YT $Km^{50}$ medium (1.6% tryptone, 1% yeast extract, 0.5% NaCl, 1.25 mM NaOH, containing 50 μg/ml kanamycin sulfate) and were grown at 30° C. until $A_{600}$ was 0.8 to 1.0. The cultures were then shifted to 42° C. in a water bath incubator and incubated for 3 to 4 hr.

Wet cells of *E. coli* LW14 transformants from a 5 liter fermentation grown in 2×YT Km50 medium, and expressing either pp-OmpA1, pp-OmpA2, or pp-OmpW, were harvested by centrifugation. The cells were suspended in 0.1M Tris-HCl, pH 8.0, and lysed in a high pressure homogenizer. Inclusion bodies were collected by centrifugation (12,000 RCF, 30 min), and washed once or twice with 2×RIPA/TET which was in a 5:4 ratio. 2×RIPA is 20 mM Tris (pH 7.4), 0.3 M NaCl, 2.0% sodium deoxycholate, and 2% (v/v) Igepal CA-630™ (Sigma). TET is 0.1 M Tris (pH 8.0), 50 mM EDTA, and 2% (v/v) Triton X-100. The inclusion bodies were dissolved in 5 M guanidine-hydrochloride, adjusted to >1.4 mg/ml protein in 2.5 M guanidine-hydrochloride, and filter-sterilized (0.2 μm). This preparation was used for the vaccination trials as described below.

Wet cells of *E. coli* LW14 transformants from a 5 liter fermentation grown in 2×YT $Km^{50}$ medium, and expressing pp-Omp20, were harvested by centrifugation. The cells were suspended in 25% sucrose—50 mM Tris-HCl, pH 8.0 with lysozyme (cells dispersed in 0.5 ml sucrose buffer for every 50 ml culture; for each ml of sucrose buffer, 0.125 ml lysozyme solution at 10 mg/ml was added), and sonicated. Inclusion bodies were collected by centrifugation (12,000 RCF, 30 min), washed with 2×RIPA/TET as above, collected again by centrifugation, and washed with 0.1M glycine and Zwittergent 3-14 (Calbiochem) at pH 11. The pH was adjusted to 7.0, and the inclusion bodies were collected by centrifugation (12,000 RCF, 30 min), dissolved in 3.5 M guanidine hydrochloride (final protein concentration, 6.36 mg/ml), and filter-sterilized (0.2 μm). This preparation was used for the vaccination trials as described below.

Wet cells of *E. coli* LW14 transformants from a 1600 ml flask culture grown in 2×YT $Km^{50}$ medium, as described above, and expressing pp-Omp27, were harvested by centrifugation. The cells were suspended in 25% sucrose—50 mM Tris-HCl, pH 8.0, with lysozyme, as above, sonicated, washed with 2×RIPA/TET as above, and collected by centrifugation. The inclusion bodies were collected by centrifugation (12,000 RCF, 30 min), dissolved in 5 M guanidine hydrochloride (final protein concentration, 2.46 mg/ml), and filter-sterilized (0.2 μm). This preparation was used for the vaccination trials as described below.

9. EXAMPLE: IMMUNOLOGICAL CHARACTERIZATION OF RECOMBINANT *APP* PROTEINS 9.1. Materials and Methods 9.1.1. Preparation and Quantification of *APP* Whole Cell Antigens for Western Blot Whole bacterial cell antigens were prepared as described above in Section 6.1.4, except that HP growth medium was substituted for the MM3 medium and the cells were suspended in 10 ml of DPBS instead of 5 ml of DPBS. The protein concentration of each preparation was determined using a BCA Protein Assay kit (Pierce). In brief, each sample was diluted 1/10, 1/20, 1/40, and 1/80 in sterile deionized, distilled water ($ddH_2O$). BSA (protein standard) was diluted to concentrations ranging from 200 to 800 μg/ml. A 20 μl volume of sample or standard was added to triplicate wells in a 96-well microtitre plate, and 200 μl of Reagent B diluted 1/50 in Reagent A was added to each well. The plate was incubated at 37° C. for 30 min. Sample absorbance was determined at 560 nm. The protein concentration for each sample was calculated by extrapolation using the BSA standard curve.

9.1.2. Antibodies

The secondary antibodies used for Western blots included alkaline phosphatase-conjugated goat anti-porcine IgG (H+L) and goat anti-mouse IgG (H+L) (Kirkegaard and Perry Laboratories). These antibodies were used to visualize APP protein-specific antibody in serum or supernatant samples by Western blot analysis. Both antibodies were diluted 1/1000 in dilution buffer (PBS, 0.05% Tween 20, 5% skim milk powder) prior to use.

9.1.3. Vaccination Protocol

Recombinantly-expressed protein preparations, prepared as described above in Section 8.3 were diluted to 80 μg/ml in DPBS, and then combined 1:1 with 2×concentrated SEAM-1 adjuvant (80 μg/ml Quil A, 16 μg/ml cholesterol, 5% squalene, 1% Span 85, 0.1% vitamin A acetate, 0.1% ethanol, and 0.01% thimerosol). Male CF1 mice were injected s.c. with 0.25 ml of protein/adjuvant preparation equivalent to 10 μg recombinant protein, 10 μg Quil A and 2 μg of cholesterol. Negative (adjuvant) control groups received 0.25 ml of DPBS mixed 1:1 with adjuvant. The mice were vaccinated a second time with the same protein preparation at 20–22 days post-primary vaccination. Two weeks after the second vaccination, animals were anesthetized with $CO_2$ and bled by either the brachial artery or through cardiac puncture. The serum was separated from each blood sample, and serum pools from mice within the same group were stored at −20° C.

9.1.4. Western Blot Analysis

A volume of APP whole bacterial cell lysate (from APP serotype 1, 2, 5, 7, or 9; prepared as described above in Section 9.1.1) corresponding to 10 μg of protein was mixed with water to a final volume of 10 μl, and 2 μl of 5× reducing sample buffer (Pierce) was added. In a similar manner, an aliquot of recombinant protein (see Section 8.3 above) (protein load was variable) was also prepared. Samples were heated for 5 min at 100° C., and the entire volume was loaded into separate wells of a 15-well, 1.5 mm thick, 14% Tris-glycine gel (Novex). Pre-stained, broad-range molecular weight markers (5 μl/well) (BioRad) were also included in each gel. Separated proteins in selected gels were stained with Coomassie Blue.

Proteins separated by SDS-PAGE were transferred to PVDF membranes (BioRad) at 200 mA constant current for 1.5 hr. The blots were either: (i) incubated directly in blocking buffer (5% skim milk powder and 0.05% Tween 20 in PBS); or (ii) dried at rm temp, stored frozen at −20° C. until needed, then rehydrated in methanol, rinsed in water, and subsequently incubated in blocking buffer. Membranes were incubated in blocking buffer (also used as dilution buffer) overnight with gentle agitation. The blocking buffer was removed, and diluted serum or supernatant sample was added to the membrane, followed by a 1 hr incubation at rm temp. After removal of the test sample, membranes were washed 3 times for 5–10 min each time with PBST (PBS with 0.05% Tween 20). Alkaline phosphatase-conjugated anti-murine or anti-porcine IgG (H+L) antibodies were diluted, added to washed membrane, and incubated for 1 hr at rm temp. The membranes were washed with PBST, and the substrate BCIP/NBT (Kirkegaard and Perry Laboratories) was added to the membranes and incubated with gentle agitation until a suitable color reaction developed. The membranes were then rinsed with water to stop the reaction, and dried at rm temp.

9.2. Results

The antigenic characteristics of the novel APP proteins were determined using the following three methods. The first method used pig antibody probes, i.e., convalescent pig sera or ASC supernatants, obtained from animals experimentally infected with either APP serotype-1 or serotype-5, or serotype-5 followed by rechallenge with serotype-7, as immunological probes in Western blots containing the recombinantly-expressed APP proteins (TABLE 3). The second method used sera from mice immunized with the recombinantly-expressed APP proteins to probe Western blots containing APP antigens (whole bacterial cell pellets) (TABLE 4). The third method used sera from mice immunized with the recombinantly-expressed APP proteins to probe Western blots containing the recombinantly-expressed APP proteins (TABLE 5). The results of each method are described below.

9.2.1. Recognition of Recombinant APP Proteins by Pig Antibody Probes Generated Against APP Serotypes Antibody probes (sera or ASC supernatants) were obtained from pigs following experimental challenge with either APP serotype-1, or serotype-5, or serotype-5 followed by rechallenge with serotype-7. The sera were used to originally identify the novel APP proteins (FIGS. 1–4). TABLE 3 summarizes the reactivity of the antibody probes with the recombinantly-expressed APP proteins by Western blotting. ASC probes generated following challenge with serotype-5 and rechallenge with serotype-7 recognized OmpW, OmpA1, OmpA2, and Omp20 recombinant proteins. The ASC probes did not react immunologically with recombinant Omp27. In contrast, sera derived from animals that were challenged with serotype-1, or serotype-5, or serotype-5 followed by rechallenge with serotype-7, only recognized OmpA1 and OmpA2 recombinant proteins. An ASC probe obtained from a non-challenged control pig (No. 780) did not react with any of the recombinantly-expressed proteins. However, an additional non-challenged control pig (No. 779) reacted with all recombinantly-expressed proteins. In addition, serum from a non-challenged control pig (No. 1421) reacted with OmpA1 and OmpA2. These latter two animals were suspected of having been subclinically infected with APP.

9.2.2. Recognition of APP Proteins by Mouse Antisera Generated Against the Recombinant APP Proteins Antisera from mice immunized with the recombinantly-expressed APP proteins were used to probe Western blots containing APP antigens from bacterial cell pellets. Results are summarized in TABLE 4. Mice immunized with recombinant pp-OmpW, or pp-OmpA1, or pp-OmpA2 produced serum antibodies that recognized specific bands consistent with the predicted molecular weights of the particular APP protein. However, sera from mice immunized with either recombinant Omp20 or Omp27 did not react specifically with the particular native protein in any serotype tested.

9.2.3. Recognition of Recombinant APP Proteins by Mouse Antisera Generated Against the Recombinant APP Proteins Antisera from mice immunized with the recombinantly-expressed novel proteins were used to probe Western blots containing the recombinant APP proteins. Results are summarized in TABLE 5. Sera from mice immunized with recombinant OmpW, either as a GST or pp fusion protein, recognized recombinant OmpW, OmpA1, and OmpA2 proteins. Sera from mice immunized with either recombinant OmpA1 or recombinant OmpA2 reacted strongly with both OmpA1 and OmpA2 immunogens. Sera from mice immunized with recombinant Omp20 reacted strongly with recombinant Omp20, and to a lesser degree with recombinant OmpA1 and OmpA2. In contrast, sera from mice vaccinated with recombinant Omp27 did not recognize recombinant Omp27, but did react with recombinant OmpA1 and OmpA2. Sera from control mice vaccinated with PBS reacted very weakly with recombinant OmpA1 and OmpA2, and did not recognize recombinant OmpW, Omp20 or Omp27.

In summary, pigs that had been experimentally infected with *APP* produced local antibodies (ASC probes) that recognized OmpW, OmpA1, OmpA2, and Omp20 recombinant proteins, whereas serum antibodies only reacted with recombinant OmpA1 and OmpA2, as demonstrated by Western blotting (TABLE 3). Serum thus appears to be much more restricted in terms of immunological reactivity than the ASC probes. Neither serum nor ASC probes recognized recombinantly-expressed Omp27. It is possible that Omp27 is not recognized in a Western blot assay due to the denaturing conditions of the assay.

Immunological characterization of recombinant OmpW, OmpA1, and OmpA2 indicates that these proteins can induce serum antibodies that recognize the native proteins (based upon the predicted molecular weight) found in serotypes 1, 2, 5, 7, 8 and 9 (TABLE 4), as well as recognize the recombinantly-derived forms of these proteins (TABLE 5), and where recombinant Omp20 was also recognized.

Sera from mice immunized with recombinant Omp20 or Omp27 were used to probe Western blots containing whole bacterial cell antigens derived from in-vitro grown *APP* serotypes 1, 2, 5, 7, 8, and 9 (TABLE 4). These sera did not recognize bands consistent with their native form in any of the *APP* serotypes examined. It is possible that Omp20 and Omp27 represent antigens of *APP* that are only expressed in vivo, and thus would not be present in bacterial cell pellets prepared in the laboratory. Alternatively, these two proteins may have been denatured by the Western blotting procedure and rendered unrecognizable to specific antibodies.

TABLE 3

Reactivity Of Porcine Convalescent Sera And ASC Supernatants Against Recombinant APP Proteins

| Ab source[2] | Animal No. | APP challenge[3] | Recombinant Proteins[1] | | | | |
|---|---|---|---|---|---|---|---|
| | | | OmpW | OmpA1 | OmpA2 | Omp20 | Omp27 |
| Serum | 1157 | Serotype 1 | −[4] | + | + | − | − |
| Serum | 642 | Serotype 5 | − | + | + | − | − |
| Serum | 803 | Serotype 5 & 7 | − | + | + | − | − |
| Serum | 1421 | None | − | + | + | − | − |
| ASC probe | 803 | Serotype 5 & 7 | + | + | + | + | − |
| ASC probe | 808 | Serotype 5 & 7 | + | + | + | + | − |
| ASC probe | 779 | None | + | + | + | + | ND[5] |
| ASC probe | 780 | None | − | − | − | − | ND |

[1]Each of the recombinant proteins contained the protective peptide (pp), lacked the native signal sequence, and was derived from inclusion bodies (IB).
[2]Serum, diluted 1/125, or ASC probes, diluted 1/4, were tested for antibodies specific for each of the recombinant proteins.
[3]Animals were challenged with the APP serotype indicated. Animals No. 803 and 808 were challenged with serotype-5, allowed to recover from infection, and were then rechallenged with serotype-7.
[4]+ indicates the presence of a band corresponding to the indicated recombinant protein; − indicates that the serum or ASC probe did not react with the specified recombinant protein.
[5]ND = not determined.

TABLE 4

Reactivity Of Serum From Mice Immunized With Recombinant APP Proteins to APP Whole Cell Preparations

| Immunogen[2] | APP Antigen[1] | | | | | |
|---|---|---|---|---|---|---|
| | Serotype-1 | Serotype-2 | Serotype-5 | Serotype-7 | Serotype-8 | Serotype-9 |
| OmpW-GST[3] | +[4] | + | + | + | + | + |
| pp-OmpW | + | + | + | + | + | + |
| pp-OmpA1 | + | + | + | + | + | + |
| pp-OmpA2 | + | + | + | + | + | + |
| pp-Omp20 | − | − | − | − | − | − |
| pp-Omp27 | − | − | − | − | − | − |
| PBS | − | − | − | − | − | − |

[1]Proteins in whole bacterial cell preparations (10 μg per lane) were separated by SDS-PAGE, transferred to PVDF membranes, and probed with mouse serum (1/50).
[2]Mice were immunized twice s.c. with either a recombinant APP protein preparation or PBS (control).
[3]All recombinant APP proteins used for mouse immunizations were solubilized inclusion body preparations. All APP proteins contained the protective peptide except for OmpW which was utilized as either an OmpW-GST fusion protein or a pp-OmpW fusion protein.
[4]+ indicates the presence of a band corresponding to the recombinant protein used to immunize the animal; − indicates the absence of a specific band.

TABLE 5

Reactivity Of Serum From Mice Immunized With Recombinant APP Proteins Against The Recombinant APP Proteins

| Immunogen[2] | Antigen[1] | | | | |
|---|---|---|---|---|---|
| | OmpW[3] | OmpA1 | OmpA2 | Omp20 | Omp27 |
| OmpW-GST[4] | +[5] | + | + | − | ND[6] |
| pp-OmpW | + | + | + | − | ND |
| pp-OmpA1 | − | ++ | ++ | − | ND |
| pp-OmpA2 | − | ++ | ++ | − | ND |
| pp-Omp20 | − | + | + | ++ | ND |
| pp-Omp27 | − | + | + | − | − |
| PBS | | +/− | +/− | − | − |

[1]Recombinant proteins separated by SDS-PAGE were transferred to PVDF membranes and probed with mouse serum (1/50).
[2]Mice were immunized twice s.c. with a recombinant protein preparation or PBS (control).
[3]Each of the recombinant APP proteins in the SDS-PAGE gels contained the protective peptide (pp) and lacked the native signal sequence.
[4]All recombinant APP proteins used for mouse immunizations were from solubilized inclusion body preparations. All proteins contained the protective peptide except for OmpW which was utilized as either an OmpW-GST fusion protein or a pp-OmpW fusion protein, and all proteins lacked the native signal sequence.
[5](+) indicates that the test serum reacted with the specified recombinant protein; (−) indicates the absence of a specific band; for the PBS control, (+/−) indicates that these bands were visible but very faint as compared to serum from an immunized animal. (++) indicates a very strong immunoreactivity.
[6]ND = not determined.

EXAMPLE 10: ANIMAL STUDY TO TEST EFFICACY OF VARIOUS ANTIGEN COMBINATIONS 10.1 Materials and Methods Fifty apparently healthy, crossbred pigs (approximately 6.5 weeks of age) were obtained from a herd with no history of *APP* disease or vaccination. Animals were randomly assigned by litter and by ApxII cytolytic neutralization antibody titer to five groups of 10 pigs (98% of the animals had serum neutralization titers ≦1:200 prior to the initiation of study). Pigs were acclimated for one week prior to initiation of study.

Animals were vaccinated with 2 ml of the appropriate vaccine (*APP* proteins with pp and without signal sequence) or placebo by the intramuscular route (IM; left neck muscle) on day 0, when pigs were approximately 7.5 weeks of age. After 3 weeks, animals were boosted with a second 2 ml dose (IM; right neck muscle). TABLE 6 identifies the vaccines used for first and second vaccinations of the 5 groups of pigs.

TABLE 6

| Vaccine Group | Vaccine Components |
|---|---|
| A | 75 μg pp-OmpW |
| | 75 μg pp-OmpA1 |
| | 75 μg pp-OmpA2 |
| | 75 μg pp-Omp20 |
| | 75 μg pp-Omp27 |
| | 75 μg rApxI |
| | 75 μg rApxII |
| | 75 μg rOmlA (5) |
| | Adjuvanted with 500 μg |
| | Quil A/200 μg cholesterol |
| B | 75 μg rApxI |
| | 75 μg rApxII |
| | 75 μg rOmlA (5) |
| | Adjuvanted with 500 μg |
| | Quil A/200 μg cholesterol |
| C | 75 μg pp-OmpW |
| | 75 μg pp-OmpA1 |
| | 75 μg pp-OmpA2 |
| | 75 μg pp-Omp20 |
| | 75 μg pp-Omp27 |
| | Adjuvanted with 500 μg |
| | Quil A/200 μg cholesterol |
| D | Commercial Vaccine (whole cell APP bacterin containing serotypes 1, 5, and 7), with Emulsigen ® adjuvant |
| E | Phosphate Buffered Saline adjuvanted with 500 μg Quil A/200 μg cholesterol |

All pigs were observed for approximately 1 hr following vaccinations for vomiting, depression, diarrhea, ataxia-incoordination, increased respiration, and trembling. In addition, daily observations were made for 3 days following first and second vaccinations. Rectal temperatures were recorded one day prior to vaccination, immediately prior to vaccination, 6 hr following vaccination, and 1 day post-vaccination.

Two weeks following the second vaccination, pigs were challenged intranasally with a live virulent culture of *APP* serotype-1 (ATCC strain 27088) which causes approximately 50% mortality in non-immune pigs. A dose of 1.0 ml (0.5 ml per nostril) of culture containing $1.5 \times 10^7$ cfu/ml was used. All animals were anesthetized prior to challenge with an i.m. injection consisting of a combination of 50 mg telazol, 50 mg xylazine, and 50 mg ketamine per ml at the rate of 1.0 ml/50 pounds of body weight.

10.2. Results

No significant elevations in temperature were seen following first or second vaccinations with the recombinant proteins of the present invention. Significant post-vaccinal site reactions were observed in animals that received the commercial vaccine as compared to all other groups (TABLE 7). None of the animals that received the novel *APP* proteins alone (Group C), and only 1 animal that received a second vaccination of the novel *APP* proteins and ApxI/ApxII/Om1A(5) combination (Group A), exhibited post-vaccinal site reactions.

TABLE 7

| Vaccine Group | First Vaccination Site Reactions (cm³)* (% Affected Animals) | Second Vaccination Site Reactions (cm³)* (% Affected Animals) |
|---|---|---|
| A | 0 (0) | 2 (10) |
| B | 2 (10) | 17 (30) |
| C | 0 (0) | 0 (0) |
| D | 16 (30) | 68 (70) |
| E | 0 (0) | 0 (0) |

*Numbers represent group average

Group A, which was vaccinated with all of the novel *APP* proteins plus ApxII/ApxII/Om1A(5), had lower mortality than any other group, including the commercial vaccine (30% vs. 60%) (TABLE 8). The amount of lung damage (% lesions) was also less in Group A as compared to Groups B, C, and controls, but similar to the lung damage seen in animals that received the commercial vaccine (Group D).

TABLE 8

| Vaccine Group | Average Lesion (%) | Mortality (%) |
|---|---|---|
| A | 58 | 30 |
| B | 73 | 70 |
| C | 67 | 70 |
| D | 55 | 60 |
| E | 73 | 60 |

These results indicate that a vaccine comprised of the novel *APP* proteins of the present invention in combination with toxin antigens provides protection against a heterologous *APP* challenge, which protection is equivalent or superior to that of a commercial vaccine.

11. EXAMPLE: PREPARATION OF PLASMIDS AND DEPOSIT MATERIALS

Separate plasmid constructs were prepared encoding each of the *APP* proteins for deposit with the American Type Culture Collection (ATCC). Each construct contains the total ORF encoding the particular *APP* protein with its native signal sequence. The ORFs were inserted in the TA cloning site of pCR2.1Topo in the opposite orientation relative to the lactose promoter. The ORFs were obtained by PCR from *APP* serotype-7 genomic DNA using the primers listed below in TABLE 9. The host cells were *E. coli* Top10. Both host cells and vector are available from Invitrogen (Carlsbad, Calif.). The 5' primers all begin at the ATG start codon of the respective ORF.

The strains prepared as above, and listed in TABLE 9 below, were deposited with the ATCC at 10801 University Blvd, Manassas, Va., 20110, USA, on Oct. 15, 1998, and were assigned the listed accession numbers.

TABLE 9

| Protein | 5' Primer (SEQ ID NO) | 3' Primer (SEQ ID NO) | Construct Name | Strain Name | ATCC Accession No. |
|---|---|---|---|---|---|
| Omp20 | ER218 (89) | ER73 (51) | pER416 | Pz416 | 98926 |
| Omp27 | ER219 (90) | ER94 (68) | pER417 | Pz417 | 98927 |
| OmpW | ER220 (91) | RA52 (80) | pER418 | Pz418 | 98928 |
| OmpA1 | ER221 (92) | RA71 (87) | pER419 | Pz419 | 98929 |
| OmpA2 | ER222 (93) | RA69 (86) | pER420 | Pz420 | 98930 |

All patents, patent applications, and publications cited above are incorporated herein by reference in their entirety.

The present invention is not to be limited in scope by the specific embodiments described, which are intended as single illustrations of individual aspects of the invention. Functionally equivalent compositions and methods are within the scope of the invention.

What is claimed is:

1. A vaccine against *Actinobacillus pleuropneumoniae*, comprising an immunologically effective amount of
   (a) a substantially purified polypeptide comprising the amino acid sequence of amino acid residue 20 to amino acid residue 172 of SEQ ID NO:2,
   (b) a substantially purified polypeptide comprising the amino acid sequence of amino acid residue 22 to amino acid residue 215 of SEQ ID NO:4,
   (c) a substantially purified polypeptide comprising the amino acid sequence of amino acid residue 28 to amino acid residue 258 of SEQ ID NO:6,
   (d) a substantially purified polypeptide comprising the amino acid sequence of amino acid residue 20 to amino acid residue 364 of SEQ ID NO:8, and
   (e) a substantially purified polypeptide comprising the amino acid sequence of amino acid residue 20 to amino acid residue 369 of SEQ ID NO:10; an adjuvant; and a veterinarily acceptable carrier or diluent.

2. The vaccine of claim 1, wherein one or more of the polypeptides is a fusion protein comprising a carrier or fusion partner joined to the polypeptide.

3. The vaccine of claim 1, further comprising an immunomodulatory component.

4. A vaccine kit for vaccinating swine against *APP*, comprising a container comprising an immunologically effective amount of
   (a) a substantially purified polypeptide comprising the amino acid sequence of amino acid residue 20 to amino acid residue 172 of SEQ ID NO:2,
   (b) a substantially purified polypeptide comprising the amino acid sequence of amino acid residue 22 to amino acid residue 215 of SEQ ID NO:4,
   (c) a substantially purified polypeptide comprising the amino acid sequence of amino acid residue 28 to amino acid residue 258 of SEQ ID NO:6,
   (d) a substantially purified polypeptide comprising the amino acid sequence of amino acid residue 20 to amino acid residue 364 of SEQ ID NO:8, and
   (e) a substantially purified polypeptide comprising the amino acid sequence of amino acid residue 20 to amino acid residue 369 of SEQ ID NO:10; and an adjuvant.

5. The kit of claim 4, further comprising a second container comprising a veterinarily acceptable carrier or diluent.

\* \* \* \* \*

SEQUENCE LISTING

```
<160> NUMBER OF SEQ ID NOS: 96

<210> SEQ ID NO 1
<211> LENGTH: 1018
<212> TYPE: DNA
<213> ORGANISM: Actinobacillus pleuropneumoniae
<220> FEATURE:
<221> NAME/KEY: CDS
<222> LOCATION: (272)..(787)

<400> SEQUENCE: 1
ggttggaaaa caccttatga agtttacttc aaaaaatcgt tgcacttggt ttgacaattc      60
aagactaaaa atgaccggtc gtgagctaaa accgcatgac cgtactgtgg atgtgacgat     120
tcgtcgtatt cgtaaacact ttgaagatca ccctaataca ccggaaatca ttgtaaccat     180
tcatggtgaa ggttaccgtt tttgcggcga gttagagtag taattaaacg cctataagcg     240
tttagcatct tctttctaaa aaggacattt t atg aaa aat tta aca gtt tta         292
                                   Met Lys Asn Leu Thr Val Leu
                                     1               5 gca tta gca ggt tta ttc tct gcg tcg gca ttt gcc gca ccg gtc gga       340
Ala Leu Ala Gly Leu Phe Ser Ala Ser Ala Phe Ala Ala Pro Val Gly
              10                  15                  20 aat acc ttt acc ggc gta ggc gta ggc gtt gat ctc acc acg gta aaa       388
Asn Thr Phe Thr Gly Val Gly Val Gly Val Asp Leu Thr Thr Val Lys
          25                  30                  35 tat aaa gtg gac ggt gtg aaa ggt aaa caa tca acc ggt cct gcg tta       436
Tyr Lys Val Asp Gly Val Lys Gly Lys Gln Ser Thr Gly Pro Ala Leu
 40                  45                  50                  55 gtc gta gat tac ggt atg gat tac ggt gac aat ttt gtc ggt gtt gta       484
Val Val Asp Tyr Gly Met Asp Tyr Gly Asp Asn Phe Val Gly Val Val
                  60                  65                  70 caa ggt aaa gta aaa gta ggc agt aca aaa gta ttt agc gat gta aaa       532
```

-continued

```
Gln Gly Lys Val Lys Val Gly Ser Thr Lys Val Phe Ser Asp Val Lys
            75                  80                  85 caa aaa act aaa tat act gtc gct tat caa caa ggt tat cgt gta gct    580
Gln Lys Thr Lys Tyr Thr Val Ala Tyr Gln Gln Gly Tyr Arg Val Ala
        90                  95                 100 tct gat tta ctt ccg tat gtc aaa gtc gat gtg gcg caa agt aaa gtc    628
Ser Asp Leu Leu Pro Tyr Val Lys Val Asp Val Ala Gln Ser Lys Val
    105                 110                 115 ggc gat acc aat ttc cgt ggt tac ggt tac ggt gcc ggt gct aaa tat    676
Gly Asp Thr Asn Phe Arg Gly Tyr Gly Tyr Gly Ala Gly Ala Lys Tyr
120                 125                 130                 135 gcc gta tca agt aat gta gaa gtg ggt gcg gaa tat acg cgc agc aat    724
Ala Val Ser Ser Asn Val Glu Val Gly Ala Glu Tyr Thr Arg Ser Asn
                140                 145                 150 tta aga aaa agc ggt gct aaa tta aaa ggt aat gaa ttt act gcg aac    772
Leu Arg Lys Ser Gly Ala Lys Leu Lys Gly Asn Glu Phe Thr Ala Asn
            155                 160                 165 cta ggt tac cgt ttc taattatttt tcccttatga caagcggtcg tttcttgcaa    827
Leu Gly Tyr Arg Phe
        170 aaaatttgcg aaaacgacc gcttattttt ttattaatac tttatttact gagccatttt   887 ttcagctacg gttagaaaac cgtctgcagt cgcatagatt tcttcaaagc cttgcgcttg   947 tagaatacgg tcggacactt cacgaaatgc gccctctcca cctgccttt ctaatatcca   1007 atccgctttt g                                                       1018

<210> SEQ ID NO 2
<211> LENGTH: 172
<212> TYPE: PRT
<213> ORGANISM: Actinobacillus pleuropneumoniae

<400> SEQUENCE: 2

Met Lys Asn Leu Thr Val Leu Ala Leu Ala Gly Leu Phe Ser Ala Ser
  1               5                  10                  15

Ala Phe Ala Ala Pro Val Gly Asn Thr Phe Thr Gly Val Gly Val Gly
             20                  25                  30

Val Asp Leu Thr Thr Val Lys Tyr Lys Val Asp Gly Val Lys Gly Lys
         35                  40                  45

Gln Ser Thr Gly Pro Ala Leu Val Val Asp Tyr Gly Met Asp Tyr Gly
     50                  55                  60

Asp Asn Phe Val Gly Val Gln Gly Val Lys Val Gly Ser Thr
 65                  70                  75                  80

Lys Val Phe Ser Asp Val Lys Gln Lys Thr Lys Tyr Thr Val Ala Tyr
                 85                  90                  95

Gln Gln Gly Tyr Arg Val Ala Ser Asp Leu Leu Pro Tyr Val Lys Val
            100                 105                 110

Asp Val Ala Gln Ser Lys Val Gly Asp Thr Asn Phe Arg Gly Tyr Gly
        115                 120                 125

Tyr Gly Ala Gly Ala Lys Tyr Ala Val Ser Ser Asn Val Glu Val Gly
    130                 135                 140

Ala Glu Tyr Thr Arg Ser Asn Leu Arg Lys Ser Gly Ala Lys Leu Lys
145                 150                 155                 160

Gly Asn Glu Phe Thr Ala Asn Leu Gly Tyr Arg Phe
                165                 170

<210> SEQ ID NO 3
<211> LENGTH: 1188
```

```
<212> TYPE: DNA
<213> ORGANISM: Actinobacillus pleuropneumoniae
<220> FEATURE:
<221> NAME/KEY: CDS
<222> LOCATION: (376)..(1020)

<400> SEQUENCE: 3
ctaacgcata aagtaaatgt gccggttcaa tgtagttatt atcttttccg atagctaacg      60
attgggcttc tgcaagggct tcttgcaatt tggtagtaaa ttttcgaaa ttcatatttt     120 tactcctaaa tttcattaat ctgtatcgag cagaatttat accgcttcaa cgttttaata     180
aatggagcta gtcgaactta tttcaagtga aatgtgaaa aagatcgcaa aaataaatt      240 agtacctcgt tgtaggtact aaaatggcgt atatttgatt cttgtcaata aagttagcc     300 gaattgttct tagaatgtta ttaacgtaac gaattggtta ctttttatt tttaagaaaa     360 tattaagagg tcaaa atg aaa aaa gca gta tta gcg gca gta tta ggc ggt     411
                 Met Lys Lys Ala Val Leu Ala Ala Val Leu Gly Gly
                  1               5                  10 gcg tta tta gcg ggt tcg gca atg gca cat caa gcg ggc gat gtg att       459
Ala Leu Leu Ala Gly Ser Ala Met Ala His Gln Ala Gly Asp Val Ile
              15                  20                  25 ttc cgt gcc ggt gcg atc ggt gtg att gca aat tca agt tcg gat tat       507
Phe Arg Ala Gly Ala Ile Gly Val Ile Ala Asn Ser Ser Ser Asp Tyr
     30                  35                  40 caa acc ggg gcg gac gta aac tta gat gta aat aat aat att cag ctt       555
Gln Thr Gly Ala Asp Val Asn Leu Asp Val Asn Asn Asn Ile Gln Leu
 45                  50                  55                  60 ggt tta acc ggt acc tat atg tta agt gat aat tta ggt ctt gaa tta       603
Gly Leu Thr Gly Thr Tyr Met Leu Ser Asp Asn Leu Gly Leu Glu Leu
                 65                  70                  75 tta gcg gca aca ccg ttt tct cac aaa atc acc ggt aag tta ggt gca       651
Leu Ala Ala Thr Pro Phe Ser His Lys Ile Thr Gly Lys Leu Gly Ala
             80                  85                  90 aca gat tta ggc gaa gtg gca aaa gta aaa cat ctt ccg ccg agc ctt       699
Thr Asp Leu Gly Glu Val Ala Lys Val Lys His Leu Pro Pro Ser Leu
         95                 100                 105 tac tta caa tat tat ttc ttt gat tct aat gcg aca gtt cgt cca tac       747
Tyr Leu Gln Tyr Tyr Phe Phe Asp Ser Asn Ala Thr Val Arg Pro Tyr
    110                 115                 120 gtt ggt gcc ggt tta aac tat act cgc ttt ttc agt gct gaa agt tta       795
Val Gly Ala Gly Leu Asn Tyr Thr Arg Phe Phe Ser Ala Glu Ser Leu
125                 130                 135                 140 aaa ccg caa tta gta caa aac tta cgt gtt aaa aaa cat tcc gtc gca       843
Lys Pro Gln Leu Val Gln Asn Leu Arg Val Lys Lys His Ser Val Ala
                145                 150                 155 ccg att gcg aat tta ggt gtt gat gtg aaa tta acg gat aat cta tca       891
Pro Ile Ala Asn Leu Gly Val Asp Val Lys Leu Thr Asp Asn Leu Ser
            160                 165                 170 ttc aat gcg gca gct tgg tac aca cgt att aaa act act gcc gat tat       939
Phe Asn Ala Ala Ala Trp Tyr Thr Arg Ile Lys Thr Thr Ala Asp Tyr
        175                 180                 185 gat gtt ccg gga tta ggt cat gta agt aca ccg att act tta gat cct       987
Asp Val Pro Gly Leu Gly His Val Ser Thr Pro Ile Thr Leu Asp Pro
    190                 195                 200 gtt gta tta ttc tca ggt att agc tac aaa ttc taagtatttt gaaactgtta    1040
Val Val Leu Phe Ser Gly Ile Ser Tyr Lys Phe
205                 210                 215 tgagaaaggg agcgttaatc gctcccttt tgttgtaaaa aatccttgaa aaacgaccgc    1100
ttgttaagca caaaaatgta ggatcatttt agtgagcaat tcacgagtcg gctcaataaa   1160
```

-continued ttttgtttct aaaaattcat ccggctgg                                          1188

<210> SEQ ID NO 4
<211> LENGTH: 215
<212> TYPE: PRT
<213> ORGANISM: Actinobacillus pleuropneumoniae

<400> SEQUENCE: 4

Met Lys Lys Ala Val Leu Ala Ala Val Leu Gly Gly Ala Leu Leu Ala
1               5                   10                  15

Gly Ser Ala Met Ala His Gln Ala Gly Asp Val Ile Phe Arg Ala Gly
            20                  25                  30

Ala Ile Gly Val Ile Ala Asn Ser Ser Ser Asp Tyr Gln Thr Gly Ala
        35                  40                  45

Asp Val Asn Leu Asp Val Asn Asn Ile Gln Leu Gly Leu Thr Gly
    50                  55                  60

Thr Tyr Met Leu Ser Asp Asn Leu Gly Leu Glu Leu Ala Ala Thr
65                  70                  75                  80

Pro Phe Ser His Lys Ile Thr Gly Lys Leu Gly Ala Thr Asp Leu Gly
                85                  90                  95

Glu Val Ala Lys Val Lys His Leu Pro Pro Ser Leu Tyr Leu Gln Tyr
            100                 105                 110

Tyr Phe Phe Asp Ser Asn Ala Thr Val Arg Pro Tyr Val Gly Ala Gly
        115                 120                 125

Leu Asn Tyr Thr Arg Phe Phe Ser Ala Glu Ser Leu Lys Pro Gln Leu
    130                 135                 140

Val Gln Asn Leu Arg Val Lys Lys His Ser Val Ala Pro Ile Ala Asn
145                 150                 155                 160

Leu Gly Val Asp Val Lys Leu Thr Asp Asn Leu Ser Phe Asn Ala Ala
                165                 170                 175

Ala Trp Tyr Thr Arg Ile Lys Thr Thr Ala Asp Tyr Asp Val Pro Gly
            180                 185                 190

Leu Gly His Val Ser Thr Pro Ile Thr Leu Asp Pro Val Val Leu Phe
        195                 200                 205

Ser Gly Ile Ser Tyr Lys Phe
    210                 215

<210> SEQ ID NO 5
<211> LENGTH: 1171
<212> TYPE: DNA
<213> ORGANISM: Actinobacillus pleuropneumoniae
<220> FEATURE:
<221> NAME/KEY: CDS
<222> LOCATION: (157)..(930)

<400> SEQUENCE: 5
tatttgagct taggctttaa taaagctcga atcctaagcc aggaaatata gaaagtacat      60
taaatataat ttagtattgt attaatagag gataaagcca caactggca agcaagaatt     120 ggttttactt tttaacctca ctaaaaggag acaact atg aaa cat agc aaa ttc       174
                                        Met Lys His Ser Lys Phe
                                        1               5 aaa tta ttt aaa tat tat tta att agc ttt cct ttt att act ttt gca      222
Lys Leu Phe Lys Tyr Tyr Leu Ile Ser Phe Pro Phe Ile Thr Phe Ala
        10                  15                  20 agt aat gtt aat gga gcc gaa att gga ttg gga gga gcc cgt gag agt      270
Ser Asn Val Asn Gly Ala Glu Ile Gly Leu Gly Gly Ala Arg Glu Ser
    25                  30                  35

```
agt att tac tat tct aaa cat aaa gta gca aca aat ccc ttt tta gca      318
Ser Ile Tyr Tyr Ser Lys His Lys Val Ala Thr Asn Pro Phe Leu Ala
    40                  45                  50 ctt gat ctt tct tta ggt aat ttt tat atg aga ggg act gca gga att      366
Leu Asp Leu Ser Leu Gly Asn Phe Tyr Met Arg Gly Thr Ala Gly Ile
 55                  60                  65                  70 agc gaa ata gga tat gaa caa tct ttc act gac aat ttc agc gta tca      414
Ser Glu Ile Gly Tyr Glu Gln Ser Phe Thr Asp Asn Phe Ser Val Ser
                 75                  80                  85 ctg ttt gtt aac cca ttt gat ggt ttt tca att aaa gga aaa gac ttg      462
Leu Phe Val Asn Pro Phe Asp Gly Phe Ser Ile Lys Gly Lys Asp Leu
             90                  95                 100 tta cct gga tat caa agt att caa act cgc aaa act caa ttt gcc ttt      510
Leu Pro Gly Tyr Gln Ser Ile Gln Thr Arg Lys Thr Gln Phe Ala Phe
        105                 110                 115 ggt tgg gga tta aat tat aat ttg gga ggt tta ttc ggc tta aat gat      558
Gly Trp Gly Leu Asn Tyr Asn Leu Gly Gly Leu Phe Gly Leu Asn Asp
    120                 125                 130 act ttt ata tcc ttg gaa gga aaa agc gga aaa cgt ggt gcg agt agt      606
Thr Phe Ile Ser Leu Glu Gly Lys Ser Gly Lys Arg Gly Ala Ser Ser
135                 140                 145                 150 aat gtc agc tta ctt aaa tcg ttt aat atg acg aaa aat tgg aaa gtt      654
Asn Val Ser Leu Leu Lys Ser Phe Asn Met Thr Lys Asn Trp Lys Val
                155                 160                 165 tca cca tat att ggc tca agt tat tat tca tct aaa tat aca gat tat      702
Ser Pro Tyr Ile Gly Ser Ser Tyr Tyr Ser Ser Lys Tyr Thr Asp Tyr
            170                 175                 180 tac ttt ggt att aaa caa tcc gaa tta ggt aat aaa att aca tcc gta      750
Tyr Phe Gly Ile Lys Gln Ser Glu Leu Gly Asn Lys Ile Thr Ser Val
        185                 190                 195 tat aaa cct aaa gca gct tat gca aca cac ata ggt att aat act gat      798
Tyr Lys Pro Lys Ala Ala Tyr Ala Thr His Ile Gly Ile Asn Thr Asp
    200                 205                 210 tat gct ttc acg aac aat ctt ggc atg ggt tta tct gtc ggt tgg aat      846
Tyr Ala Phe Thr Asn Asn Leu Gly Met Gly Leu Ser Val Gly Trp Asn
215                 220                 225                 230 aaa tat tct aaa gaa att aag caa tct cct atc ata aaa cga gac tct      894
Lys Tyr Ser Lys Glu Ile Lys Gln Ser Pro Ile Ile Lys Arg Asp Ser
                235                 240                 245 caa ttt act tca tct ctt agc ctt tat tat aag ttc taaaatagaa          940
Gln Phe Thr Ser Ser Leu Ser Leu Tyr Tyr Lys Phe
            250                 255 tattctaggg agaatactca ttctttatct ttataaagtt aattgttct ccctgtttct    1000 atattattta gttacttgtt caaaagctac attggttatt ttgtcatttt ataaaagata   1060
ataaggtggt tattttgaaa attaagaaat atattaaata taccctattt actttccttt   1120
taggcatatc atatttatat tttggggggcg aaaacgaaaa ttatcaagag a           1171

<210> SEQ ID NO 6
<211> LENGTH: 258
<212> TYPE: PRT
<213> ORGANISM: Actinobacillus pleuropneumoniae

<400> SEQUENCE: 6

Met Lys His Ser Lys Phe Lys Leu Phe Lys Tyr Tyr Leu Ile Ser Phe
 1               5                  10                  15

Pro Phe Ile Thr Phe Ala Ser Asn Val Asn Gly Ala Glu Ile Gly Leu
            20                  25                  30
```

```
Gly Gly Ala Arg Glu Ser Ser Ile Tyr Tyr Ser Lys His Lys Val Ala
        35                  40                  45

Thr Asn Pro Phe Leu Ala Leu Asp Leu Ser Leu Gly Asn Phe Tyr Met
 50                  55                  60

Arg Gly Thr Ala Gly Ile Ser Glu Ile Gly Tyr Glu Gln Ser Phe Thr
 65                  70                  75                  80

Asp Asn Phe Ser Val Ser Leu Phe Val Asn Pro Phe Asp Gly Phe Ser
                 85                  90                  95

Ile Lys Gly Lys Asp Leu Leu Pro Gly Tyr Gln Ser Ile Gln Thr Arg
                100                 105                 110

Lys Thr Gln Phe Ala Phe Gly Trp Gly Leu Asn Tyr Asn Leu Gly Gly
            115                 120                 125

Leu Phe Gly Leu Asn Asp Thr Phe Ile Ser Leu Glu Gly Lys Ser Gly
        130                 135                 140

Lys Arg Gly Ala Ser Ser Asn Val Ser Leu Leu Lys Ser Phe Asn Met
145                 150                 155                 160

Thr Lys Asn Trp Lys Val Ser Pro Tyr Ile Gly Ser Ser Tyr Tyr Ser
                165                 170                 175

Ser Lys Tyr Thr Asp Tyr Tyr Phe Gly Ile Lys Gln Ser Glu Leu Gly
            180                 185                 190

Asn Lys Ile Thr Ser Val Tyr Lys Pro Lys Ala Ala Tyr Ala Thr His
        195                 200                 205

Ile Gly Ile Asn Thr Asp Tyr Ala Phe Thr Asn Asn Leu Gly Met Gly
    210                 215                 220

Leu Ser Val Gly Trp Asn Lys Tyr Ser Lys Glu Ile Lys Gln Ser Pro
225                 230                 235                 240

Ile Ile Lys Arg Asp Ser Gln Phe Thr Ser Ser Leu Ser Leu Tyr Tyr
                245                 250                 255

Lys Phe

<210> SEQ ID NO 7
<211> LENGTH: 1922
<212> TYPE: DNA
<213> ORGANISM: Actinobacillus pleuropneumoniae
<220> FEATURE:
<221> NAME/KEY: CDS
<222> LOCATION: (614)..(1705)

<400> SEQUENCE: 7 acgtaacta cttattcttc tcatgttgca acgccaattc ttgcagagaa attaatcccg    60
atgttacaaa aaggcgactt aggggagccg acacctgctg ctgaaatcga caacgtttac   120
ttacgtgata tcaacgatgc aatccgtaac catccgttg aattaatcgg tcaagagtta   180
cgtggttata tgacggatat gaaacgtatt tcatcgcaag gttaattaaa aattaatcaa   240
aagcctactt cgcaagaagt gggcttttg ttattcaagc cgcttaccgc tatcaatggt   300
aagtgatatg cataatagct tataaattat aagttgtttt aagcaaatat atctctatcg   360
gtaagtaaaa aattaattgt agatcattaa aaaacggata aaaaaatcta ttttttgagt   420
gaattacgca taaaaaatga tctaaattat aggtttagtt gtattttca atttttattt   480 ggtagaatac aactgtaata aaagcttaat tattttgaga tacacataaa ataatttacg   540
gctttattca ttatcccttt taggttaggg atttgtcttt aatagatgac gataaattta   600
gaggatcatc aaa atg aaa aaa tca tta gtt gct tta aca gta tta tcg     649
              Met Lys Lys Ser Leu Val Ala Leu Thr Val Leu Ser
                1               5                  10
```

-continued

| | | |
|---|---|---|
| gct gca gcg gta gct caa gca gcg cca caa caa aat act ttc tac gca<br>Ala Ala Ala Val Ala Gln Ala Ala Pro Gln Gln Asn Thr Phe Tyr Ala<br>15  20  25 | 697 |
| ggt gcg aaa gca ggt tgg gcg tca ttc cat gat ggt atc gaa caa tta<br>Gly Ala Lys Ala Gly Trp Ala Ser Phe His Asp Gly Ile Glu Gln Leu<br>30  35  40 | 745 |
| gat tca gct aaa aac aca gat cgc ggt aca aaa tac ggt atc aac cgt<br>Asp Ser Ala Lys Asn Thr Asp Arg Gly Thr Lys Tyr Gly Ile Asn Arg<br>45  50  55  60 | 793 |
| aat tca gta act tac ggc gta ttc ggc ggt tac caa att tta aac caa<br>Asn Ser Val Thr Tyr Gly Val Phe Gly Gly Tyr Gln Ile Leu Asn Gln<br>65  70  75 | 841 |
| gac aaa tta ggt tta gcg gct gaa tta ggt tat gac tat ttc ggt cgt<br>Asp Lys Leu Gly Leu Ala Ala Glu Leu Gly Tyr Asp Tyr Phe Gly Arg<br>80  85  90 | 889 |
| gtg cgc ggt tct gaa aaa cca aac ggt aaa gcg gac aag aaa act ttc<br>Val Arg Gly Ser Glu Lys Pro Asn Gly Lys Ala Asp Lys Lys Thr Phe<br>95  100  105 | 937 |
| cgt cac gct gca cac ggt gcg aca atc gca tta aaa cct agc tac gaa<br>Arg His Ala Ala His Gly Ala Thr Ile Ala Leu Lys Pro Ser Tyr Glu<br>110  115  120 | 985 |
| gta tta cct gac tta gac gtt tac ggt aaa gta ggt atc gca tta gta<br>Val Leu Pro Asp Leu Asp Val Tyr Gly Lys Val Gly Ile Ala Leu Val<br>125  130  135  140 | 1033 |
| aac aat aca tat aaa aca ttc aat gca gca caa gag aaa gtg aaa act<br>Asn Asn Thr Tyr Lys Thr Phe Asn Ala Ala Gln Glu Lys Val Lys Thr<br>145  150  155 | 1081 |
| cgt cgt ttc caa agt tct tta att tta ggt gcg ggt gtt gag tac gca<br>Arg Arg Phe Gln Ser Ser Leu Ile Leu Gly Ala Gly Val Glu Tyr Ala<br>160  165  170 | 1129 |
| att ctt cct gaa tta gcg gca cgt gtt gaa tac caa tgg tta aac aac<br>Ile Leu Pro Glu Leu Ala Ala Arg Val Glu Tyr Gln Trp Leu Asn Asn<br>175  180  185 | 1177 |
| gca ggt aaa gca agc tac tct act tta aat cgt atg ggt gca act gac<br>Ala Gly Lys Ala Ser Tyr Ser Thr Leu Asn Arg Met Gly Ala Thr Asp<br>190  195  200 | 1225 |
| tac cgt tcg gat atc agt tcc gta tct gca ggt tta agc tac cgt ttc<br>Tyr Arg Ser Asp Ile Ser Ser Val Ser Ala Gly Leu Ser Tyr Arg Phe<br>205  210  215  220 | 1273 |
| ggt caa ggt gcg gta ccg gtt gca gct ccg gca gtt gaa act aaa aac<br>Gly Gln Gly Ala Val Pro Val Ala Ala Pro Ala Val Glu Thr Lys Asn<br>225  230  235 | 1321 |
| ttc gca ttc agc tct gac gta tta ttc gca ttc ggt aaa tca aac tta<br>Phe Ala Phe Ser Ser Asp Val Leu Phe Ala Phe Gly Lys Ser Asn Leu<br>240  245  250 | 1369 |
| aaa ccg gct gcg gca aca gca tta gat gca atg caa acc gaa atc aat<br>Lys Pro Ala Ala Ala Thr Ala Leu Asp Ala Met Gln Thr Glu Ile Asn<br>255  260  265 | 1417 |
| aac gca ggt tta tca aat gct gcg atc caa gta aac ggt tac acg gac<br>Asn Ala Gly Leu Ser Asn Ala Ala Ile Gln Val Asn Gly Tyr Thr Asp<br>270  275  280 | 1465 |
| cgt atc ggt aaa gaa gct tca aac tta aaa ctt tca caa cgt cgt gcg<br>Arg Ile Gly Lys Glu Ala Ser Asn Leu Lys Leu Ser Gln Arg Arg Ala<br>285  290  295  300 | 1513 |
| gaa aca gta gct aac tac atc gtt tct aaa ggt gct ccg gca gct aac<br>Glu Thr Val Ala Asn Tyr Ile Val Ser Lys Gly Ala Pro Ala Ala Asn<br>305  310  315 | 1561 |
| gta act gca gta ggt tac ggt gaa gca aac cct gta acc ggc gca aca<br>Val Thr Ala Val Gly Tyr Gly Glu Ala Asn Pro Val Thr Gly Ala Thr<br>320  325  330 | 1609 |

-continued

```
tgt gac aaa gtt aaa ggt cgt aaa gca tta atc gct tgc tta gca ccg    1657
Cys Asp Lys Val Lys Gly Arg Lys Ala Leu Ile Ala Cys Leu Ala Pro
        335                 340                 345 gat cgt cgt gtt gaa gtt caa gtt caa ggt act aaa gaa gta act atg    1705
Asp Arg Arg Val Glu Val Gln Val Gln Gly Thr Lys Glu Val Thr Met
    350                 355                 360 taatttagtt aattttctaa agttaaatta gtaaccctct gcttattta agcaagaggg    1765 ttattttttt gttccatttt aattagtgct actcttcctg tgtttatatt tgtgtttatg    1825
ataaactctt cataactttt attcacttat agatgaaaat gaaatacagc ttaacccctt    1885 tccataccttt tcatttagcg gcaaatgcaa caaaatc                           1922

<210> SEQ ID NO 8
<211> LENGTH: 364
<212> TYPE: PRT
<213> ORGANISM: Actinobacillus pleuropneumoniae

<400> SEQUENCE: 8

Met Lys Lys Ser Leu Val Ala Leu Thr Val Leu Ser Ala Ala Val
  1               5                  10                  15

Ala Gln Ala Ala Pro Gln Gln Asn Thr Phe Tyr Ala Gly Ala Lys Ala
                 20                  25                  30

Gly Trp Ala Ser Phe His Asp Gly Ile Glu Gln Leu Asp Ser Ala Lys
             35                  40                  45

Asn Thr Asp Arg Gly Thr Lys Tyr Gly Ile Asn Arg Asn Ser Val Thr
         50                  55                  60

Tyr Gly Val Phe Gly Gly Tyr Gln Ile Leu Asn Gln Asp Lys Leu Gly
 65                  70                  75                  80

Leu Ala Ala Glu Leu Gly Tyr Asp Tyr Phe Gly Arg Val Arg Gly Ser
                 85                  90                  95

Glu Lys Pro Asn Gly Lys Ala Asp Lys Lys Thr Phe Arg His Ala Ala
                100                 105                 110

His Gly Ala Thr Ile Ala Leu Lys Pro Ser Tyr Glu Val Leu Pro Asp
            115                 120                 125

Leu Asp Val Tyr Gly Lys Val Gly Ile Ala Leu Val Asn Asn Thr Tyr
        130                 135                 140

Lys Thr Phe Asn Ala Ala Gln Glu Lys Val Lys Thr Arg Arg Phe Gln
145                 150                 155                 160

Ser Ser Leu Ile Leu Gly Ala Gly Val Glu Tyr Ala Ile Leu Pro Glu
                165                 170                 175

Leu Ala Ala Arg Val Glu Tyr Gln Trp Leu Asn Asn Ala Gly Lys Ala
            180                 185                 190

Ser Tyr Ser Thr Leu Asn Arg Met Gly Ala Thr Asp Tyr Arg Ser Asp
        195                 200                 205

Ile Ser Ser Val Ser Ala Gly Leu Ser Tyr Arg Phe Gly Gln Gly Ala
    210                 215                 220

Val Pro Val Ala Pro Ala Val Glu Thr Lys Asn Phe Ala Phe Ser
225                 230                 235                 240

Ser Asp Val Leu Phe Ala Phe Gly Lys Ser Asn Leu Lys Pro Ala Ala
                245                 250                 255

Ala Thr Ala Leu Asp Ala Met Gln Thr Glu Ile Asn Asn Ala Gly Leu
            260                 265                 270

Ser Asn Ala Ala Ile Gln Val Asn Gly Tyr Thr Asp Arg Ile Gly Lys
        275                 280                 285
```

```
Glu Ala Ser Asn Leu Lys Leu Ser Gln Arg Arg Ala Glu Thr Val Ala
        290                 295                 300

Asn Tyr Ile Val Ser Lys Gly Ala Pro Ala Ala Asn Val Thr Ala Val
305                 310                 315                 320

Gly Tyr Gly Glu Ala Asn Pro Val Thr Gly Ala Thr Cys Asp Lys Val
                325                 330                 335

Lys Gly Arg Lys Ala Leu Ile Ala Cys Leu Ala Pro Asp Arg Arg Val
            340                 345                 350

Glu Val Gln Val Gln Gly Thr Lys Glu Val Thr Met
        355                 360

<210> SEQ ID NO 9
<211> LENGTH: 1319
<212> TYPE: DNA
<213> ORGANISM: Actinobacillus pleuropneumoniae
<220> FEATURE:
<221> NAME/KEY: CDS
<222> LOCATION: (197)..(1303)

<400> SEQUENCE: 9
```

| | | |
|---|---|---|
| atgtaatatt aggactggaa agttcgaaat tacaaattga tattacaaat tgattgtagt | | 60 |
| tttgcttttt atccttgata attaactctc ttttttctct agtgagacga gagcattaaa | | 120 |
| tcaaaacttt ggtgccataa gcggtgctga agtgattttg ttttattaat cgatgacaat | | 180 |

```
ttagaggatc atcaaa atg aaa aaa tca tta gtt gct tta gca gta tta tca          232
               Met Lys Lys Ser Leu Val Ala Leu Ala Val Leu Ser
                 1               5                  10 gct gca gca gta gct caa gca gct cca caa caa aat act ttc tac gca           280
Ala Ala Ala Val Ala Gln Ala Ala Pro Gln Gln Asn Thr Phe Tyr Ala
             15                  20                  25 ggt gcg aaa gtt ggt caa tca tca ttt cac cac ggt gtt aac caa tta           328
Gly Ala Lys Val Gly Gln Ser Ser Phe His His Gly Val Asn Gln Leu
 30                  35                  40 aaa tct ggt cac gat gat cgt tat aat gat aaa aca cgt aag tat ggt           376
Lys Ser Gly His Asp Asp Arg Tyr Asn Asp Lys Thr Arg Lys Tyr Gly
 45                  50                  55                  60 atc aac cgt aac tct gta act tac ggt gta ttc ggc ggt tac caa atc           424
Ile Asn Arg Asn Ser Val Thr Tyr Gly Val Phe Gly Gly Tyr Gln Ile
                 65                  70                  75 tta aac caa aac aat ttc ggt tta gcg act gaa tta ggt tat gat tac           472
Leu Asn Gln Asn Asn Phe Gly Leu Ala Thr Glu Leu Gly Tyr Asp Tyr
             80                  85                  90 tac ggt cgt gta cgt ggt aac gat ggt gaa ttc cgt gca atg aaa cac           520
Tyr Gly Arg Val Arg Gly Asn Asp Gly Glu Phe Arg Ala Met Lys His
         95                 100                 105 tct gct cac ggt tta aac ttt gcg tta aaa cca agc tac gaa gta tta           568
Ser Ala His Gly Leu Asn Phe Ala Leu Lys Pro Ser Tyr Glu Val Leu
110                 115                 120 cct gac tta gac gtt tac ggt aaa gta ggt gtt gcg gtt gtt cgt aac           616
Pro Asp Leu Asp Val Tyr Gly Lys Val Gly Val Ala Val Val Arg Asn
125                 130                 135                 140 gac tat aaa tcc tat ggt gca gaa aac act aac gaa cca aca gaa aaa           664
Asp Tyr Lys Ser Tyr Gly Ala Glu Asn Thr Asn Glu Pro Thr Glu Lys
                145                 150                 155 ttc cat aaa tta aaa gca tca act att tta ggt gca ggt gtt gag tac           712
Phe His Lys Leu Lys Ala Ser Thr Ile Leu Gly Ala Gly Val Glu Tyr
            160                 165                 170 gca att ctt cct gaa tta gcg gca cgt gtt gaa tac caa tac tta aac           760
Ala Ile Leu Pro Glu Leu Ala Ala Arg Val Glu Tyr Gln Tyr Leu Asn
        175                 180                 185
```

```
aaa gcg ggt aac tta aat aaa gca tta gtt cgt tca ggc aca caa gat      808
Lys Ala Gly Asn Leu Asn Lys Ala Leu Val Arg Ser Gly Thr Gln Asp
        190                 195                 200 gtg gac ttc caa tat gct cct gat atc cac tct gta aca gca ggt tta      856
Val Asp Phe Gln Tyr Ala Pro Asp Ile His Ser Val Thr Ala Gly Leu
205                 210                 215                 220 tca tac cgt ttc ggt caa ggc gct gta gca cca gtt gtt gag cca gaa      904
Ser Tyr Arg Phe Gly Gln Gly Ala Val Ala Pro Val Val Glu Pro Glu
                    225                 230                 235 gtt gta act aaa aac ttc gca ttc agc tca gac gtt tta ttt gat ttc      952
Val Val Thr Lys Asn Phe Ala Phe Ser Ser Asp Val Leu Phe Asp Phe
                240                 245                 250 ggt aaa tca agc tta aaa cca gca gca gca aca gct tta gac gca gct     1000
Gly Lys Ser Ser Leu Lys Pro Ala Ala Ala Thr Ala Leu Asp Ala Ala
            255                 260                 265 aac act gaa atc gct aac tta ggt tta gca act cca gct atc caa gtt     1048
Asn Thr Glu Ile Ala Asn Leu Gly Leu Ala Thr Pro Ala Ile Gln Val
        270                 275                 280 aac ggt tat aca gac cgt atc ggt aaa gaa gct tca aac tta aaa ctt     1096
Asn Gly Tyr Thr Asp Arg Ile Gly Lys Glu Ala Ser Asn Leu Lys Leu
285                 290                 295                 300 tca caa cgc cgt gca gaa act gta gct aac tac tta gtt tct aaa ggt     1144
Ser Gln Arg Arg Ala Glu Thr Val Ala Asn Tyr Leu Val Ser Lys Gly
                    305                 310                 315 caa aac cct gca aac gta act gca gta ggt tac ggt gaa gca aac cca     1192
Gln Asn Pro Ala Asn Val Thr Ala Val Gly Tyr Gly Glu Ala Asn Pro
                320                 325                 330 gta acc ggc gca aca tgt gac aaa gtt aaa ggt cgt aaa gca tta atc     1240
Val Thr Gly Ala Thr Cys Asp Lys Val Lys Gly Arg Lys Ala Leu Ile
            335                 340                 345 gct tgc tta gca ccg gat cgt cgt gtt gaa gtt caa gta caa ggt gct     1288
Ala Cys Leu Ala Pro Asp Arg Arg Val Glu Val Gln Val Gln Gly Ala
        350                 355                 360 aaa aac gta gct atg taatatagtg ggtttt                               1319
Lys Asn Val Ala Met
365

<210> SEQ ID NO 10
<211> LENGTH: 369
<212> TYPE: PRT
<213> ORGANISM: Actinobacillus pleuropneumoniae

<400> SEQUENCE: 10

Met Lys Lys Ser Leu Val Ala Leu Ala Val Leu Ser Ala Ala Ala Val
 1               5                  10                  15

Ala Gln Ala Ala Pro Gln Gln Asn Thr Phe Tyr Ala Gly Ala Lys Val
                20                  25                  30

Gly Gln Ser Ser Phe His His Gly Val Asn Gln Leu Lys Ser Gly His
            35                  40                  45

Asp Asp Arg Tyr Asn Asp Lys Thr Arg Lys Tyr Gly Ile Asn Arg Asn
        50                  55                  60

Ser Val Thr Tyr Gly Val Phe Gly Gly Tyr Gln Ile Leu Asn Gln Asn
 65                 70                  75                  80

Asn Phe Gly Leu Ala Thr Glu Leu Gly Tyr Asp Tyr Tyr Gly Arg Val
                85                  90                  95

Arg Gly Asn Asp Gly Glu Phe Arg Ala Met Lys His Ser Ala His Gly
            100                 105                 110

Leu Asn Phe Ala Leu Lys Pro Ser Tyr Glu Val Leu Pro Asp Leu Asp
```

```
                115                 120                 125
Val Tyr Gly Lys Val Gly Val Ala Val Val Arg Asn Asp Tyr Lys Ser
    130                 135                 140

Tyr Gly Ala Glu Asn Thr Asn Glu Pro Thr Glu Lys Phe His Lys Leu
145                 150                 155                 160

Lys Ala Ser Thr Ile Leu Gly Ala Gly Val Glu Tyr Ala Ile Leu Pro
                165                 170                 175

Glu Leu Ala Ala Arg Val Glu Tyr Gln Tyr Leu Asn Lys Ala Gly Asn
                180                 185                 190

Leu Asn Lys Ala Leu Val Arg Ser Gly Thr Gln Asp Val Asp Phe Gln
            195                 200                 205

Tyr Ala Pro Asp Ile His Ser Val Thr Ala Gly Leu Ser Tyr Arg Phe
210                 215                 220

Gly Gln Gly Ala Val Ala Pro Val Val Glu Pro Glu Val Val Thr Lys
225                 230                 235                 240

Asn Phe Ala Phe Ser Ser Asp Val Leu Phe Asp Phe Gly Lys Ser Ser
                245                 250                 255

Leu Lys Pro Ala Ala Ala Thr Ala Leu Asp Ala Ala Asn Thr Glu Ile
            260                 265                 270

Ala Asn Leu Gly Leu Ala Thr Pro Ala Ile Gln Val Asn Gly Tyr Thr
        275                 280                 285

Asp Arg Ile Gly Lys Glu Ala Ser Asn Leu Lys Leu Ser Gln Arg Arg
    290                 295                 300

Ala Glu Thr Val Ala Asn Tyr Leu Val Ser Lys Gly Gln Asn Pro Ala
305                 310                 315                 320

Asn Val Thr Ala Val Gly Tyr Gly Glu Ala Asn Pro Val Thr Gly Ala
                325                 330                 335

Thr Cys Asp Lys Val Lys Gly Arg Lys Ala Leu Ile Ala Cys Leu Ala
            340                 345                 350

Pro Asp Arg Arg Val Glu Val Gln Val Gln Gly Ala Lys Asn Val Ala
        355                 360                 365

Met

<210> SEQ ID NO 11
<211> LENGTH: 20
<212> TYPE: PRT
<213> ORGANISM: Actinobacillus pleuropneumoniae
<220> FEATURE:
<221> NAME/KEY: SITE
<222> LOCATION: (18)
<223> OTHER INFORMATION: Xaa=unknown amino acid

<400> SEQUENCE: 11

Ala Pro Val Gly Asn Thr Phe Thr Gly Val Lys Val Tyr Val Asp Leu
 1               5                  10                  15

Thr Xaa Val Ala
            20

<210> SEQ ID NO 12
<211> LENGTH: 35
<212> TYPE: PRT
<213> ORGANISM: Actinobacillus pleuropneumoniae
<220> FEATURE:
<221> NAME/KEY: SITE
<222> LOCATION: (30)
<223> OTHER INFORMATION: Xaa=Asn or Val

<400> SEQUENCE: 12
```

-continued

```
His Gln Ala Gly Asp Val Ile Phe Arg Ala Gly Ala Ile Gly Val Ile
 1               5                  10                  15

Ala Asn Ser Ser Ser Asp Tyr Gln Thr Gln Ala Asp Val Xaa Leu Asp
             20                  25                  30

Val Asn Asn
         35

<210> SEQ ID NO 13
<211> LENGTH: 30
<212> TYPE: PRT
<213> ORGANISM: Actinobacillus pleuropneumoniae

<400> SEQUENCE: 13

Ala Glu Ile Gly Leu Gly Gly Ala Arg Glu Ser Ser Ile Tyr Tyr Ser
 1               5                  10                  15

Lys His Lys Val Ala Thr Asn Pro Phe Leu Ala Leu Asp Leu
             20                  25                  30

<210> SEQ ID NO 14
<211> LENGTH: 19
<212> TYPE: PRT
<213> ORGANISM: Actinobacillus pleuropneumoniae
<220> FEATURE:
<221> NAME/KEY: SITE
<222> LOCATION: (2)
<223> OTHER INFORMATION: Xaa=Asp or Glu
<220> FEATURE:
<221> NAME/KEY: SITE
<222> LOCATION: (14)
<223> OTHER INFORMATION: Xaa=unknown amino acid
<220> FEATURE:
<221> NAME/KEY: SITE
<222> LOCATION: (15)
<223> OTHER INFORMATION: Xaa=unknown amino acid
<220> FEATURE:
<221> NAME/KEY: SITE
<222> LOCATION: (17)
<223> OTHER INFORMATION: Xaa=unknown amino acid

<400> SEQUENCE: 14

Ala Xaa Pro Glu Asn Thr Phe Tyr Pro Gly Ala Lys Val Xaa Xaa Ser
 1               5                  10                  15

Xaa Phe His

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
aaaaatttgc gaaaaacgac                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
acttctacat tacttgatac                                              20

<210> SEQ ID NO 17
<211> LENGTH: 20
```

```
<212> TYPE: DNA
<213> ORGANISM: Artificial Sequence
<220> FEATURE:
<223> OTHER INFORMATION: Description of Artificial Sequence: Primer

<400> SEQUENCE: 17
tccgtatgtc aaagtcgatg                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 18
taaacaatca accggtcctg                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
ttaccttgta caacaccgac                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
aaaagcagta ttagcggcag                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
ttgatgtgcc attgccgaac                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
gttttaaact ttcagcactg                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
```
agttcgtcca tacgttggtg                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
aatatatctc tatcggtaag                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 25
ctaaacctat aatttagatc                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
tgtttccgca cgacgttgtg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 27
aagtaaacgg ttacacggac                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 28
atcaaccgta attcagtaac                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
atagtcataa cctaattcag                                              20

<210> SEQ ID NO 30
<211> LENGTH: 20
<212> TYPE: DNA
<213> ORGANISM: Artificial Sequence

```
<220> FEATURE:
<223> OTHER INFORMATION: Description of Artificial Sequence: Primer

<400> SEQUENCE: 30
gtatgggtgc aactgactac                                          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 31
aacacgtgcc gctaattcag                                          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
tgcttgagct accgctgcag                                          20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
gcgaaagttg gtcaatcatc                                          20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 34
ataacgatca tcgtgaccag                                          20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 35
tgcgtctaaa gctgttgctg                                          20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 36
atcaagctta aaaccagcag                                          20
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 37
ctataaatcc tatggtgcag                                                      20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 38
tgcacctaaa atagttgatg                                                      20

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 39
ggggatccgc dccdgtdggh aatacnttta cngg                                      34

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 40
ggggatccat ytattatwsw aaacataaag tdgcdacnaa tcc                            43

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 41
ggggatccgt accgcgatct gtgttttag                                            30

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 42
ggggatccgg tgctccggca gctaacg                                              27

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 43
ggggatccat acttacgtgt tttatcatta taacg					35

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 44
ggggatccgg tcaaaccct gcaaacg					27

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 45
tttgcccggg ctcttttatt gatttaagtt act					33

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 46
gactaacgca ggaccggttg attg					24

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 47
ggggatccgt gggtgcggaa tatacgcgca g					31

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 48
caacgtggat ccgaattcaa gcttc					25

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 49
gtcaccgtaa tccataccgt aatg					24

<210> SEQ ID NO 50

```
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 50
gattgtttac ctttcacacc gtccac                                         26

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 51
tcacccggga aaatatcta gaaacgg                                         27

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 52
ccgtggtgag atcaacgcct acgcctac                                       28

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 53
cctttcacac cgtccacttt atattttacc gtggtgag                            38

<210> SEQ ID NO 54
<211> LENGTH: 68
<212> TYPE: DNA
<213> ORGANISM: Artificial Sequence
<220> FEATURE:
<223> OTHER INFORMATION: Description of Artificial Sequence: Primer

<400> SEQUENCE: 54
gcgcatatga acaccaccac caccaccacc tctcgtgcac cggtcggaaa tacctttacc    60
ggcgtagg                                                             68

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 55
caagactaaa aatgaccggt cgtg                                           24

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Primer
```

<400> SEQUENCE: 56
tgaatttacg accacgtaaa tgttt                                    25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 57
ctatgtgaaa gcaaaagcgg attgg                                    25

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 58
ccgtccggtt gtttgactaa cgc                                      23

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 59
tcgaacaagc acaccagccg gatg                                     24

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 60
ggcggaatac ggtaactact tattc                                    25

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 61
cgcataaaaa atgatctaaa ttatagg                                  27

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 62
ggggaattca acgattttgc ttgc                                     24

<210> SEQ ID NO 63

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 63
gaattcttgc tcgtttgaat tagaag                                  26

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 64
ggtaattttt atatgagagg gactg                                   25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 65
caaacagtga tacgctgaaa ttgtc                                   25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 66
gcaacacaca taggtattaa tactg                                   25

<210> SEQ ID NO 67
<211> LENGTH: 66
<212> TYPE: DNA
<213> ORGANISM: Artificial Sequence
<220> FEATURE:
<223> OTHER INFORMATION: Description of Artificial Sequence: Primer

<400> SEQUENCE: 67
gcgcatatga acaccaccac caccaccacc tctcgtgccg aaattggatt gggaggagcc    60
cgtgag                                                        66

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 68
gtattctctc tagaatattc tattttag                                28

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 69
gccacatgaa gaattattat ttgagct 27

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 70
acgtgaaaaa taatctcttg ataat 25

<210> SEQ ID NO 71
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 71
cgccatatga acaccaccac caccaccacc tctcgtcatc aggcgggaga tgtgattttc 60

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 72
caycargcdg ghgatgtdat ytt 23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 73
gcdgadccdg araayacdtt yta 23

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 74
accggtacct atatgttaag tg 22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 75
ataggtaccg gttaaaccaa gc 22

<210> SEQ ID NO 76

```
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 76
gttgccgcta ataattcaag acc                                          23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 77
aayacnttyt ayccdggngc naa                                          23

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 78
nacdckdckr tcnggngcna rrca                                         24

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 79
datytcnacd ckdckrtcng g                                            21

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 80
cgctctagag attttttaca acaaaaaggg                                   30

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 81
gmnaayacnt tytaygynggn ngc                                         23

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 82
```
aayacnttyt aygynggngc naar                                              24

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 83
cargmnaaya cnttytaygy ngg                                               23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 84
gcnccncarg mnaayacntt yta                                               23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 85
cgcgcnccnc argmnaayac ntt                                               23

<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 86
cggtcgactg atttaagtta ctaaaaccc                                         29

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 87
cggtcgacgg gttactaatt taactttag                                         29

<210> SEQ ID NO 88
<211> LENGTH: 67
<212> TYPE: DNA
<213> ORGANISM: Artificial Sequence
<220> FEATURE:
<223> OTHER INFORMATION: Description of Artificial Sequence: Primer

<400> SEQUENCE: 88
gcgtcgacca tatgaacacc accaccacca ccacctctcg tgcgccacaa caaaatactt       60 tytacgc                                                                 67

<210> SEQ ID NO 89

```
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 89
atgaaaaatt taacagtttt agcattagca gg                               32

<210> SEQ ID NO 90
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 90
atgaaacata gcaaattcaa attatttaaa tattattt                         38

<210> SEQ ID NO 91
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 91
atgaaaaaag cagtattagc ggcagtatta gg                               32

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 92
atgaaaaaat cattagttgc tttaacagta ttatcg                           36

<210> SEQ ID NO 93
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 93
atgaaaaaat cattagttgc tttagcagta ttatca                           36

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence:N-terminal
      consensus sequence of OmpA-related proteins from
      Pasteurellaceae
<220> FEATURE:
<221> NAME/KEY: SITE
<222> LOCATION: (4)
<223> OTHER INFORMATION: Xaa=Ala or Glu
<220> FEATURE:
<221> NAME/KEY: SITE
<222> LOCATION: (9)
<223> OTHER INFORMATION: Xaa=Ala or Val

<400> SEQUENCE: 94

Ala Pro Gln Xaa Asn Thr Phe Tyr Xaa Gly Ala Lys Ala
```

```
                1               5              10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence:C-terminal
      consensus sequence of OmpA-related proteins from
      Pasteurellaceae

<400> SEQUENCE: 95

Cys Leu Ala Pro Asp Arg Arg Val Glu Ile
  1               5              10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence:protective
      peptide

<400> SEQUENCE: 96

Met Asn Thr Thr Thr Thr Thr Thr Ser Arg
  1               5              10
```